United States Patent
Kilcoin et al.

(10) Patent No.: US 10,737,267 B2
(45) Date of Patent: Aug. 11, 2020

(54) FLUIDIC APPARATUS AND METHODS USEFUL FOR CHEMICAL AND BIOLOGICAL REACTIONS

(71) Applicant: Omniome, Inc., San Diego, CA (US)

(72) Inventors: Christopher Kilcoin, San Diego, CA (US); Kristin Dills, San Diego, CA (US); Rebecca McGinley, San Diego, CA (US)

(73) Assignee: Omniome, Inc., San Diego, CA (US)

(*) Notice: Subject to any disclaimer, the term of this patent is extended or adjusted under 35 U.S.C. 154(b) by 258 days.

(21) Appl. No.: 15/922,661

(22) Filed: Mar. 15, 2018

(65) Prior Publication Data

US 2018/0280975 A1 Oct. 4, 2018

Related U.S. Application Data

(60) Provisional application No. 62/481,289, filed on Apr. 4, 2017.

(51) Int. Cl.
*B01L 3/00* (2006.01)
*G01N 30/60* (2006.01)
(Continued)

(52) U.S. Cl.
CPC ..... *B01L 3/502738* (2013.01); *B01L 3/50853* (2013.01); *C12Q 1/6869* (2013.01);
(Continued)

(58) Field of Classification Search
CPC .. B01L 3/502738; B01L 3/5027; B01L 3/502; B01L 3/50; B01L 3/502853;
(Continued)

(56) References Cited

U.S. PATENT DOCUMENTS

| 5,130,238 A | 7/1992 | Malek et al. |
| 5,455,166 A | 10/1995 | Walker |

(Continued)

FOREIGN PATENT DOCUMENTS

| WO | WO-89/10977 A1 | 11/1989 |
| WO | WO-91/06678 A1 | 5/1991 |

(Continued)

OTHER PUBLICATIONS

International Search Report dated Jul. 6, 2018, for PCT Application No. PCT/US2018/022754, filed Mar. 15, 2018, 5 pages.

(Continued)

*Primary Examiner* — Christine T Mui
(74) *Attorney, Agent, or Firm* — Mintz Levin Cohn Ferris Glovsky and Popeo, P.C.

(57) ABSTRACT

A reagent cartridge including (a) a support having reservoirs; (b) a main channel within the support, the channel having first and second ends exiting the support; (c) a pump channel that connects to the main channel between the first and second ends; (d) a valve manifold in the support, including (i) a first passage at the first end of the main channel, (ii) a second passage at the second end of the main channel, (iii) a first master valve between the pump channel and the first end of the main channel, (iv) a second master valve between the pump channel and the second end of the main channel, and (v) reservoir valves for regulating flow from individual reservoirs to the main channel. The valves can be normally closed diaphragm valves formed by magnetic pistons attached to an elastomeric sheet that is sandwiched in the support.

27 Claims, 53 Drawing Sheets

(51) Int. Cl.

| | | |
|---|---|---|
| *C12Q 1/6869* | (2018.01) | |
| *F04B 1/00* | (2020.01) | |
| *F04B 23/02* | (2006.01) | |
| *C12Q 1/68* | (2018.01) | |
| *C12Q 1/6806* | (2018.01) | |
| *G01N 30/88* | (2006.01) | |

(52) U.S. Cl.
CPC ............. *F04B 1/00* (2013.01); *F04B 23/025* (2013.01); *G01N 30/6091* (2013.01); *B01L 3/50273* (2013.01); *B01L 2200/16* (2013.01); *B01L 2300/0861* (2013.01); *B01L 2300/0867* (2013.01); *B01L 2300/0877* (2013.01); *B01L 2400/0478* (2013.01); *B01L 2400/0622* (2013.01); *B01L 2400/0638* (2013.01); *B01L 2400/0644* (2013.01); *B01L 2400/0655* (2013.01); *B01L 2400/0666* (2013.01); *C12Q 1/6806* (2013.01); *G01N 2030/8827* (2013.01)

(58) Field of Classification Search
CPC ........ B01L 3/5085; B01L 3/508; B01L 3/505; F01B 1/00; C12Q 1/6869; C12Q 1/68
USPC .................................................. 422/504, 50
See application file for complete search history.

(56) References Cited

U.S. PATENT DOCUMENTS

| | | |
|---|---|---|
| 5,599,675 A | 2/1997 | Brenner |
| 5,641,658 A | 6/1997 | Adams et al. |
| 5,695,934 A | 12/1997 | Brenner |
| 5,750,341 A | 5/1998 | Macevicz |
| 5,863,722 A | 1/1999 | Brenner |
| 5,888,737 A | 3/1999 | DuBridge et al. |
| 5,947,167 A | 9/1999 | Bogen et al. |
| 6,140,489 A | 10/2000 | Brenner |
| 6,175,002 B1 | 1/2001 | DuBridge et al. |
| 6,210,891 B1 | 4/2001 | Nyren et al. |
| 6,214,587 B1 | 4/2001 | Dattagupta et al. |
| 6,258,568 B1 | 7/2001 | Nyren |
| 6,274,320 B1 | 8/2001 | Rothberg et al. |
| 6,374,684 B1 | 4/2002 | Dority |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,226,035 B2 | 6/2007 | Kimura et al. |
| 7,315,019 B2 | 1/2008 | Turner et al. |
| 7,329,492 B2 | 2/2008 | Hardin et al. |
| 7,329,860 B2 | 2/2008 | Feng et al. |
| 7,405,281 B2 | 7/2008 | Xu et al. |
| 7,871,771 B2 | 1/2011 | Fuller et al. |
| 8,142,182 B2 | 3/2012 | Feick et al. |
| 8,399,196 B2 | 3/2013 | Hoser |
| 8,404,198 B2 * | 3/2013 | Amshey ............ B01L 3/502715 422/561 |
| 8,431,413 B2 | 4/2013 | Dority et al. |
| 8,632,975 B2 | 1/2014 | Vander Horn et al. |
| 8,663,918 B2 | 3/2014 | Connolly et al. |
| 8,716,006 B2 | 5/2014 | Kilcoin et al. |
| 8,845,984 B2 | 9/2014 | Amshey et al. |
| 8,894,946 B2 | 11/2014 | Nielsen et al. |
| 8,951,781 B2 | 2/2015 | Reed et al. |
| 9,121,058 B2 | 9/2015 | Stern et al. |
| 9,193,996 B2 | 11/2015 | Buermann et al. |
| 9,322,063 B2 | 4/2016 | Zhao |
| 9,347,086 B2 | 5/2016 | Connolly et al. |
| 9,476,080 B2 | 10/2016 | Li et al. |
| 9,777,325 B2 | 10/2017 | Stone et al. |
| 2002/0055100 A1 | 5/2002 | Kawashima et al. |
| 2004/0002090 A1 | 1/2004 | Mayer et al. |
| 2004/0096853 A1 | 5/2004 | Mayer |
| 2005/0035156 A1 | 2/2005 | Hersch et al. |
| 2005/0064460 A1 | 3/2005 | Holliger et al. |
| 2005/0130173 A1 | 6/2005 | Leamon et al. |
| 2007/0099208 A1 | 5/2007 | Drmanac et al. |
| 2007/0128624 A1 | 6/2007 | Gormley et al. |
| 2008/0009420 A1 | 1/2008 | Schroth et al. |
| 2008/0108082 A1 | 5/2008 | Rank et al. |
| 2009/0026082 A1 | 1/2009 | Rothberg et al. |
| 2009/0127589 A1 | 5/2009 | Rothberg et al. |
| 2009/0148933 A1 | 6/2009 | Battrell et al. |
| 2009/0247414 A1 | 10/2009 | Obradovic et al. |
| 2009/0269248 A1 | 10/2009 | Falb et al. |
| 2010/0111768 A1 | 5/2010 | Banerjee et al. |
| 2010/0137143 A1 | 6/2010 | Rothberg et al. |
| 2010/0282617 A1 | 11/2010 | Rothberg et al. |
| 2012/0270305 A1 | 10/2012 | Reed et al. |
| 2014/0287966 A1 | 9/2014 | Gray et al. |
| 2015/0045234 A1 | 2/2015 | Stone et al. |
| 2017/0022553 A1 | 1/2017 | Vijayan et al. |
| 2017/0191125 A1 | 7/2017 | Vijayan et al. |
| 2018/0044715 A1 | 2/2018 | Iyidogan et al. |

FOREIGN PATENT DOCUMENTS

| | | |
|---|---|---|
| WO | WO-2004/018497 A2 | 3/2004 |
| WO | WO-2004/018497 A3 | 3/2004 |
| WO | WO-2005/010145 A2 | 2/2005 |
| WO | WO-2005/010145 A3 | 2/2005 |
| WO | WO-2005/065814 A1 | 7/2005 |
| WO | WO-2007/123744 A2 | 11/2007 |
| WO | WO-2007/123744 A3 | 11/2007 |
| WO | WO-2015/193194 A1 | 12/2015 |

OTHER PUBLICATIONS

Written Opinion dated Jul. 6, 2018, for PCT Application No. PCT/US2018/022754, filed Mar. 15, 2018, 14 pages.

Bently,D.R. et al. (Nov. 6, 2008). "Accurate whole human genome sequencing using reversible terminator chemistry," *Nature* 456(7218):53-59.

Dean, F.B. et al. (Apr. 16, 2002). "Comprehensive human genome amplification using multiple displacement amplification," *PNAS USA* 99(8):5261-5266.

Dressman, D. et al. (Jul. 22, 2003, e-published Jul. 11, 2003). "Transforming single DNA molecules into fluorescent magnetic particles for detection and enumeration of genetic variations," *PNAS USA* 100(15):8817-8822.

Drmanac S. et al. (Jan. 1998). "Accurate sequencing by hybridization for DNA diagnostics and individual genomics," *Nat Biotechnol* 16(1):54-58.

Fodor, S.P. et al. (Feb. 15, 1991). "Light-directed, spatially addressable parallel chemical synthesis," *Science* 251(4995):767-773.

Lage, J.M. et al. (Feb. 2003). "Whole genome analysis of genetic alterations in small DNA samples using hyperbranched strand displacement amplification and array-CGH," *Genome Res* 13(2):294-307.

Lizardi, P.M. et al. (Jul. 1998). "Mutation detection and single-molecule counting using isothermal rolling-circle amplification," *Nat Genet* 19(3):225-232.

Walker, G.T. et al. (Apr. 11, 1992). "Strand displacement amplification—an isothermal, in vitro DNA amplification technique," *Nucleic Acids Res* 20(7):1691-1696.

* cited by examiner

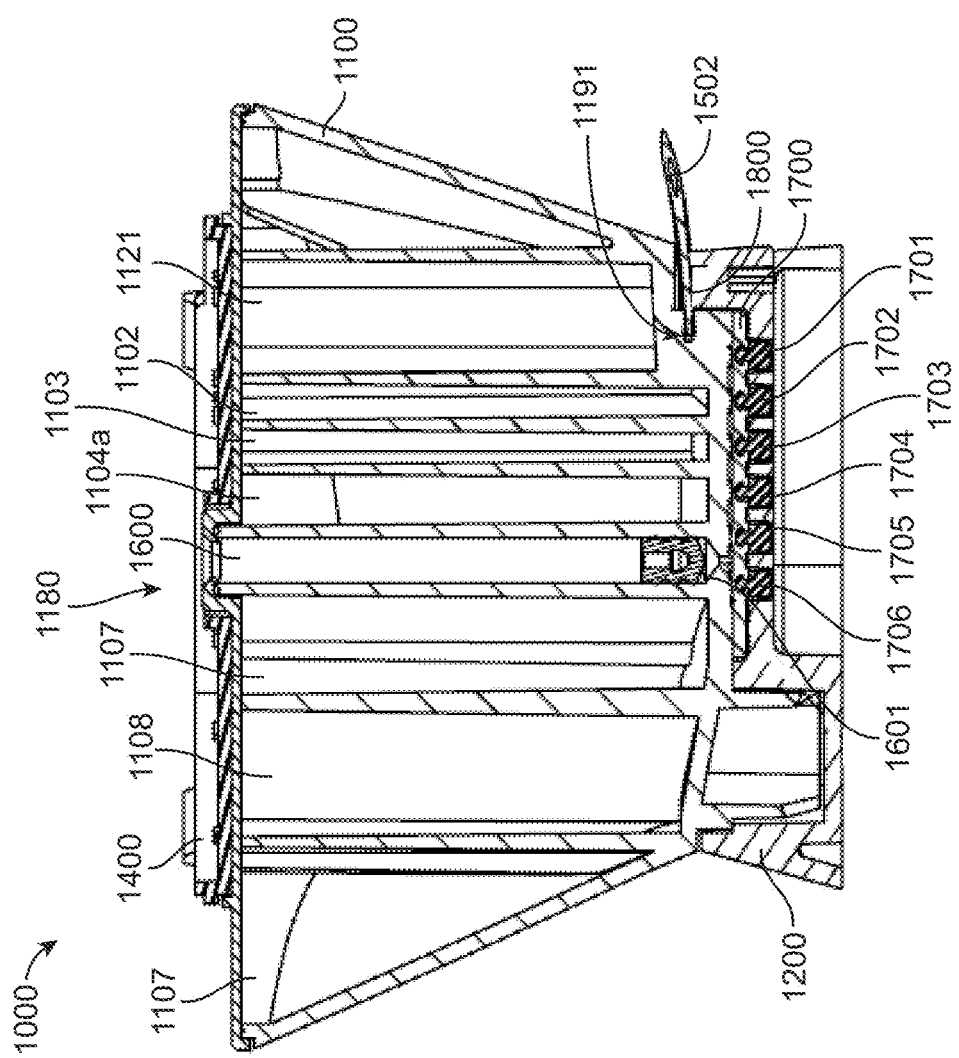

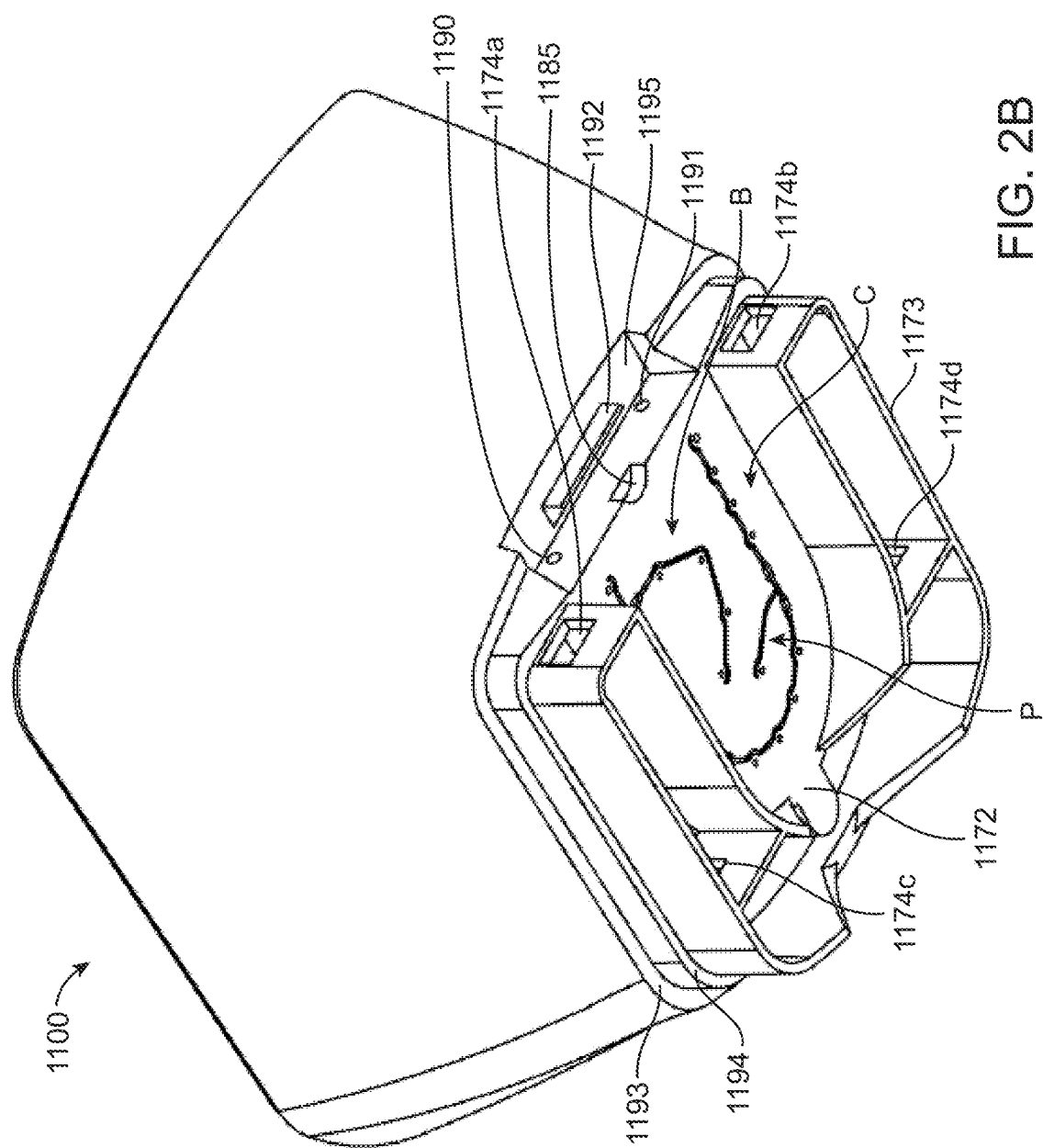

SECTION A-A

DETAIL C

| Step Name | System Pressure | Flow Direction | Time (s) | Valves | | | | | | | | | | | | | |
|---|---|---|---|---|---|---|---|---|---|---|---|---|---|---|---|---|---|
| | | | | 1 | 2 | 3 | 4 | 5 | 6 | 16 | 17 | 18 | 19 | 20 | 21 | 22 |
| Syringe Prime | (-) | N/A | 30 | | | | | | | | | | | | O | |
| Main Prime | (+) | counterclockwise | 10 | O | | | O | | O | | | | | | | O |
| Main Prime | (+) | counterclockwise | 10 | | | | O | O | | | | | | | | |
| Main Prime | (+) | counterclockwise | 10 | O | | | O | | O | | | | | | | O |
| Cluster Prime | (-) | counterclockwise | 20 | O | | | | O | | O | | | | O | | O |
| Main Prime | (+) | counterclockwise | 10 | O | | | O | | O | | | | | | | O |
| Surface Prep | (-) | counterclockwise | 20 | O | | | | O | | O | | | | O | | O |
| Sample Input | (-) | counterclockwise | 20 | O | | | | O | | O | | | O | | | O |
| RCA | (-) | counterclockwise | 20 | O | | | | O | | O | | O | | | | O |
| Primer Hyb | (-) | counterclockwise | 60 | O | | | | | | O | O | | | | | O |
| Syringe purge | (+) | clockwise | 10 | | | | O | | | | | | | | | |
| super wash | (-) | clockwise | 10 | O | | O | | | | | | | | | | O |
| super wash | (+) | clockwise | 10 | O | | | | O | O | | | | | O | | O |
| total | | | 240 | | | | | | | | | | | | | |

FIG. 10A

| Step Name | System Pressure | Flow Direction | Time (s) | Valves | | | | | | | | | | | | | | | |
|---|---|---|---|---|---|---|---|---|---|---|---|---|---|---|---|---|---|---|---|
| | | | | 1 | 2 | 4 | 5 | 6 | 8 | 9 | 10 | 11 | 12 | 13 | 14 | 15 | 21 | 22 |
| preincorp | (-) | counterclockwise | 5 | O | | | O | | | | | | | | | | | O |
| cleave | (-) | clockwise | 5 | O | O | | | O | | | | | | | | | | O |
| wash | (+) | counterclockwise | 10 | O | | O | | O | | | | | | | | | | O |
| incorp | (-) | counterclockwise | 5 | O | | | O | | | | | | | | | O | | O |
| wash | (+) | counterclockwise | 10 | O | | O | | O | | | | | | | | | | O |
| exam A | (-) | counterclockwise | 15 | O | | | O | | | | O | | | | | | O | O |
| wash | (+) | counterclockwise | 5 | O | | O | | O | | | | | | | | | | O |
| EDTA | (-) | counterclockwise | 3 | O | | | O | | O | | | | | | | | | O |
| wash | (+) | counterclockwise | 5 | O | | O | | O | | | | | | | | | | O |
| exam G | (-) | counterclockwise | 15 | O | | | O | | | | | O | | | | | O | O |
| wash | (+) | counterclockwise | 5 | O | | O | | O | | | | | | | | | | O |
| EDTA | (-) | counterclockwise | 3 | O | | | O | | O | | | | | | | | | O |
| wash | (+) | counterclockwise | 5 | O | | O | | O | | | | | | | | | | O |
| exam C | (-) | counterclockwise | 15 | O | | | O | | | | | | O | | | | O | O |
| wash | (+) | counterclockwise | 5 | O | | O | | O | | | | | | | | | | O |
| EDTA | (-) | counterclockwise | 3 | O | | | O | | O | | | | | | | | | O |
| wash | (+) | counterclockwise | 5 | O | | O | | O | | | | | | | | | | O |
| exam T | (-) | counterclockwise | 15 | O | | | O | | | | | | | O | | | O | O |
| wash | (+) | counterclockwise | 5 | O | | O | | O | | | | | | | | | | O |
| EDTA | (-) | counterclockwise | 3 | O | | | O | | O | | | | | | | | | O |
| wash | (+) | counterclockwise | 5 | O | | O | | O | | | | | | | | | | O |
| TOTAL | | | 147 | | | | | | | | | | | | | | | |

FIG. 10B

FLUIDIC APPARATUS AND METHODS USEFUL FOR CHEMICAL AND BIOLOGICAL REACTIONS

CROSS REFERENCE TO RELATED APPLICATION

This application claims priority to U.S. Provisional Application No. 62/481,289, filed Apr. 4, 2017, entitled "Fluidic Apparatus and Methods Useful for Chemical and Biological Reactions" the disclosure of which is incorporated herein by reference.

BACKGROUND

The present disclosure relates generally to synthetic and analytical reactions for chemical and biological analytes, and has specific applicability to nucleic acid sequencing.

The determination of nucleic acid sequence information is important in biological and medical research. Sequence information is helpful for identifying gene associations with diseases and phenotypes, identifying potential drug targets, and understanding the mechanisms of disease development and progress. Sequence information is an important part of personalized medicine, where it can be used to optimize the diagnosis, treatment, or prevention of disease for a specific individual.

Many scientists and medical practitioners struggle to tap into modern sequencing technology due to prohibitive costs to run and maintain complex instrumentation in current commercial offerings. These platforms favor centralized laboratories in which expensive "factory scale" instruments are run by highly trained specialists, and samples are batched to achieve economies of scale. This centralized system offers very little flexibility in terms of performance specifications—users are forced into ecosystems that are unnecessarily limited in scope and variety of use. When it comes to clinical applications, the centralized model is costly for doctors and their patients in terms of both the time and money required to ship patient samples from local clinics to distant sequencing labs. Further delays can be incurred as a centralized sequencing lab waits to receive an adequate number of samples to batch together into a run.

Thus, there is a need for a sequencing platform that is better suited for use in local laboratories in support of a decentralized system of research and clinical care. The present invention satisfies this need and provides related advantages as well.

BRIEF SUMMARY

The present disclosure provides a reagent cartridge that includes (a) a support having a plurality of reservoirs; (b) a main channel within the support, the channel having a first end exiting the support and a second end exiting the support; (c) a pump channel that connects the exterior of the support to a portion of the main channel that is between the first and second ends; (d) a valve manifold in the support, comprising (i) a first passage at the first end of the main channel, (ii) a second passage at the second end of the main channel, (iii) a first master valve that is placed in the main channel between the pump channel and the first end of the main channel, (iv) a second master valve that is placed in the main channel between the pump channel and the second end of the main channel, and (v) a plurality of reservoir valves for regulating flow from individual reservoirs to the main channel, wherein the reservoir valves are positioned to communicate with the main channel at a position between the first and second ends. Optionally, the plurality of reservoirs contains reagents for completing multiple cycles of a nucleic acid sequencing technique, wherein each of the cycles includes sequential delivery of reagents from multiple reservoirs of the plurality of reservoirs. The reservoirs can be sized to accommodate reagents for completing at least 2, 5, 10, 25, 50, 100, 500, 1000 or more cycles of a nucleic acid sequencing technique.

The plurality of reservoirs in the reagent cartridge can further include a waste reservoir for accepting the reagents for completing the cycles of the nucleic acid sequencing technique. The volume of the waste reservoir can be at least 100%, 80%, 60%, 40% or 20% of the total volume of the total volume of the other reagent reservoirs, or of the volume of reagents for completing the cycles of the nucleic acid sequencing technique. Optionally, the plurality of reservoirs can further include one or more amplification reservoir containing reagents for solid phase amplification of nucleic acids. In further options, one or more reservoirs can contain reagents for lysing cells or separating target amplicons from other nucleic acids.

In some embodiments, the reagent cartridge is fluidically connected to a flow cell, the flow cell having a detection channel, the detection channel having a first end fluidically connected to the first passage and the detection channel having a second end fluidically connected to the second passage, whereby the main channel and detection channel form a fluidic loop. Optionally, the detection channel can include a detection surface, the detection surface having nucleic acids or other analytes attached thereto. The detection channel can include a window that retains fluids in the channel and that is transparent to light (e.g. UV, VIS or IR light), and the window can be positioned to allow the detection surface to be detected by an external detector. In some embodiments, nucleic acids or other analytes are attached to the inner surface of the window (i.e. the detection surface is transparent to light).

As a further option, a first flow cell valve can be included in the cartridge for regulating flow through the first passage. In yet a further option, the cartridge can include a second flow cell valve for regulating flow through the second passage. Flow cell valves can provide a means to minimize cross contamination, for example, when fluids are intended to be transferred from one reservoir to another without entering the flow cell. Flow cell valves can also provide improved accuracy of fluid delivery to the flow cell by adding a second point of actuation in addition to reservoir valves.

The main channel can be connected to the detection channel of a flow cell to form a fluidic loop and the reservoirs can connect to the loop in a variety of configurations. In an exemplary nucleic acid sequencing configuration, the fluidic loop includes, in relative order, the connection to the pump channel, the second master valve, a reservoir valve for a wash reservoir that contains a wash reagent, reservoir valves for nucleotide reservoirs that contain nucleotide analogs, the second passage, the flow cell, the first passage, the first master valve and then the aforementioned connection to the pump channel. In the exemplary nucleic acid sequencing configuration, the plurality of reservoirs can further include a waste reservoir for accepting the reagents after they are used in the sequencing cycles and a reagent valve for the waste reservoir can be located in the fluidic loop between the first passage and the first master valve. As a further option, the plurality of reservoirs can further include at least one amplification reservoir containing one or more reagents for solid phase amplification of nucleic acids, and a reagent valve for the amplification reservoir can be located in the fluidic loop between the reservoir valves for nucleotide reservoirs and the second passage. Further still, the plurality of reservoirs can include a deblocking reservoir containing a reagent for removing a reversible terminator from the 3' end of a nucleic acid and a reagent valve for the deblocking reservoir can be located in the fluidic loop between the second passage and the reagent valve for the waste reservoir. A reservoir for separation of amplification products can also be present. For example, the reservoir can contain magnetic beads that are able to capture nucleic acids, for example, via hybridization of capture probes on the beads to target sequences in a mixture of amplification products.

In some embodiments, the valves in the reagent cartridge are diaphragm valves. For example, the valve manifold can include an elastomer sheet that is attached to a plurality of pistons that are magnetic or ferromagnetic. The valves can be in a normally closed configuration and can be opened by force applied to the pistons. For simplicity of explanation, magnetic pistons will be exemplified herein in the context of use with ferromagnetic actuators; conversely, ferromagnetic pistons can be used with magnetic actuators. The reagent cartridge can include a body component and a foot component, and the elastomer sheet can be compressed between the body component and the foot component. Optionally, the plurality of reservoirs, the main channel and the pump channel are present in the body component, and the foot component includes shafts for the magnetic pistons. Pulling the magnetic pistons through the shafts, away from the body component, will pull a localized area of elastomer sheet away from openings in the body component, effectively opening a diaphragm valve to allow localized fluid flow.

In particular embodiments, the reagent cartridge further includes a first flexible tube having a first end attached to the first end of the main channel and a second end protruding from the support. Additionally, the reagent cartridge can include a second flexible tube having a first end attached to the second end of the main channel and having a second end protruding from the support. Optionally, a chamber can be present in the reagent cartridge to house a metal sheet and the flexible tubes can be attached to the cartridge by compression of exterior surfaces of the tubes against an edge of the metal sheet. Typically, the edge of the metal sheet will contact the flexible tubes at an acute or obtuse angle with respect to the length of each of the flexible tubes. This configuration can prevent a pulling force from disconnecting the tubes from the main channel of the reagent cartridge. Thus, the metal sheet bites into the flexible tubes to hold them in place and to urge the end of the tube toward the opening of the main channel to which the tube will connect.

The reagent cartridge can further include a lid that is configured to rotate between an open position and a closed position, the open position providing fluidic access from outside the body component to the insides of the reservoirs. This access can be used to fill the reservoirs for example via pipetting action. Optionally, the lid further includes gas vents that connect each of the reservoirs to the outside of the body when the lid is in the closed position. This will prevent a vacuum from forming in the reservoirs that would inhibit movement of fluids into the main channel when pump pressure is applied to the main channel.

The reagent cartridge can optionally be connected to a nucleic acid sequencing apparatus. The sequencing apparatus can further include a syringe pump that functionally connects to the pump channel. For example, the syringe pump can include a plunger that moves in a barrel formed by the pump channel. In some embodiments, the nucleic acid sequencing apparatus can further include a flow cell having a detection channel, the detection channel having a first end fluidically connected to the first passage and the detection channel having a second end fluidically connected to the second passage. The nucleic acid sequencing apparatus can further include a detector configured to detect nucleic acids or other analytes in the flow cell. The sequencing apparatus can also include actuators for magnetic pistons that operate as valves in the cartridge and one or more heater elements for temperature control of the cartridge and/or flow cell. The magnets can be positioned to push up against a thin membrane on the bottom of a reagent cartridge. This membrane can be formed by a thin wall in the bottom of a chamber in the cartridge body, or more optimally, by heat sealing a thin film onto the bottom of the cartridge body. Magnets can also be present in the sequencing apparatus in a configuration for separation of magnetic particles (see, for example, FIG. 16F). This allows magnetic separation of nucleic acids (e.g. capture of magnetic particles with target nucleic acid while unbound reaction components are washed away).

The present disclosure further provides a valve manifold that includes (a) an elastomer sheet attached to a plurality of magnetic pistons, wherein the magnetic pistons project from a first side of the elastomer sheet; (b) a foot component that includes a first surface and a plurality of shafts that orthogonally pass through the first surface; and (c) a body component that includes a second surface, a groove that laterally passes along the second surface, and a plurality of reservoir channels that orthogonally pass through the second surface, wherein the elastomer sheet is compressed between the foot component and the body component, wherein the first side of the elastomer sheet contacts the first surface and the magnetic pistons protrude from the first side of the elastomer sheet into the shafts of the foot component, wherein a second side of the elastomer sheet contacts the second surface to form normally closed valves that seal the plurality of reservoir channels from fluidically communicating with the groove, and wherein the normally closed valves are actuated by movement of the magnetic pistons through the shafts away from the first surface, thereby pulling the second side of the elastomer sheet away from the reservoir channels to fluidically connect the groove and the reservoir channels in the body component.

The valve manifold can further include a plurality of actuators that are configured to open the normally closed valves by magnetically attracting the magnetic pistons through the shafts and away from the first surface.

In particular embodiments, each magnetic piston of the valve manifold is attached to the elastomer sheet by a protrusion that is inserted into the interior of the elastomer sheet. The protrusion can include a head region that is connected to the piston via a narrow neck. As such, the head will have a broad surface around the connection to the head and the broad surface will resist removal of the head from the interior of the elastomer sheet when the piston is pulled. The elastomer sheet can be homogenous in composition, for example, having an interior, first side and second side that consist essentially of the same material. The magnetic pistons can be attached to the elastomer sheet using a process of insert-molding the elastomer sheet over the head and neck at the end of each piston, thereby yielding pistons that are inserted into the elastomer sheet. In an alternative embodiment, the magnetic pistons can be attached to the elastomer sheet by adhering an end of the pistons to the second side of the elastomer sheet.

In some embodiments, the valve manifold further includes a master valve that regulates fluid flow through the groove, the master valve being formed by a node on the second side of the elastomer sheet that fills an aperture in the groove to prevent flow of fluid through the groove. The node can be formed opposite a magnetic piston. In this configuration, the master valve can be actuated by movement of the magnetic piston through a shaft in the foot component away from the first surface, thereby allowing flow of fluid through the groove by pulling the node out of the aperture.

Optionally, a pressure source can be connected to the groove of the valve manifold. In one configuration, the groove includes, in relative order, a first master valve, the connection of the pressure source to the groove and a second master valve. Thus, pressure can be controlled in the channel via independent actuation of master valves that flank the connection of the groove to the pressure source. The direction of fluid flow in the channel can be changed by opening one or the other master valve. Optionally, the master valves each include a node on the second side of the elastomer sheet that fills an aperture in the groove to prevent flow of fluid through the groove. The pressure source can create positive or negative pressure in the groove. A particularly useful pressure source that is capable of creating positive and negative pressure is a syringe pump. Thus, a second option for controlling the direction of fluid flow in the channel is to apply either positive or negative pressure to the loop.

In particular embodiments, the body component of the valve manifold further includes a plurality of reservoirs and the reservoirs are in fluid communication with the groove via the reservoir channels and via the valves.

The present disclosure further provides a method for performing a cyclical reaction. The method can include steps of (a) providing a reagent cartridge, the reagent cartridge including (i) a main channel, (ii) a series of fluid components in the main channel including, in relative order, a first passage, a first reservoir valve, a first pump valve, a second pump valve, a second reservoir valve, and a second passage, and (iii) first and second reservoirs that are connected to the main channel via the first and second reservoir valves, respectively, wherein the reservoirs include reagents for a cyclical reaction; (b) coupling the reagent cartridge with a detection apparatus, whereby (i) a flow cell having a first end is connected to the main channel via the first passage and a second end is connected to the main channel via the second passage; (ii) a detector is positioned to observe the flow cell, and (iii) a pump is positioned to apply pressure in the main channel at a region that is between the first master valve and the second master valve; (c) opening the first master valve and the second reservoir valve, while the second master valve is closed, to deliver reagent from the second reservoir to the flow cell in a first direction; (d) opening the second master valve and the first reservoir valve, while the first master valve is closed, to deliver reagent from the first reservoir to the flow cell in a second direction, the second direction being opposite the first direction; (e) detecting the cyclical reaction in the flow cell using the detector; and (f) repeating steps (b) through (e) to complete multiple cycles of the cyclical reaction. Optionally, the method can further include a step of (g) removing the reagent cartridge from the detection device. As a further option, the method can include a step of (h) repeating steps (a) through (f) for a second reagent cartridge that contains reagents for a second cyclical reaction.

In some embodiments of the methods, the flow cell is connected to the main channel via the first passage and the second passage prior to coupling the reagent cartridge with the detection apparatus in step (b). Alternatively, the flow cell can be connected to the main channel via the first passage and the second passage after the reagent cartridge is coupled with the detection apparatus. Thus, the flow cell can be an integral component of the reagent cartridge, or alternatively, the flow cell can be a separate component that is attached to the reagent cartridge either prior to or after the cartridge is coupled to the detection apparatus. In some embodiments, the flow cell can be an integral component of the detection apparatus such that the flow cell is coupled to the reagent cartridge during (or after) coupling the reagent cartridge to the detection apparatus.

In some embodiments of the methods, the pump is positioned to apply pressure in the main channel prior to coupling the reagent cartridge with the detection apparatus in step (b). Alternatively, the pump can be connected to the main channel after the reagent cartridge is coupled with the detection apparatus. Thus, the pump can be an integral component of the reagent cartridge, or alternatively, the pump can be a separate component that is attached to the reagent cartridge either prior to or after the cartridge is coupled to the detection apparatus. In some embodiments, the pump can be an integral component of the detection apparatus such that the pump is coupled to the reagent cartridge during (or after) coupling the reagent cartridge to the detection apparatus.

Optionally, the reagent cartridge can include a waste reservoir and the series of fluidic components in the main channel can further include a waste valve that connects the waste reservoir to the main channel at a position that is between the first reservoir valve and the first pump valve. Under this option, step (c) can further include opening the waste valve, thereby moving fluid from the flow cell to the waste reservoir. Additionally, under this option step (d) can further include opening the waste valve, thereby moving fluid from the flow cell to the waste reservoir.

The cyclic reaction that occurs in the method can be a nucleic acid sequencing reaction, a nucleic acid synthesis reaction, a peptide sequencing reaction, peptide synthesis reaction, combinatorial small molecule synthesis reaction or the like. The cyclic reaction can occur for these or other types of analytes that are optionally attached to a surface in the flow cell. In some embodiments, the analytes can produce fluorescent signals that are optically detected in the method.

In particular embodiments, the method can include steps of amplifying nucleic acids in or on the flow cell. Accordingly, amplification reagents can be delivered to the flow cell from reservoirs in the reagent cartridge.

BRIEF DESCRIPTION OF THE DRAWINGS

FIG. 1F shows a cutaway view of the fluidic cartridge along section A-A in FIG. 1E.

FIG. 2B shows a bottom/rear perspective view of the body component;

FIG. 10A shows a valve actuation schedule for a solid-phase DNA amplification reaction.

FIG. 10B shows a valve actuation schedule for a cycle of a Sequencing By Binding™ reaction.

DETAILED DESCRIPTION

Figure 1A:
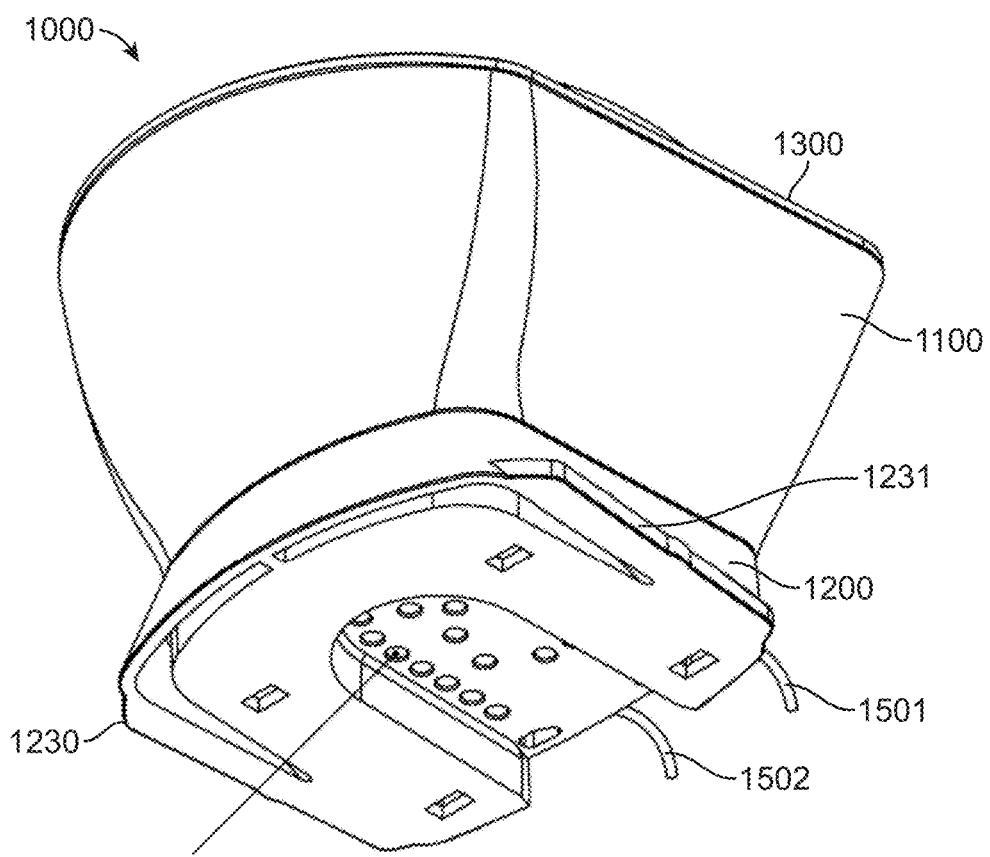
FIG. 1A shows a bottom/front perspective view of a fluidic cartridge.

The present disclosure provides apparatus and methods for performing chemical and biological reactions. Particularly useful reactions are repetitive reactions such as those used to characterize or synthesize polymers. A wide variety of polymers exist in nature and an infinite variety of polymers can be made by natural processes, or synthetic processes, using a relatively small number of different monomers. For example, DNA is synthesized in nature from four different nucleotides, as is RNA. Protein, another ubiquitous polymer, is made from 20 different genetically encoded amino acids. Apparatus and methods of the present disclosure can be configured to serially deliver a relatively small number of different reagents to synthesize or characterize a wide variety of polymers. For example, nucleic acids can be sequenced by serially delivering reagents that specifically react with the four different types of nucleotide monomers and detecting the products of each reaction. Alternatively, nucleic acids can be synthesized by serially delivering one of four different nucleotide monomers, or precursors thereof, in a predefined order to a growing polymer. Proteins can also be sequenced or synthesized using serial delivery of amino acid monomers or reagents that react with the monomers. Thus, a relatively small number of reagents can be repetitively delivered in an apparatus or method set forth herein to synthesize and or characterize a large variety of polymers.

In particular embodiments, an analytical apparatus is provided. The analytical apparatus includes, inter alia, a fluidic system for managing reagents and a detection system for detecting reaction products. The fluidic system can be provided in a cartridge component that interacts with a detector that is housed in a detection instrument. As such, the cartridge can function as a "wet" component that interacts with a "dry" instrument. An advantage of having separate components is that the cartridge can be dedicated to a particular reaction, and when the reaction is complete the cartridge can be removed from the detection instrument and replaced with a new cartridge dedicated to a second reaction. Because the reagents and reaction products for each of these two reactions are physically separated from the detection instrument, cross contamination between the reactions, that would otherwise cause detection artifacts, are avoided.

The physical separation of the components provides a further advantage of avoiding unnecessary detection instrument downtime if the fluidic component experiences mechanical difficulties. Specifically, unlike many commercially available detection instruments which have permanently integrated fluidics, a fluidic system failure can be conveniently overcome by merely removing a faulty fluidic cartridge and replacing it with another so that the detection instrument experiences little to no downtime. In some embodiments, the cartridge is disposable, for example, being made from relatively inexpensive components. The cartridge can be configured in a way that reagents are sealed in the cartridge thereby avoiding unwanted contamination of the environment and unwanted exposure of laboratory personnel and equipment with the reagents. Alternatively, the fluidics cartridge can be emptied, refilled and re-used if desired for a particular application.

In some embodiments, a fluidic cartridge of the present disclosure includes not only reagent reservoirs, but also includes one or more waste reservoirs. Reagent that is not consumed in a reaction step and/or unwanted products of a reaction can be collected in the waste reservoir. Alternatively or additionally, to the use of waste reservoirs, spent reagents can be collected in a reagent reservoir that is no longer needed, for example, having been emptied of needed reagent. This is possible because the fluidic system can be easily configured to move reagents out of reagent reservoirs and into the reagent reservoirs. Thus, reagent reservoirs can be used instead of a waste reservoir or as supplements to a waste reservoir, as desired. Advantages of retaining pre- and post-reaction fluids in a cartridge include convenience of the user in handling a single fluidic component before and after a reaction is performed, minimizing user contact with chemical reagents, providing a compact footprint for the apparatus and avoiding unnecessary proliferation of fluid containers.

Several embodiments of the apparatus and methods of the present disclosure are exemplified for a fluidic cartridge that interacts transiently with a detection component. It will be understood that a fluidic system and detection system having features set forth herein need not be separable. As such, an integrated analytical apparatus can include one or more of the features, and resulting advantages, set forth herein.

A fluidic cartridge of the present disclosure can include a main channel and the ends of the main channel can be connected to the ends of a flow cell to form a fluidic loop. Reservoirs typically housed on the cartridge (but in some cases located external to the cartridge) can connect to the fluidic loop. For example, individual reservoirs can be connected to the main channel via an individually actuated valve such that each reservoir can independently communicate fluidically with the flow cell via the fluidic loop. A pressure source can be connected to the fluidic loop to provide positive and/or negative pressure to the fluidic system. The combined effect of the loop configuration, individually actuated valves for each reservoir and two-way pressure source accommodates a variety of possibilities for multistep reactions. Reagents can move, not only from individual reservoirs to the flow cell, but also from one reservoir to another. In some embodiments, reagents can be re-used in a format where reagent is delivered to the flow cell for a first reaction, unused reagent is then sent back to the reservoir (or collected in a cache reservoir), and then the unused reagent is sent back to the flow cell for a second reaction. Thus, a fluidic system set forth herein can provide an advantage of supporting convenient re-use of relatively expensive or scarce reagents.

In particular embodiments, a fluidic loop is configured to move fluids through a flow cell in either of two directions. For example, a first set of reservoirs can connect to the fluidic loop at a position that is proximal to one end of the flow cell and a second set of reservoirs can connect to the fluidic loop at a position that is proximal to the other end of the flow cell. Reagents that are likely to participate in undesirable side reactions with each other can be present in reservoirs on opposite sides of the flow cell and delivered to the flow cell from the respective proximal ends to minimize the opportunity for the unwanted side reactions. Moreover, one of the reagents can be removed from the channel through the end it was delivered. Because the reagent enters and exits the same end of the detection channel it does not contact fluidic lines that are used to deliver the other cross-reactive reagent (which enters the channel from the other end). Taking the example of a nucleic acid sequencing reaction, blocked nucleotides can be delivered from the first set of reservoirs, and reagents that are intended to reverse the nucleotide blockage only after the nucleotides have been added to a nucleic acid in the flow cell (e.g. deblocking reagent) can be delivered from the second set of reservoirs. The deblocking reagents can be removed from the channel by exiting the same end they entered. In this example, unwanted deblocking of nucleotides in the fluidic lines outside of the flow cell is minimized. This, in turn, minimizes phasing errors that occur when unblocked nucleotides are present in the flow cell during the nucleic acid extension step of the sequencing reaction.

A further advantage of embodiments that use a fluidic loop as set forth herein is that dead volumes, which are proportional to the length of the fluidic lines between reservoirs and flow cell, can be minimized. This provides an advantage of reducing the volume of reagent needed for each step, an advantage that increases in importance for cyclic reactions where dead volume losses accumulate in proportion to the number of cycles of reagent delivery performed. Lower dead volumes also generally results in a faster overall reaction time for a cyclic reaction.

In some embodiments, a pressure source can be connected to the main channel via a branch channel that is also connected to a priming reservoir. An advantage of this configuration can be exemplified for systems that use a syringe pump as a pressure source. In this configuration, the syringe can be primed with fluid from the priming reservoir fluid at the beginning of a fluidic operation. Fluids from other reservoirs need not be pulled into the syringe barrel at any point during use. Avoiding the need to pull reagents into the syringe barrel not only minimizes the number of pump and valve actuations, which in turn reduces time and power requirements for the fluidic operations, but also avoids risk of cross contamination and need for high wash volumes. Specifically, cross contamination is avoided because different reagents do not enter the syringe barrel and, as a result, large wash volumes are not needed to flush the syringe barrel throughout use. By removing the syringe barrel from the fluid path, an otherwise meso-fluidic system (due to the relatively large volume of the barrel) can function as a truly micro-fluidic system.

An object of the present disclosure is to provide a manifold valve that utilizes an elastomer sheet having one or more magnetically actuated components. The elastomer sheet can be sandwiched between two solid supports to provide a plurality of diaphragm valves that control the flow of fluid through one or more channels on the first substrate. In particular embodiments, the diaphragm valves are normally closed, being opened by applying a magnetic force to pull the magnetically actuated component(s) toward the second solid support, which in turn pulls the elastomer sheet away from the one or more channels on the first substrate.

For example, a plurality of magnetic pistons can be attached to the elastomer sheet and the magnetic pistons can be pulled through shafts in the second solid support to open the normally closed diaphragm valves.

The details of one or more embodiments are set forth in the accompanying drawings and the description below. The drawings and description are provided as examples for purposes of explanation and are not necessarily intended to limit the scope of the invention. The invention is susceptible to modifications in the methods and materials, as well as alterations in the fabrication methods and equipment. Such modifications will become apparent to those skilled in the art from a consideration of the drawings and the description below.

FIG. 1A is a perspective view of a fluidic cartridge 1000 that shows a body component 1100 attached to a foot component 1200. The body component houses a plurality of internal reservoirs that are covered by a lid 1300. The foot component 1200 includes wings 1230 and 1231 that can interact with a clamp or slot in a detection apparatus to removably couple the cartridge with the detection apparatus. Also shown are fluidic lines 1501 and 1502 that can connect to a flow cell or other fluidic component that will be in fluidic communication with the reservoirs.

A cartridge of the present disclosure can be made from any of a variety of materials. Particularly useful materials are plastics such as polypropylene, polycarbonate, polystyrene, thermoplastic elastomers or the like. Other useful materials include non-ferromagnetic metals, glass, ceramic or the like. Rigid materials that retain fluids are particularly desirable. Furthermore, materials that are inert to fluid reagents used in a particular application are also desired. The cartridge and other components set forth herein can be made by known manufacturing methods such as injection molding, heat sealing and ultrasonic welding. Magnetic pistons can be integrated into a diaphragm component by methods such as insert molding, snap fit and bonding. Magnetic pistons can be made by known methods, such as cold forming or machining.

Figure 1B:
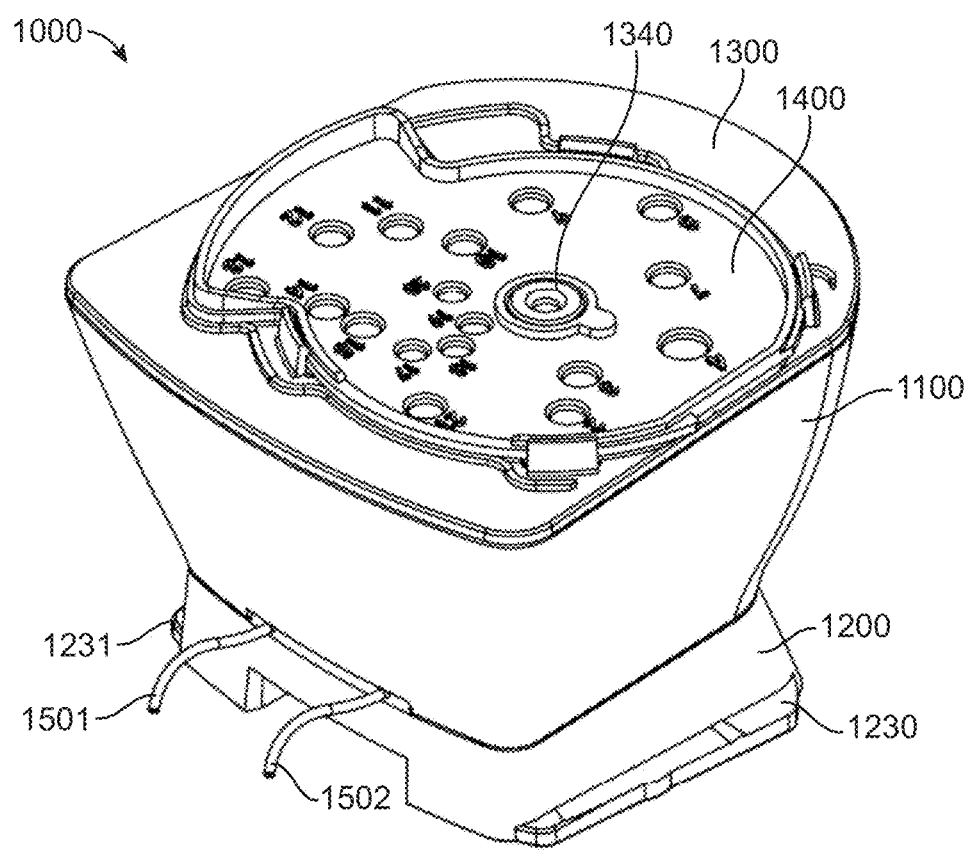
FIG. 1B shows a top/rear perspective view of the fluidic cartridge.

A top perspective view of fluidic cartridge 1000 is shown in FIG. 1B and shows that lid 1300 includes a rotational closure 1400. Rotational closure 1400 includes a plurality of access holes, numbered 2-21 in the figure, that can be used to access respective reservoirs in body component 1100. The access holes are in the closed configuration in FIG. 1B, but as set forth in further detail below can be opened by clockwise movement of rotation closure 1400 around hub 1340.

Figure 1C:
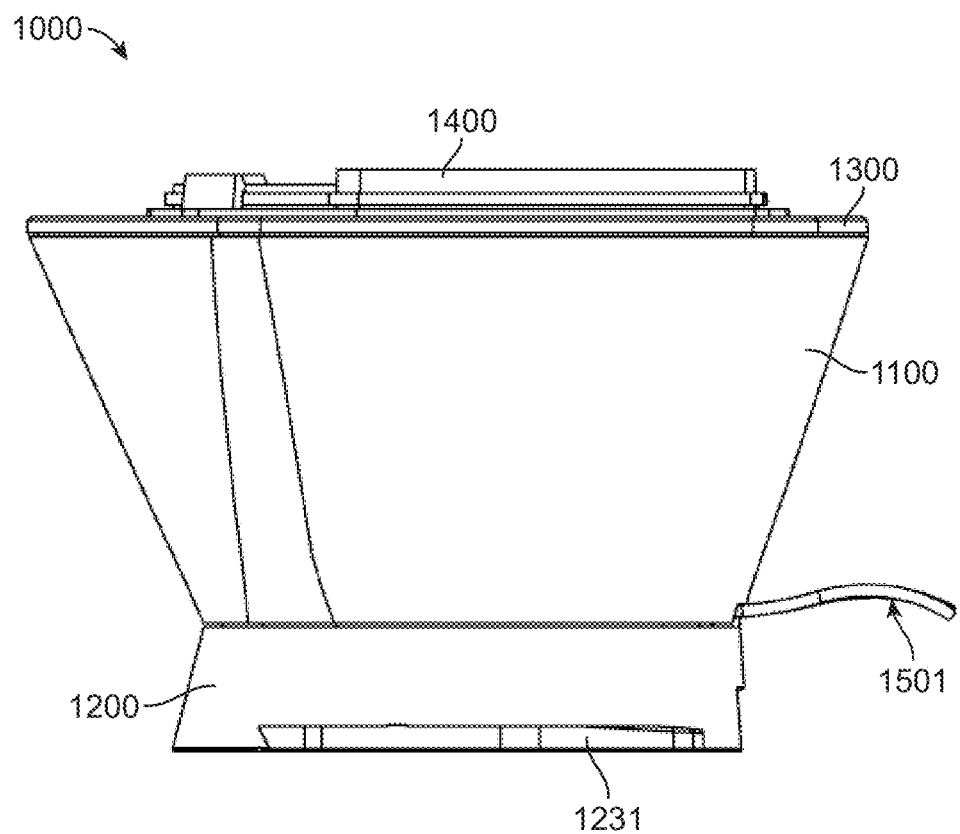
FIG. 1C shows a side view of the fluidic cartridge.
Figure 1D:
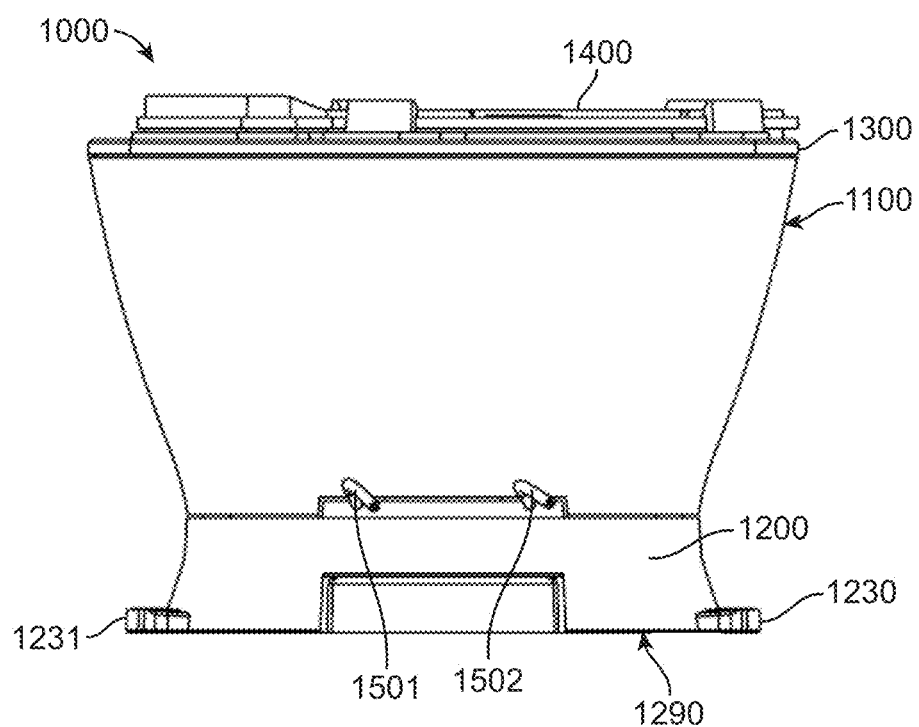
FIG. 1D shows a back view of the fluidic cartridge.

Side and rear views of fluidic cartridge 1000 are shown in FIG. 1C and FIG. 1D, respectively. These views highlight an overall funnel shape for the body component 1100. This shape allows the reservoirs to hold a relatively large volume of reagents, while maintaining relatively low profile for body component 1100 and while maintaining a relatively compact surface area between body component 1100 and foot component 1200. The compact surface area between body component 1100 and foot component 1200 accommodates a valve manifold having a small dead volume. The valve manifold is described in further detail below. A further benefit of the overall shape is convenience for handling the device since the funnel shape reduces the possibility of the cartridge slipping out of the user's hands. The height of cartridge 1000 is roughly 70 mm, the side to side width of lid 1300 is roughly 97 mm, and the front to back width of lid 1300 is roughly 106 mm.

Figure 1E:
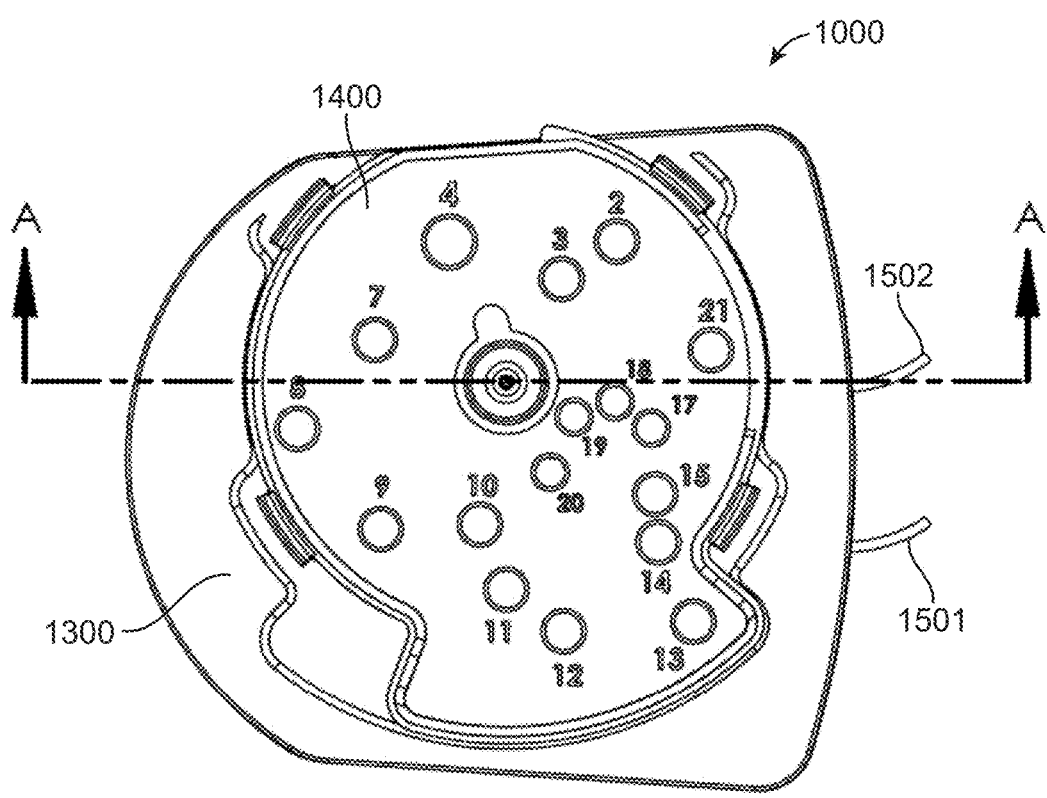
FIG. 1E shows a top view of the fluidic cartridge.
Figure 1G:
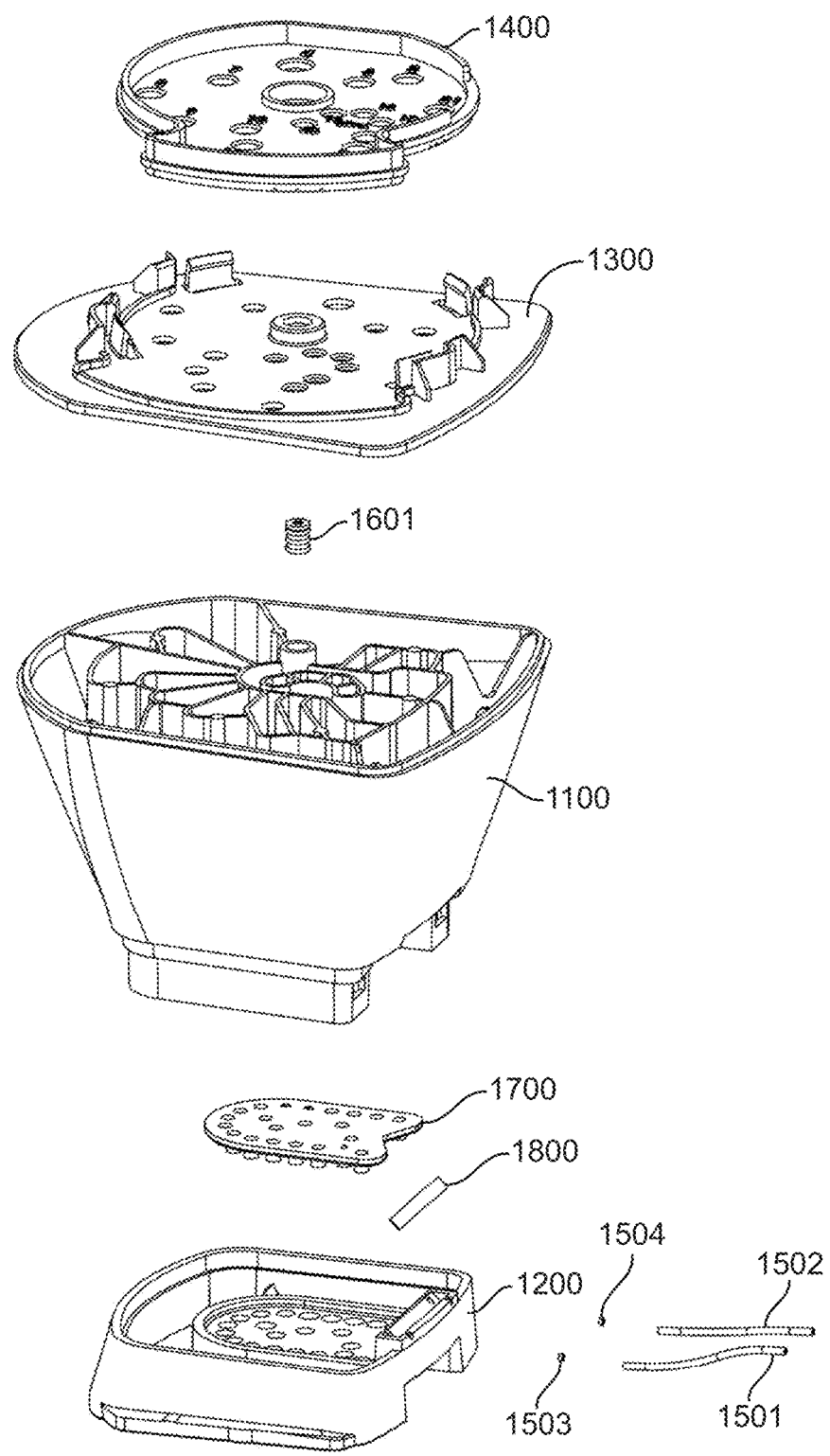
FIG. 1G shows an exploded view of the fluidic cartridge.

A sectional view of cartridge 1000 is shown in FIG. 1F. The section is taken along line A-A in FIG. 1E. Several reservoirs are shown including reservoir 1107, in two sections surrounding reservoir 1108, and reservoirs 1104a, 1103, 1102, 1121 and 1104b. Also shown are syringe pump barrel 1180 and plunger rod 1600. Plunger rod 1600 is attached at the distal end to plunger 1601. The section view also shows a profile of seal 1700, which is sandwiched between body component 1100 and foot component 1200. Seal 1700 includes an elastomer sheet 1770 that is attached to magnetic pistons 1701-1706 which are placed within individual shafts in the foot component. The section also shows metal strip 1800 which is held at an acute angle with respect to the length of tube 1502 that extends out of cartridge 1000. As such, the body component 1100 and foot component 1200 create compression of tube 1502 against metal strip 1800. This compression creates a bite or friction coupling that prevents the tube from being pulled out of cartridge 1000. Strip 1800, need not be made of metal, and can be made from any of a variety of materials having sufficient hardness and compressibility to provide the functional coupling exemplified herein.

Body component 1100 is separable from other components of cartridge 1000 and is shown in isolation in FIG. 2, parts A-F. As shown in FIG. 2A, body component 1100 includes a positioning mechanism for lid 1300 (see FIGS. 1A-1G). The positioning mechanism includes an upper seat 1170 and lower seat 1171 that run along the perimeter of the upper edge of body component 1100. The lower seat 1171 surrounds the outer perimeter of upper seat 1170 to hold the lid in place and prevent the lid from sliding off. Of course, a positioning mechanism can be made in other configurations, for example, with an upper seat that surrounds the outer perimeter of a lower seat, and/or with a discontinuous upper seat.

The bottom perspective view of body component 1100 in FIG. 2B shows elements that are used to connect to foot component 1200. The elements include a flange 1173 that surrounds three sides of a flat surface 1172. The flange has an overall horseshoe shape and supports four snap windows 1174a-1174d, which couple with four foot component snaps 1275a-1275d (see FIGS. 3A-3E). The coupling of the four snap windows 1174a-1174d with four foot component snaps 1275a-1275d produces a compression between the body component 1100 and foot component 1200. Holes 1190 and 1191 are positioned to accept tubes 1501 and 1502, respectively. The holes flank wedge shaped flange 1192 which is positioned to retain metal strip 1800 at an acute angle as set forth above.

Figure 2A:
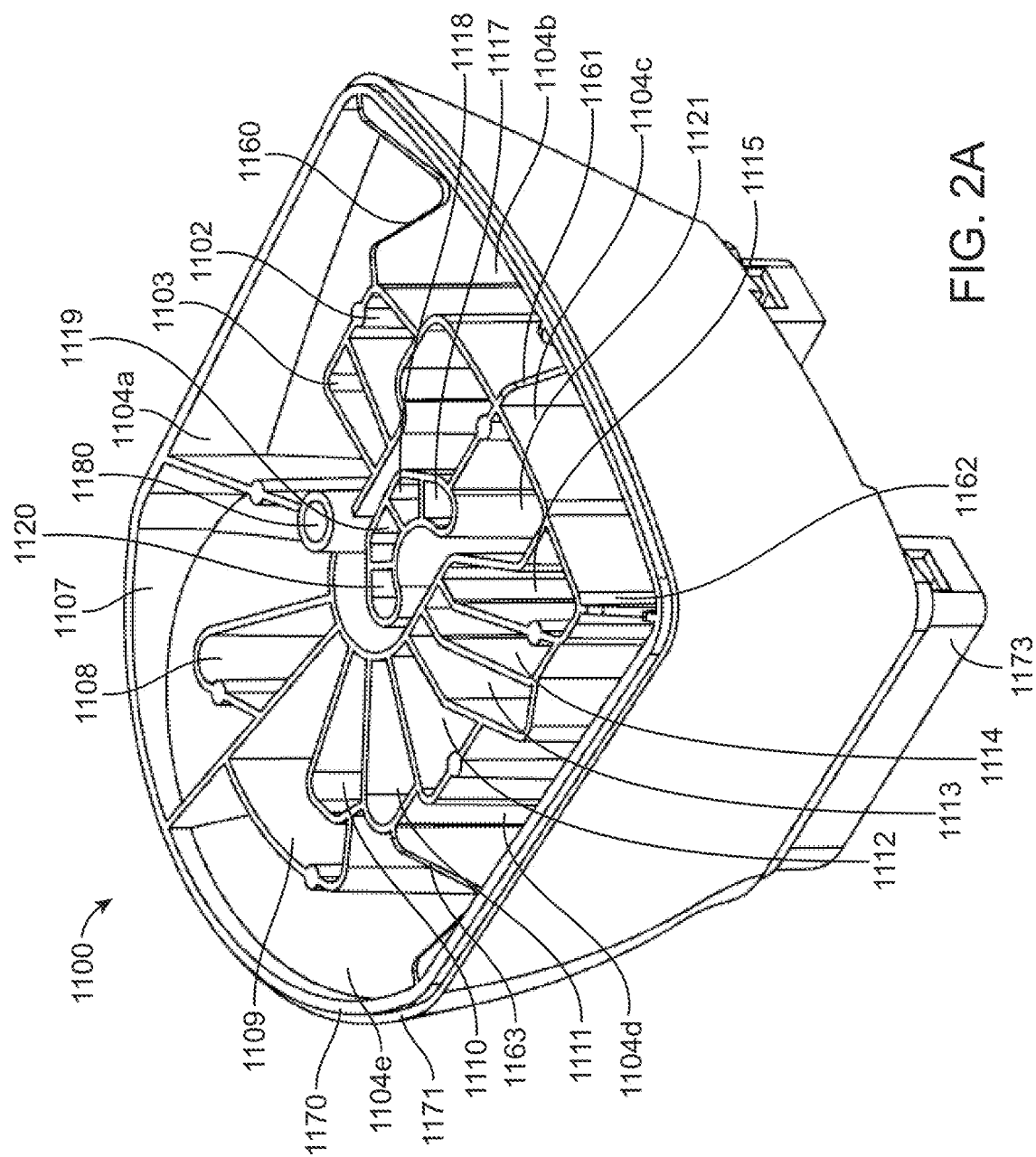
FIG. 2A shows a top/rear perspective view of a body component of a fluidic cartridge.
Figure 2C:
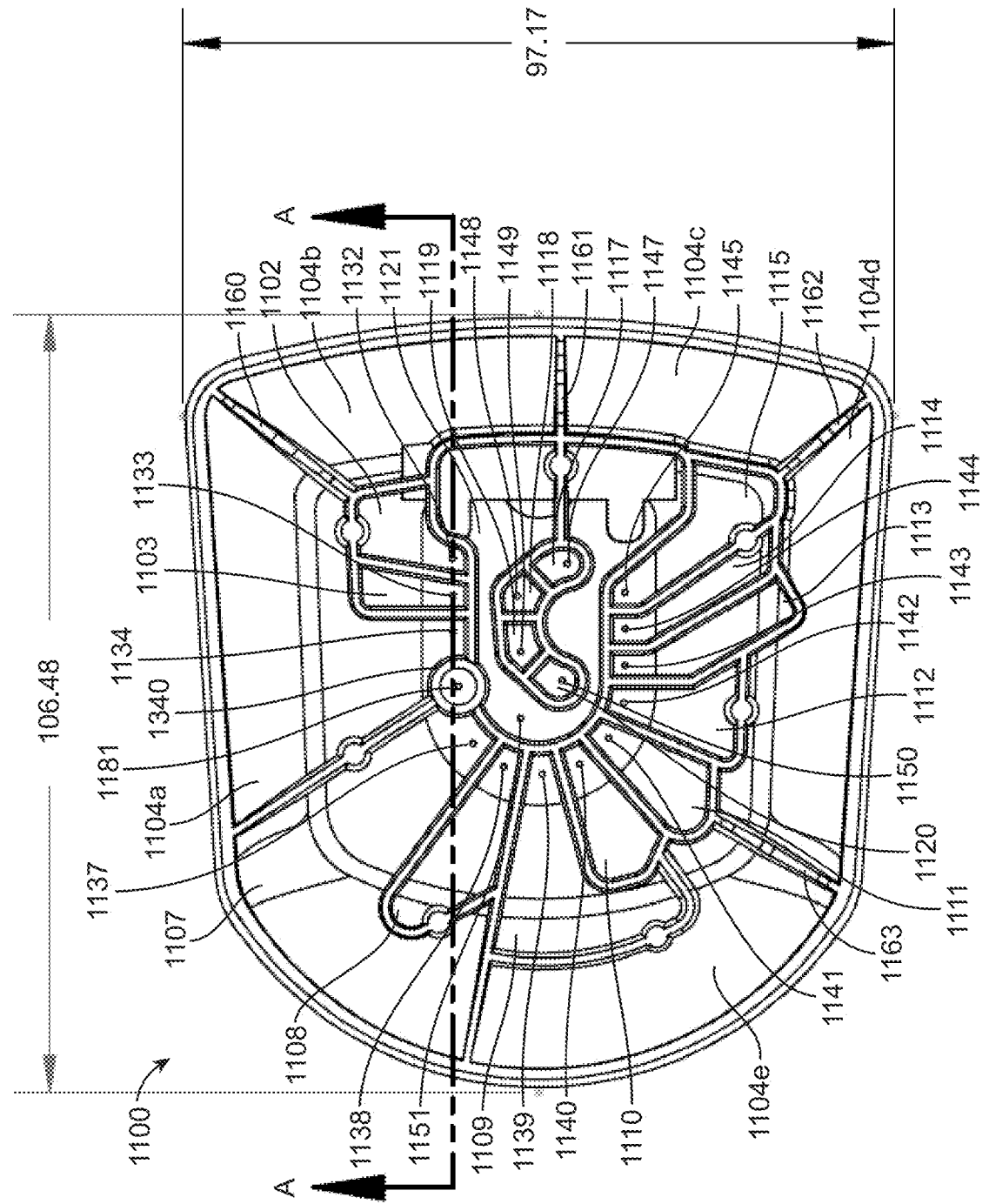
FIG. 2C shows a top view of the body component.
Figure 2D:
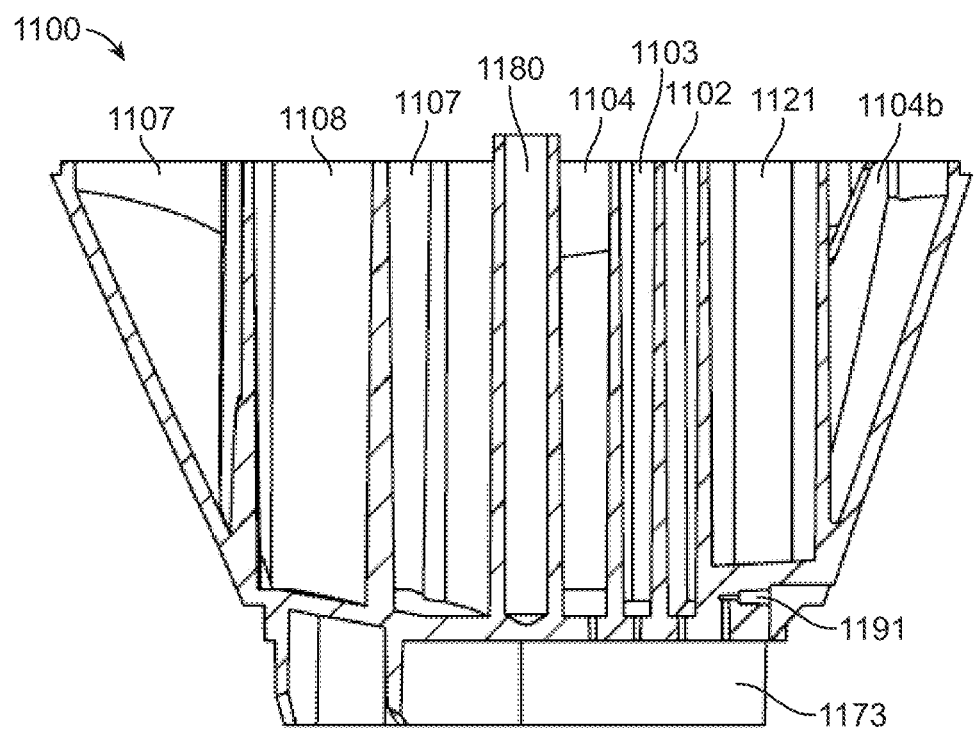
FIG. 2D shows a cutaway view of the fluidic cartridge along section A-A in FIG. 2C.

FIG. 2C is a top view of body component 1100, which is open to show a plurality of reservoirs within. The plurality of reservoirs includes a first subset of reservoirs that can be used for sequencing reagents (reservoirs 1102, 1103, 1107-1115 and 1121), a second subset of reservoirs that can be used for solid-phase amplification of nucleic acids (reservoirs 1117-1120) and a third subset of reservoirs that can be used to collect waste (reservoirs 1104a-1104e). There is flexibility regarding the volume and spatial arrangement of the reservoirs, for example, to accommodate different reactions and reagents. An advantage of the arrangement exemplified in the figures is that each of the reservoirs in the first subset has a dedicated valve opening (valve openings 1132, 1133, 1137-1145 and 1151) and the valve openings are positioned to fluidically communicate with a main channel M that forms a loop when connected to a flow cell. In the arrangement shown, each of the reservoirs in the second subset also has a dedicated valve opening (valve openings 1147-1150), and the valve openings are positioned to fluidically communicate with a branch channel B that connects with the main channel M. Further details of the valves, main channel M, branch channel P, and branch channel B are set forth below.

Waste reservoirs 1104a-1104e fluidically communicate with main channel M via valve opening 1134. Waste reservoirs 1104a-1104e are separated from each other by dams 1160, 1161, 1162 and 1163, but each of the dams has a spillover. The spillovers can be notches in the top of the dams as visible in FIG. 2A. Accordingly, waste that enters valve 1134 will first fill reservoir 1104a to capacity until fluid spills over dam 1160 into reservoir 1104b, followed by the fluid spilling over dam 1161 to reservoir 1104c, then fluid spilling over dam 1162 to reservoir 1104d and then fluid spilling over dam 1163 to reservoir 1104e to fill the waste reservoir system. The waste reservoir system can accommodate a volume that is greater than or equal to the sum of the volumes of all reservoirs in cartridge 1000. In the exemplary cartridge shown the waste reservoirs are located in the outer perimeter of the body component; however, other arrangements are possible. The dams in the reservoir system provide a function of lending structural support to maintain rigidity of cartridge 1000.

FIG. 2C also shows barrel 1180 which interacts with plunger rod 1600 which is in turn driven by a linear actuator. Barrel 1180 communicates with the main channel M via valve opening 1181. As shown in the sectional view of FIG. 2D, wall 1340 of barrel 1180 extends above the top plane of the rest of body component 1100. The extended wall 1340 provides a hub around which rotational closure 1400 can be moved in order to open and close access to the reservoirs. Wall 1340 also allows the lid to retain the plunger in the cartridge and maintain the cartridge seal. The bottom of the lid can further include two energy directors (small ridges) that are attached to the cartridge body, for example, by an ultrasonic weld.

Figure 2E:
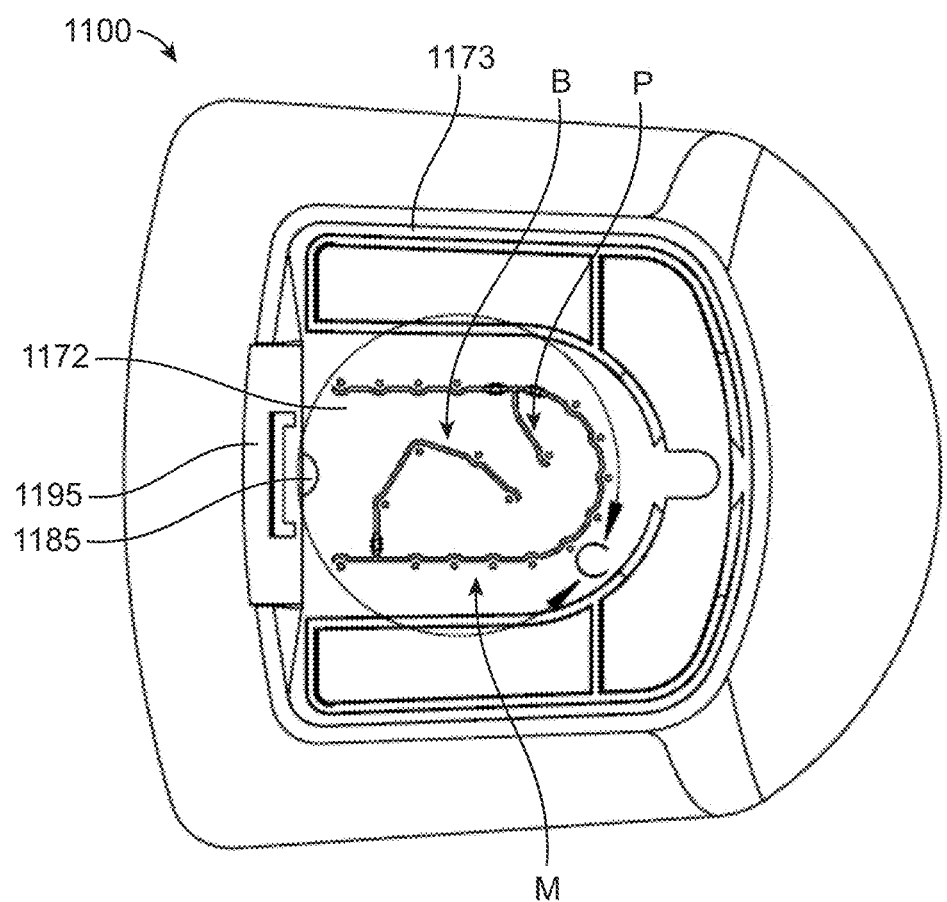
FIG. 2E shows a bottom view of the body component.
Figure 2F:
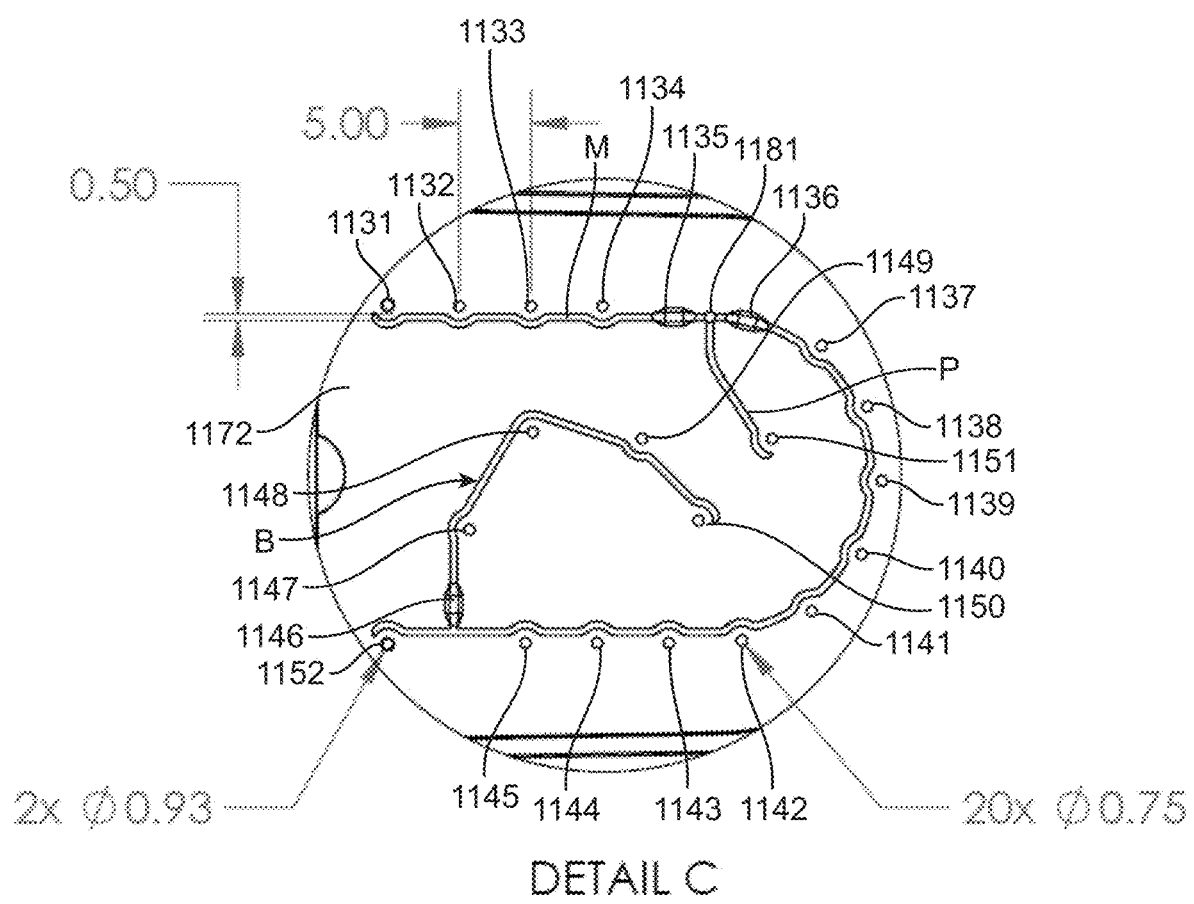
FIG. 2F shows a detail view of section C of FIG. 2E.

The bottom view of body component 1100 shown in FIG. 2E provides a view of channel M that is expanded in FIG. 2F. The main channel M has a u-shaped path and is connected to two branch channels labeled channel B and channel P. The channels form uncovered troughs in surface 1172 when body component 1100 is viewed alone. The channels each have a semicircular cross section with a diameter of 0.5 mm. It will be understood that the channels can have any of a variety of cross sections, for example, a u-shaped, polygonal, square, rectangular or hyperbolic cross section. The channels can have any of a variety of diameters or widths including for example, 1 cm, 8 mm, 6 mm, 4 mm, 2 mm, 1 mm, 0.75 mm, 0.25 mm or less.

Valve openings 1132, 1133, and 1137-1151 have a circular cross section with a diameter of 0.75 mm and pass through the body component 1100 to contact the reservoirs as set forth above in regard to FIG. 2C. Valve openings 1131 and 1152 have a circular cross section with a diameter of 0.93 mm and connect to tubes 1502 and 1501, respectively. The valve openings 1131-1133 and 1137-1152 are positioned adjacent to Channel M, B or P and the channel arcs slightly around each opening. This configuration allows elastomer sheet 1770 to be sealed against surface 1172 to form an enclosed tube. As a result, elastomer sheet 1770 not only seals the length of channels M, P and B, but also forms a plurality of diaphragm seals that prevents fluid from passing between the channel and the valve holes. Fluid can be permitted to flow between the channel and a valve hole by pulling a localized portion of the elastomer away from a region of surface 1172 that encompasses the valve hole and the portion of the channel that arcs around the valve hole. Localized portions of the elastomer can be pulled away from surface 1172 in this way using magnetic actuators as set forth in further detail elsewhere herein.

Opening 1181 is placed at the intersection of branch channel P and main channel M. Opening 1181 has a circular cross section with a diameter of 0.75 mm and forms a cylindrical tube that passes through body component 1100 to contact barrel 1180. As such, opening 1181 transfers positive or negative pressure to channel M and channel P due to action of plunger rod 1600 in barrel 1180. Pressure can be regulated in channel M using in-line, main valves formed at dilations 1135 and 1136 that flank opening 1181. Valves are formed at dilations 1135 and 1136 due to nodes 1735 and 1736, respectively, that are located on elastomer sheet 1770 (see, e.g. FIG. 4A). Nodes 1735 and 1736 have a shape that is complementary to dilations 1135 and 1136 such that normally closed valves are created on either side of opening 1181 when elastomer sheet 1770 is pressed against surface 1172. A similar valve is formed by dilation 1146 which is located in channel B where channel B transects channel M. Node 1746, located on elastomer sheet 1770 has a shape that is complementary to dilation 1146 and can block movement of fluids between main channel M and branch channel B when elastomer 1770 is compressed against surface 1172. Valves at dilations 1134, 1135 and 1146 can be opened by pulling a portion of elastomer sheet 1770 to pull out nodes 1735, 1736 and 1746, respectively. The portions of elastomer sheet 1770 can be pulled away from surface 1172 in this way using magnetic actuators as set forth in further detail below. The elongated polygon shape of the node is exemplary. Any of a variety of node shapes can be used to suit a particular channel aperture shape.

Figure 3A:
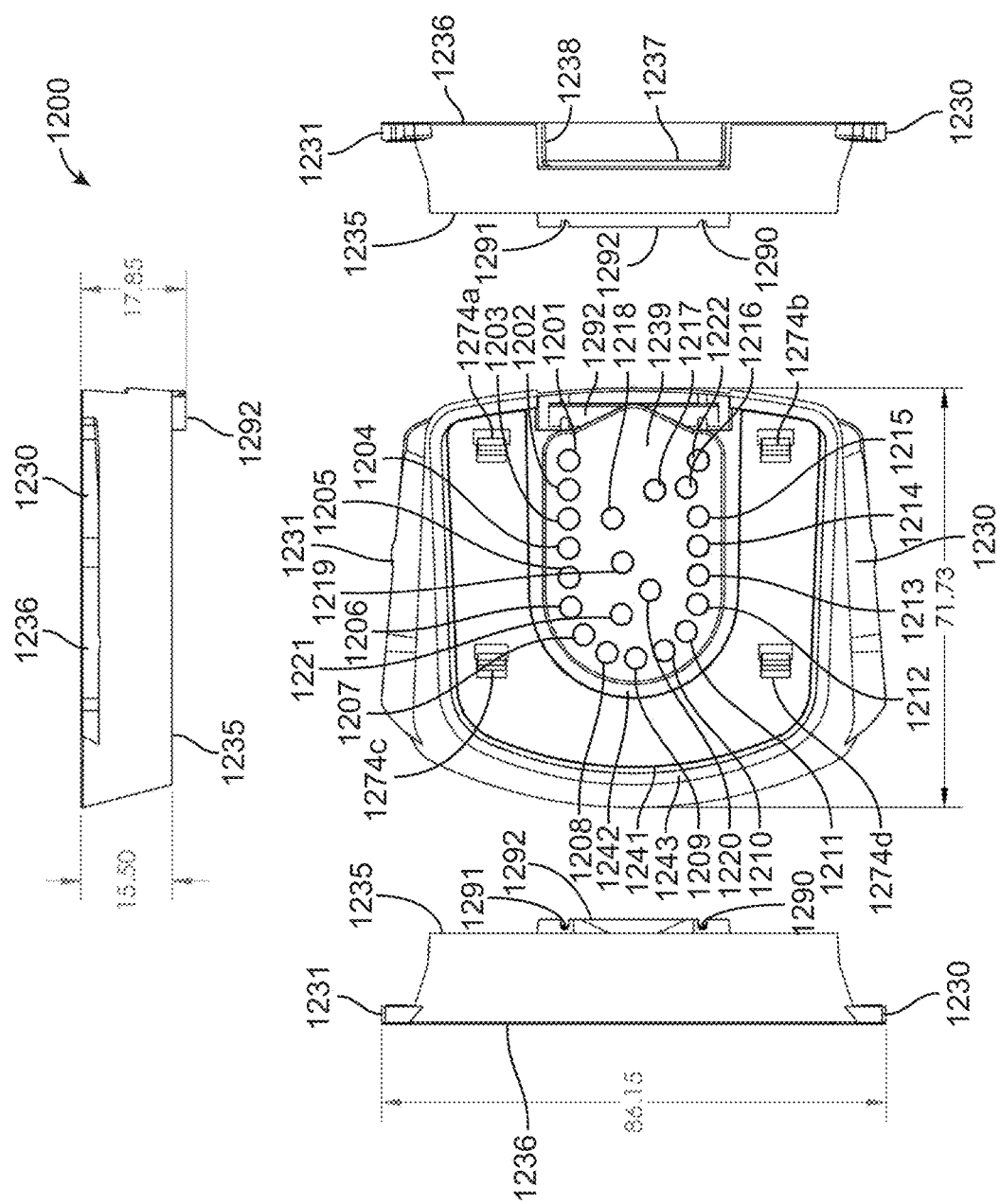
FIG. 3A shows a top view of a foot component of a fluidic cartridge surrounded by three respective side views.
Figure 3B:
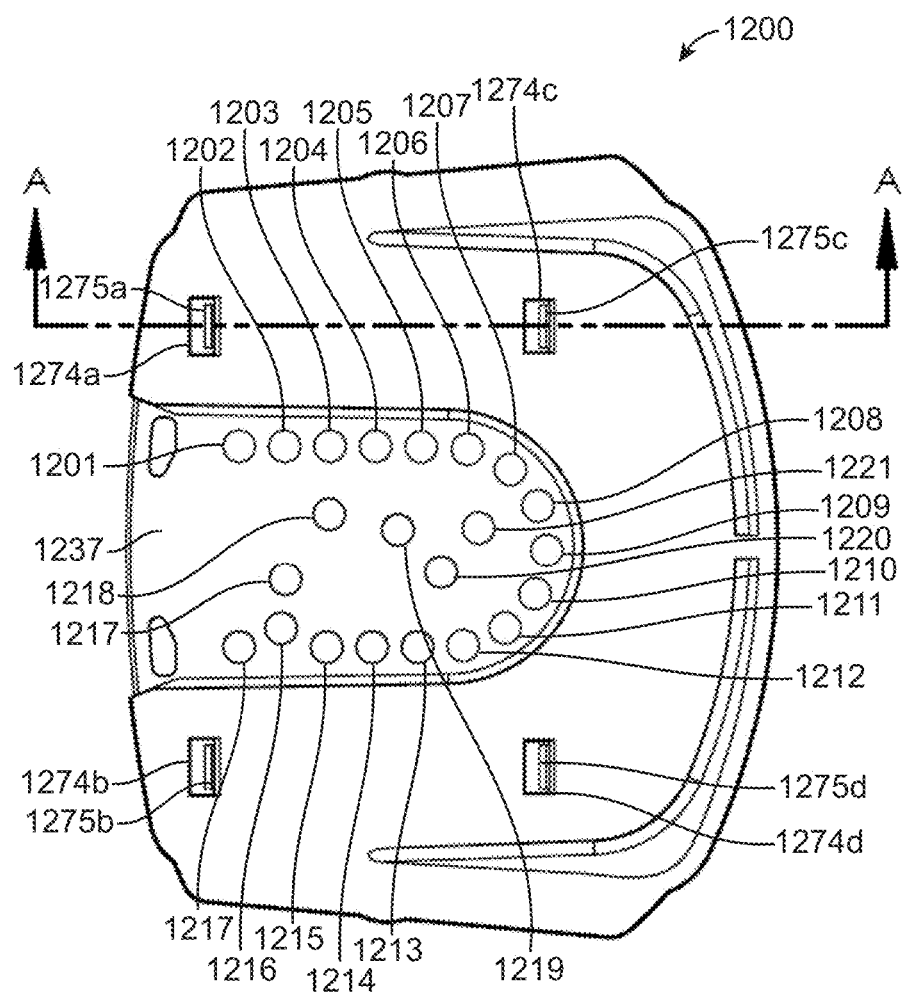
FIG. 3B shows a bottom view of the foot component.
Figure 3C:
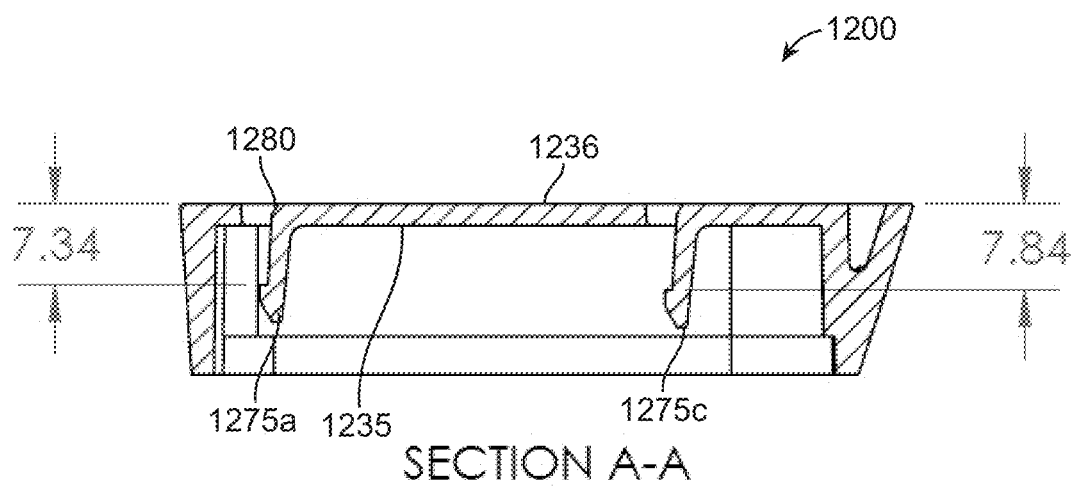
FIG. 3C shows a cutaway view of the foot component along section A-A in FIG. 3B.
Figure 3D:
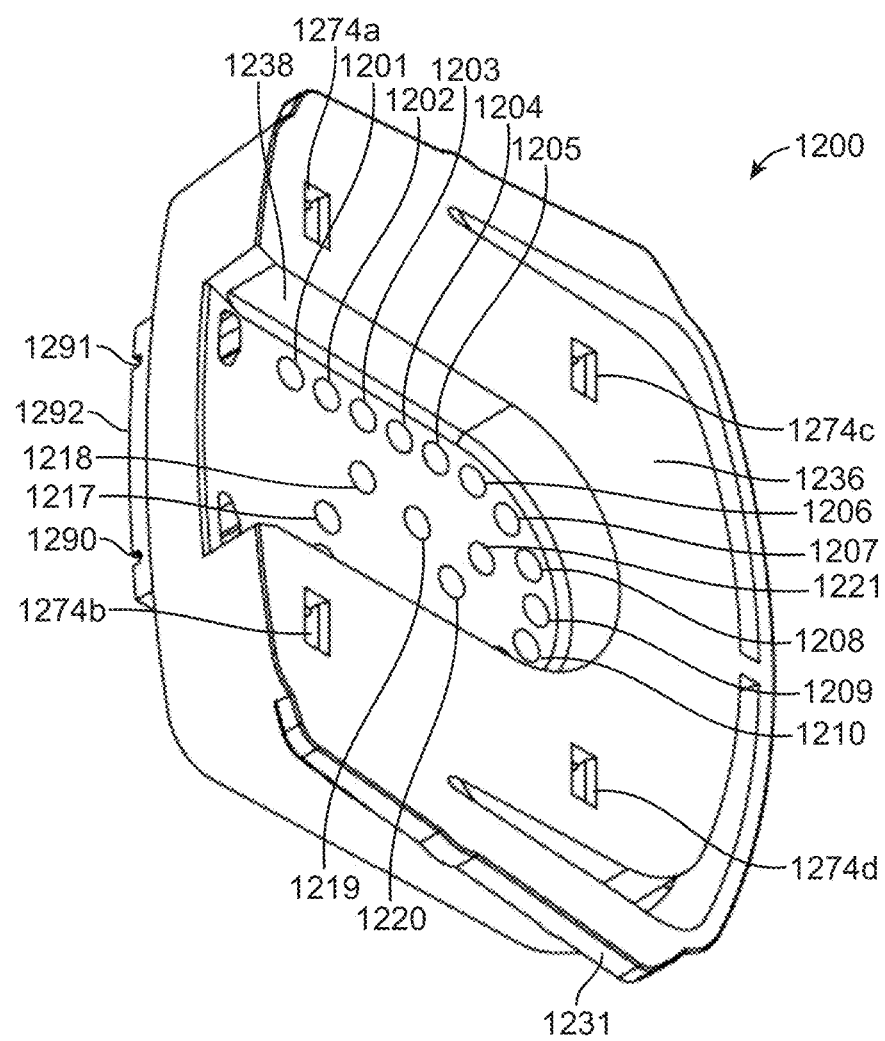
FIG. 3D shows a bottom/rear perspective view of the foot component.
Figure 3E:
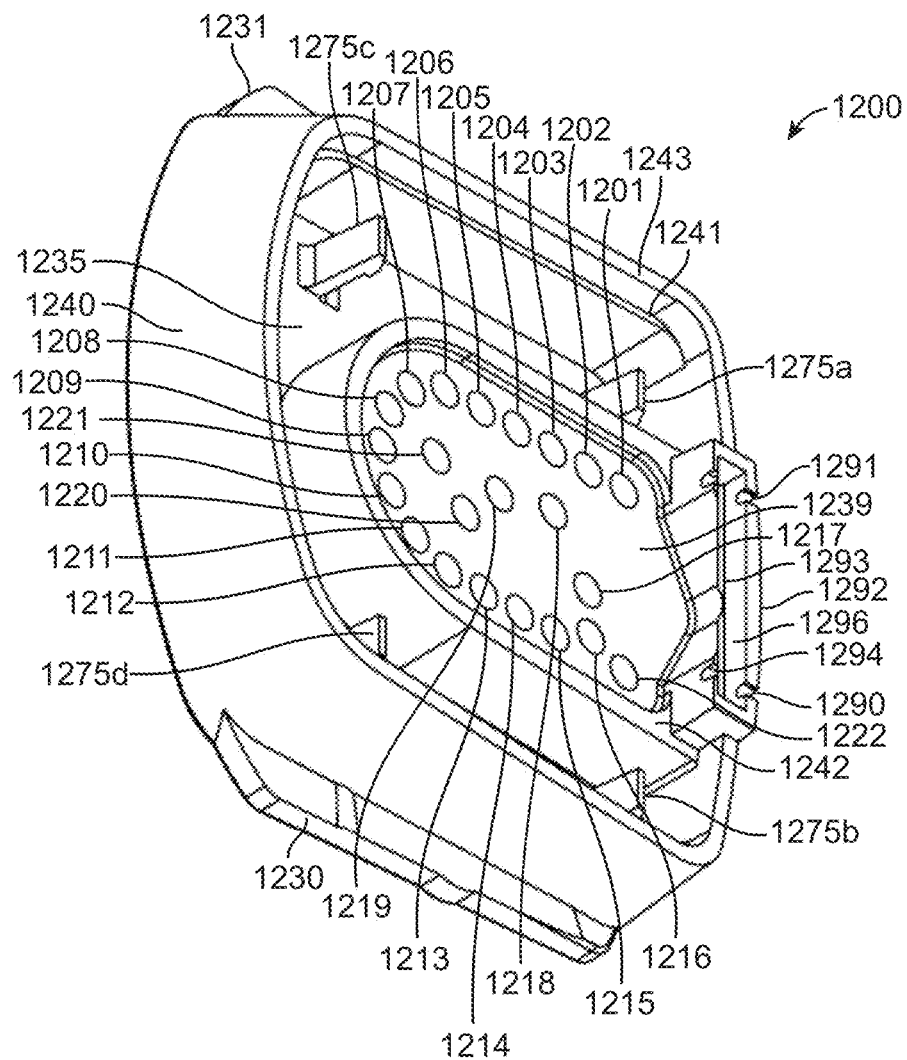
FIG. 3E shows a top/front perspective view of the body component.

As shown in FIG. 3A and FIG. 3E, foot component 1200 includes several features that cooperate to connect with body component 1100. Snaps 1275a-1275d on foot component 1200 can make a click connection with snap windows 1174a-1174d, respectively, on body component 1100. Snaps 1275a-1275d are attached to foot component 1100 at apertures 1274a-1274d, respectively. The attachment provides a fulcrum supporting a spring-like fore and aft motion of snaps 1275a-1275d with respect to snap windows 1174a-1174d. Exemplary fulcrum attachments 1280 and 1280 are shown for snaps 1275a and 1275c, respectively, in FIG. 3C. Clicking snaps 1275a-1275d to snap windows 1174a-1174d creates compression between foot component 1200 and body component 1100. Under this compression, surface 1235 of foot component 1200 contacts the bottom edge of flange 1173 of body component 1100. The compression also causes upper flange 1243 and lower flange 1241 of foot component 1200 to contact complementary edge surfaces 1193 and 1194, respectively, of body component 1100. The compression also causes flange 1242 of foot component 1200 to contact surface 1172 on body component 1100. This combination of contacts provides lateral alignment of the foot component 1200 with respect to the body component 1100. Generally, it is desired that connection elements provide a contact force between the surfaces on the top of the foot component 1200 and bottom of the body component 1100 that is adequate to flatten seal 1700 and maintain fluid tight diaphragm valves when in the normally closed position. Any of a variety of connection elements can be used in place of snaps that are exemplified herein including, but not limited to, clamps, pressure fittings, threaded couplings or adhesives.

Foot component 1200 includes a feature that cooperates with features of body component 1100 to retain tubes 1501 and 1502 in a desired position. In this position, main channel M is properly connected with a flow cell when cartridge 1000 is assembled. The proximal ends of tubes 1501 and 1502 connect to main channel M via openings 1190 and 1191, respectively, in body component 1100 (see FIG. 2B). When body component 1100 is assembled with foot component 1200, tubes 1501 and 1502 will be accommodated by notches 1294 and 1295 in protrusion 1293 and by notches 1290 and 1291 in protrusion 1292 (see FIG. 3A and FIG. 3E). Protrusions 1293 and 1292 are connected by protrusions 1297 and 1298, thereby defining an internal polyhedral space 1296. The internal space 1296 is configured to maintain a metal strip 1800 to present an upper edge at an elevation above the plane of rim 1243 that is the same as the elevation of notches 1290, 1291, 1294 and 1295 above the plane of rim 1243. Internal space 1296 is also configured to maintain the edge of metal strip 1800 at an acute angle with respect to the length of tubes 1501 and 1502 that extend out of assembled cartridge 1000. As a result, tubes 1501 and 1502 are maintained laterally by the notches and retained in openings 1190 and 1191 (i.e. prevented from being pulled out) by a bite or friction coupling that results when tubes 1501 and 1502 are compressed between the edge of metal strip 1800 and surface 1195 of the body component 1100. A profile view of the coupling for tube 1502 is shown in FIG. 1F.

Shafts 1201-1222 pass through foot component 1200 and are visible in the top view (FIG. 3A) and bottom view (FIG. 3B) of foot component 1200. Shafts 1201-1222 are positioned to accept magnetic pistons 1701-1704, 1707-1715 and 1717-1721, respectively on elastomer sheet 1770 (see FIG. 4B). Magnetic pistons can enter shafts 1201-1222 from the bottom side of foot component 1200 and thus allow individual valve actuation via movement of the magnetic pistons through the shafts. As shown in FIG. 3D, the shafts exit the bottom side of foot component 1200 at surface 1237 which is inset with respect to the bottom foot surface 1236. Accordingly, when foot component 1200 or assembled cartridge 1000 is placed on a support surface (e.g. on a bench top or on a cartridge receiving stage of a detection instrument) the shaft openings are maintained at an elevation above the support surface. Furthermore, bottom foot surface 1236 is horseshoe-shaped, thus providing a means to slide a valve actuation unit into contact with surface 1237 in a way that aligns shafts 1201-1222 with actuators on the actuation unit. Lateral wall 1238 has a height and shape that facilitates the alignment of cartridge 1000 due to complementary fit with the exterior surface of the actuation unit.

FIG. 4 provides several views of a seal that can be compressed between foot component 1200 and body component 1100 when cartridge 1000 is assembled. The seal includes an elastomer sheet 1770 that is attached to a plurality of magnetic pistons 1701-1722. Attachment is mediated by insertion of one end of the magnetic pistons 1701-1722 into the lumen of the elastomer sheet 1770. As a result, each of the pistons protrudes out of the bottom side and produces a convex node on the top side of elastomer sheet 1770. Magnetic pistons 1701-1722 are positioned to protrude into respective shafts 1201-1222 in foot component 1200 when seal 1700 is compressed between surface 1172 of body component 1100 and surface 1239 of foot component 1200. Two types of nodes are present on the top side of elastomer sheet 1770. Nodes 1731-1734, 1737-1745, and 1747-1752 have a circular cross-section that interacts with valve openings 1131-1133 and 1137-1152 when seal 1700 is compressed between surface 1172 of body component 1100 and surface 1239 of foot component 1200. Nodes 1735, 1736 and 1746 have a shape that is complementary to in-line channel dilations 1135, 1136 and 1146 respectively, to form in line master valves when seal 1700 is compressed between surface 1172 of body component 1100 and surface 1239 of foot component 1200.

The top side of elastomer sheet 1770 includes a raised injection molding gate 1760 that fits within guide slot 1185 on body component 1100. The shape of elastomer sheet is complementary to the shape of surface 1172 as defined by the inner surface of flange 1173 on body component 1100. The longest dimension of the seal is roughly 47 mm and the orthogonal dimension is about 30 mm. The combined effect of the complementarity of the shapes is to align pistons with shafts, and to align nodes with valve holes/apertures, when seal 1700 is compressed between surface 1172 of body component 1100 and surface 1239 of foot component 1200.

Figure 4A:
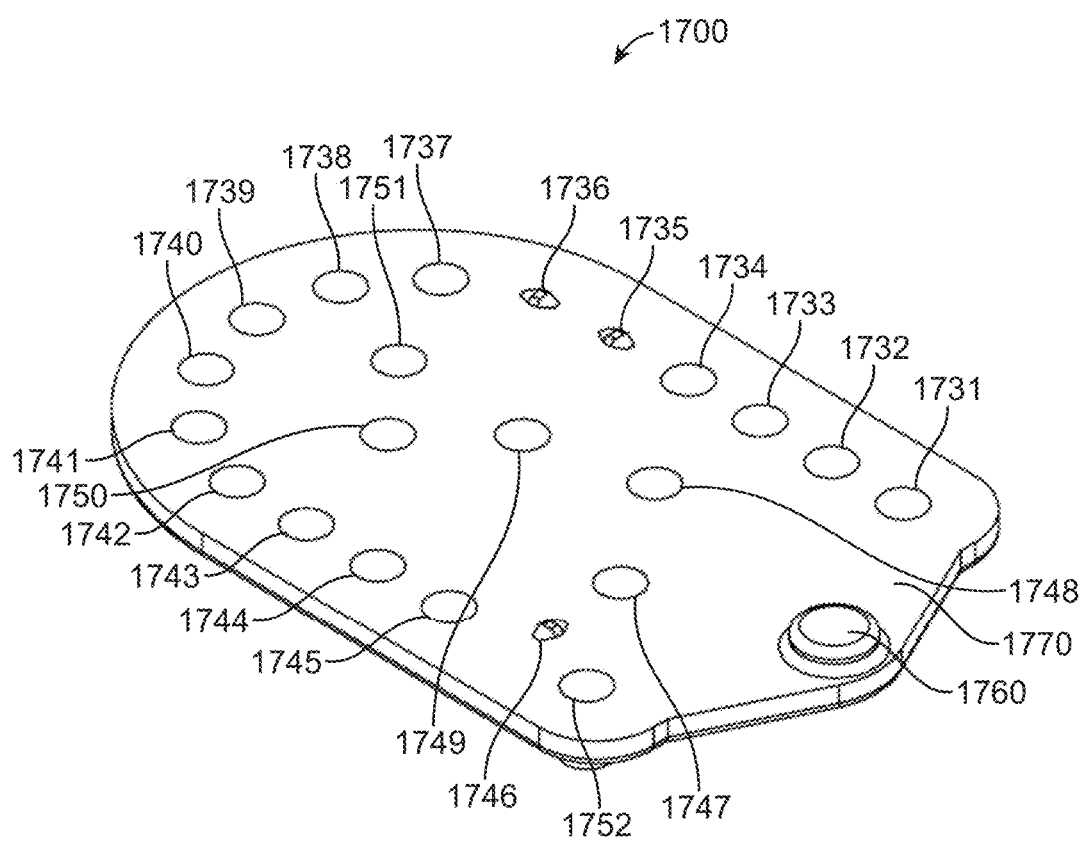
FIG. 4A shows a top/rear perspective view of a diaphragm component of a fluidic cartridge.
Figure 4B:
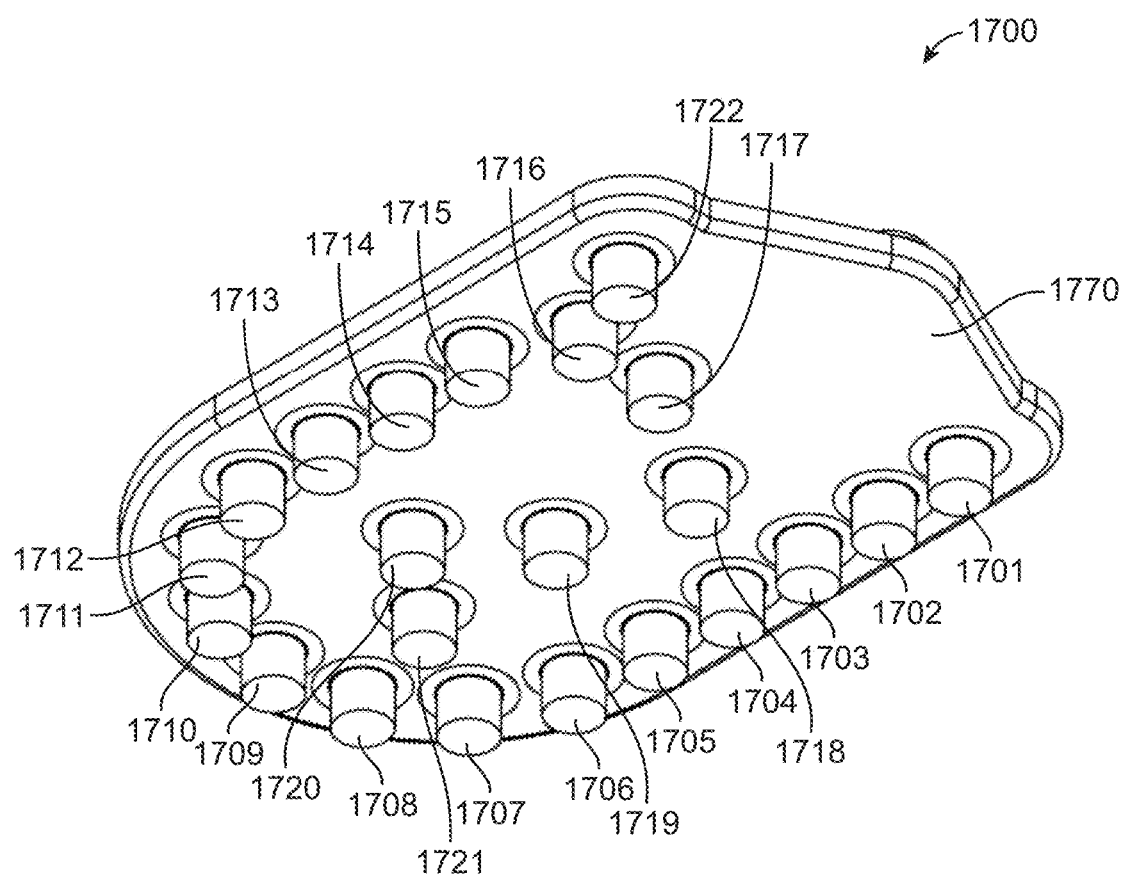
FIG. 4B shows a bottom/rear perspective view of the diaphragm component.
Figure 4C:
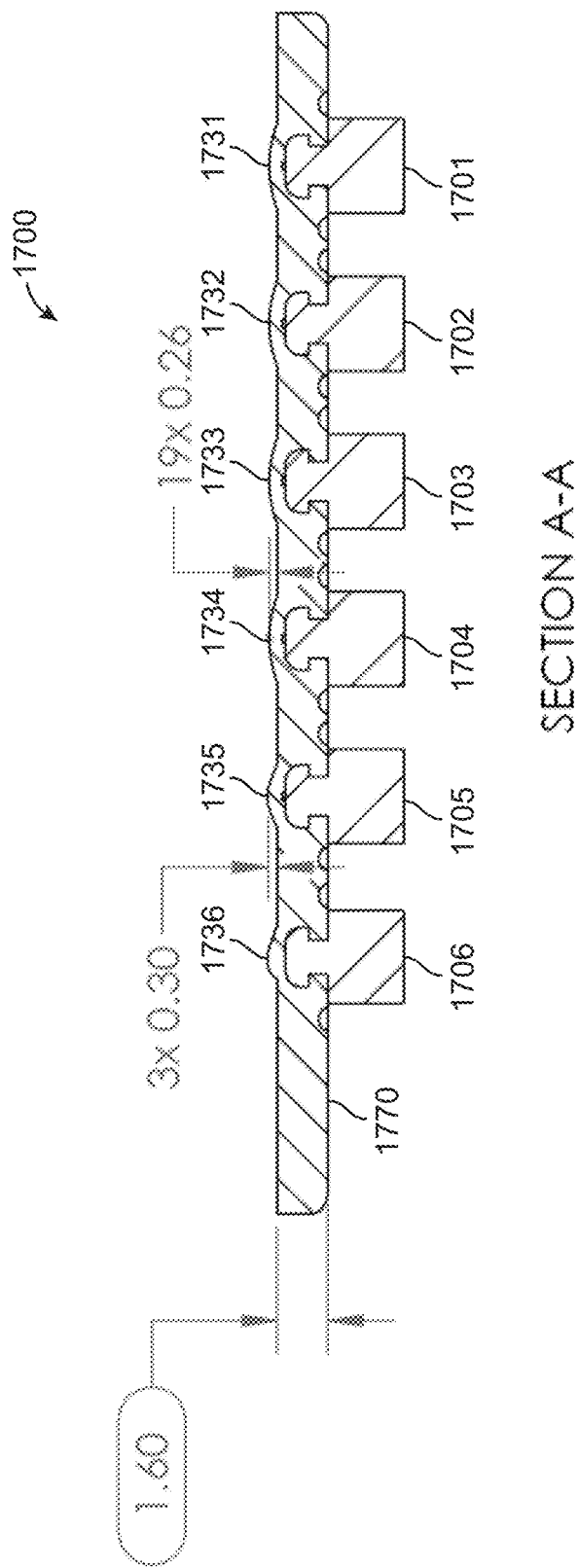
FIG. 4C shows a side view of the diaphragm component.
Figure 12:
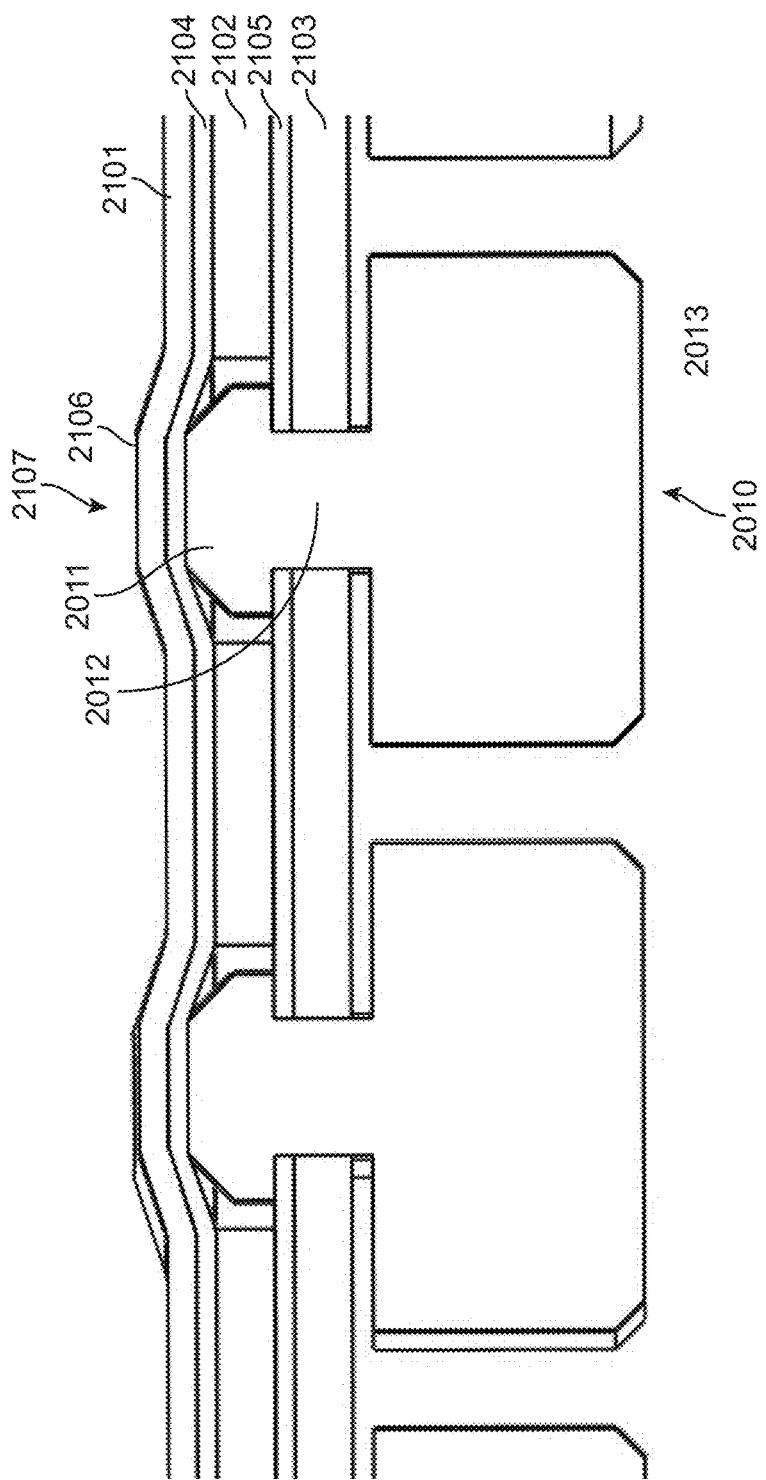
FIG. 12 shows a side view of a multilayered diaphragm component.

The seal exemplified in FIGS. 4A-4C is made from a single elastomer sheet into which the head regions of the pistons are inserted. Preferably, the pistons are insert molded into the elastomer sheet. Alternative configurations can be used to create diaphragm valves having similar function. For example, as shown in FIG. 12, a seal 2100 can include multiple layers of elastomer into which a piston head 2011 is inserted. In this example, three layers of elastomer 2101, 2102 and 2103 are attached to each other via layers 2104 and 2105 of double sided sticky tape. The distal elastomer layer 2103 and distal sticky tape layer 2105 have holes to accommodate the neck 2012 of piston 2010. The piston head 2011 is retained in seal 2100 because the holes are smaller than the head. The middle elastomer layer 2102 has a larger hole that accommodated piston head 2011. The proximal elastomer layer 2101 and sticky tape layer 2104 are continuous and pass over the piston head 2011. As such the top surface 2106 of elastomer layer 2101 can seal an aperture in a cartridge. A node 2107 is formed on the seal because head 2011 has a taller profile than the middle elastomer layer 2102 and the node serves to close an aperture in a fluidic system of a cartridge, thereby forming a diaphragm valve.

Any of a variety of materials can be used for an elastomer layer described herein. A thermoplastic elastomer is particularly useful. Useful types of thermoplastic elastomers include, for example, styrenic block copolymers, thermoplastic olefins, elastomeric alloys, thermoplastic polyurethanes, thermoplastic copolyesters, and thermoplastic polyamides. Specific examples of useful elastomers include, but are not limited to, polyurethane, silicone, natural rubber, Santoprene™ and the like.

Figure 5A:
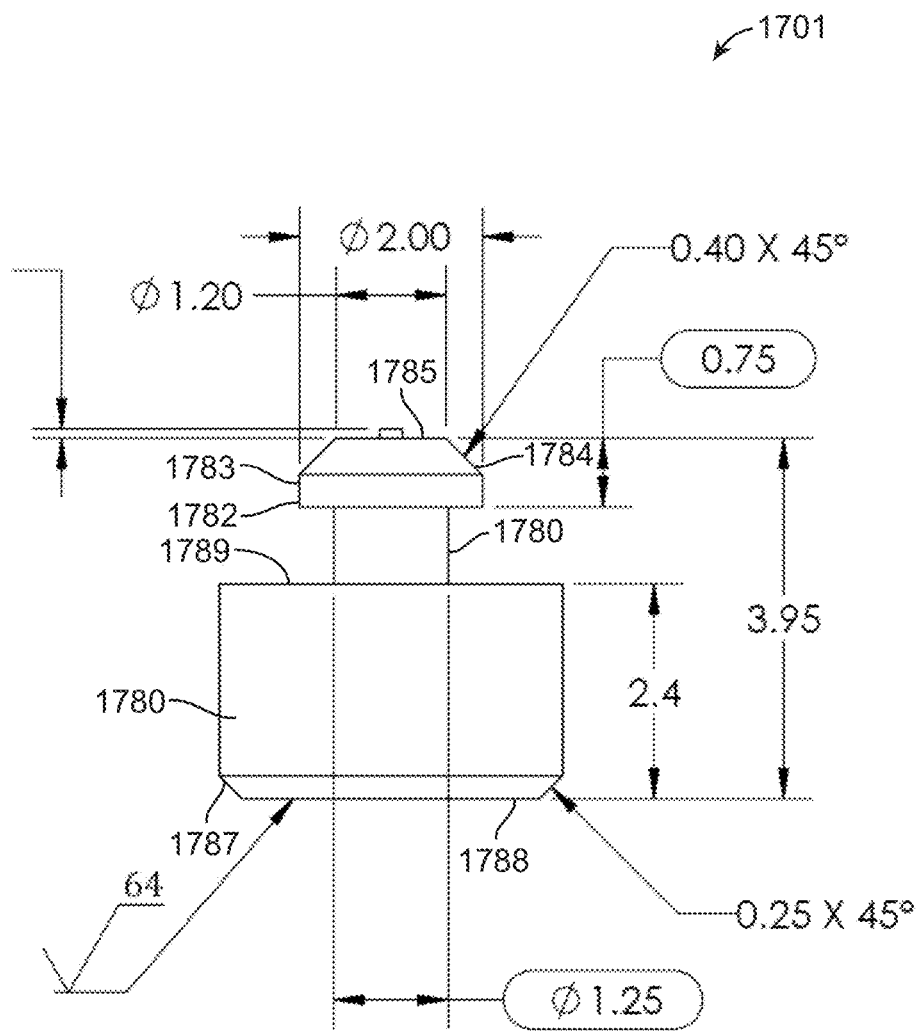
FIG. 5A shows a side view of a magnetic piston of a diaphragm component of a fluidic cartridge.
Figure 5B:
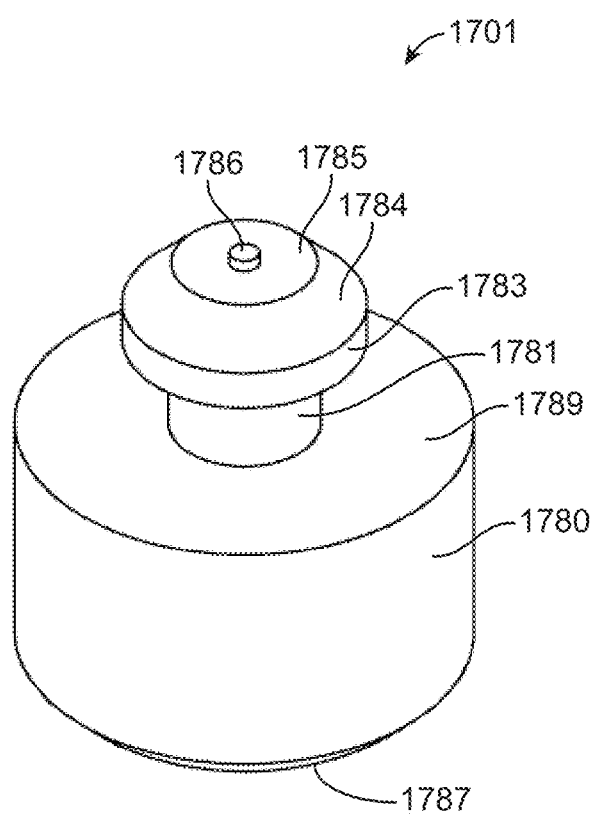
FIG. 5B shows a top perspective view of the magnetic piston.

FIGS. 5A-5B shows an expanded view of piston 1701. The piston has a cylindrical barrel 1780 with a bevel 1787 at the end 1788 that is distal to the end that attaches to elastomer sheet 1770. Bevel 1787 assists with insertion of the piston 1701 into a shaft in foot component 1200. Cylindrical barrel 1780 has a proximal end 1789 that is attached to neck 1781. The other end of neck 1781 is attached to head 1783 which also has a bevel 1784 at end 1785. The head 1783, being wider than neck 1781, and having a square edge 1782, is shaped to be retained in the lumen of elastomer sheet 1770. The top of head 1783 has a protrusion 1786 that functions to create a convex node on the upper side of elastomer sheet 1770. As an alternative to the machined pistons shown in FIG. 5, a fluidic cartridge can include a cold formed magnetic piston that is inserted into an elastomer sheet. Cold forming provides an advantage of reduced costs of manufacture. Cold forming can also convenient for forming a piston having a more rounded body compared to the cold formed pistons.

It will be understood, that magnetic valve actuation of normally closed elastomer valves can be achieved using elements other than pistons. For example, pistons can be replaced with magnetic (or ferromagnetic) elements that are embedded within an elastomeric material in a way that the elements do not protrude outside of the elastomeric material. The elements can be disks that are localized at elastomer nodes. It is also possible to embed a magnetic (or ferromagnetic) material within the elastomeric material without necessarily localizing the material at the nodes. Instead the elastomer is prevented from moving at non-node positions due to compression on the elastomer between the foot 1200 and body 1100 of cartridge 1000.

Figure 6A:
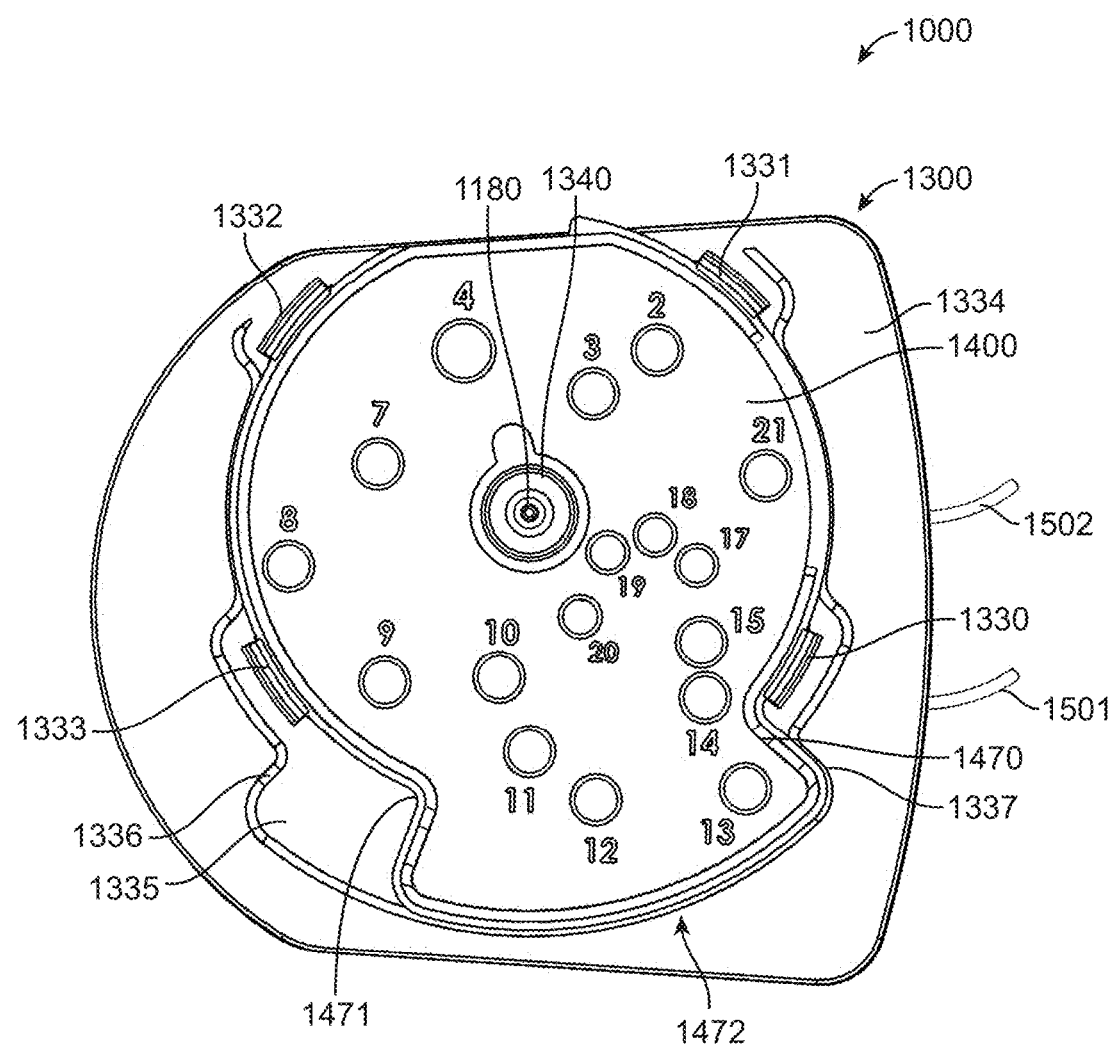
FIG. 6A shows a top view of a closed lid for a fluidic cartridge.

FIG. 6A shows a view of lid 1300 with rotational closure 1400 in the closed position. The access holes 2-4, 7-15 and 17-21 are blocked by surface 1335 in the closed position. Closure 1400 has a handle region 1472 defined by a left side indent 1471 and a right side indent 1470 that provide finger holds for a user. In the closed position the right side of handle region 1472 contacts a stop 1337 on the right side of lid 1300.

Figure 6B:
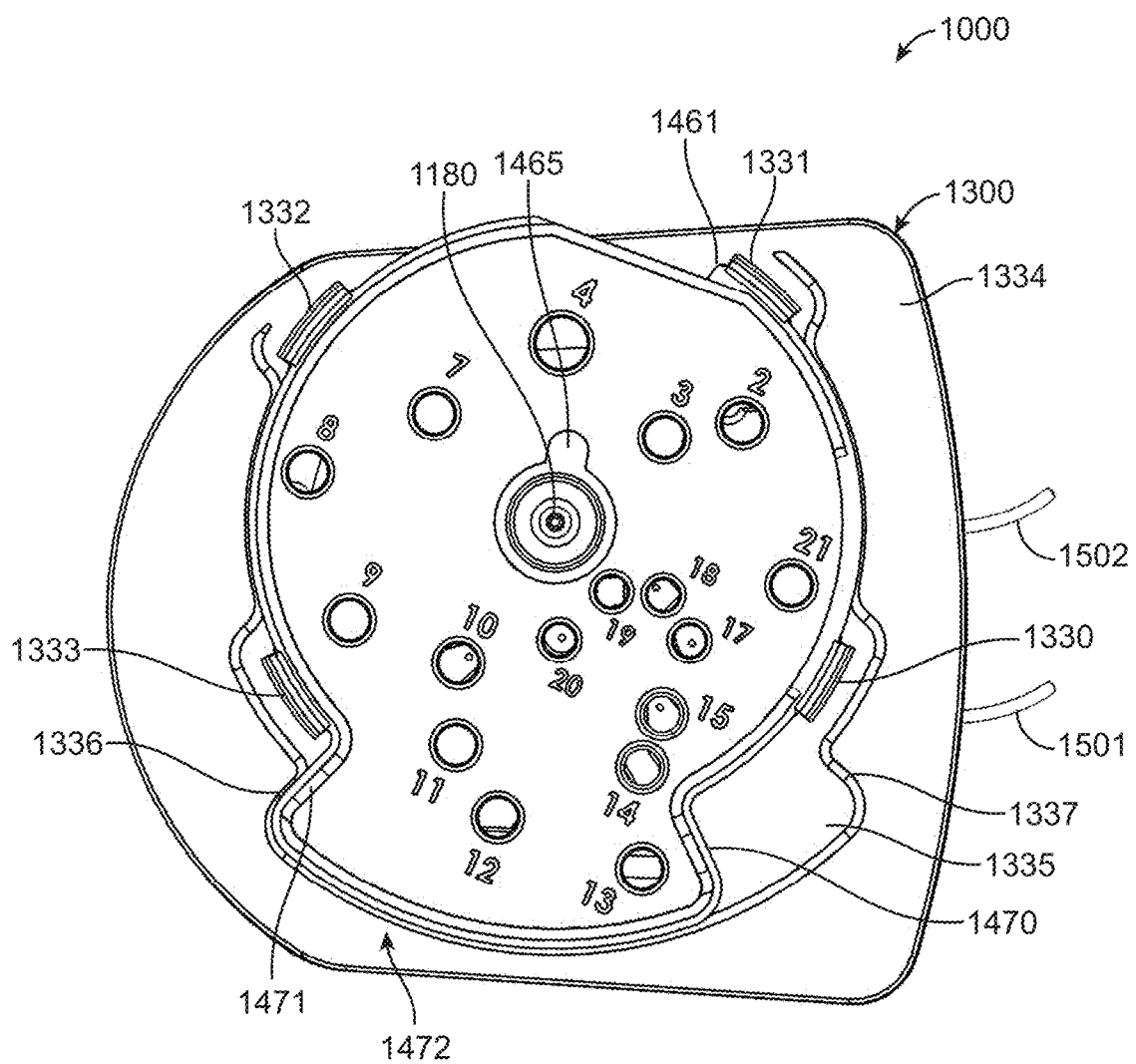
FIG. 6B shows a top view of the lid in the open position.

Opening closure 1400 allows the reservoirs to be accessed, for example, to add or remove reagents. Closure 1400 can be opened by clockwise rotation about 30° until the left side of handle region 1472 contacts stop 1336 (see FIG. 6B). The access holes 2-4, 7-15 and 17-21 are open to the respective reservoirs in the open position. A view of the locations of holes in lid 1300 is shown in FIG. 8 and can be compared to the locations of the holes in closure 1400 shown in FIG. 7. The open and closed positions are attained by rotating closure 1400 around the hub formed by extended wall 1340. Guides 1330-1333 jut from surface 1334 and contact rail 1461, which runs along the perimeter of the closure, to maintain closure 1400 in the desired plane during rotation. Barrel 1180 is externally accessible to a piston that can pass through the hub in all positions of the closure 1400. Several of the features of closure 1400 are also evident from the top view of the isolated closure in FIG. 7B.

Figure 7A:
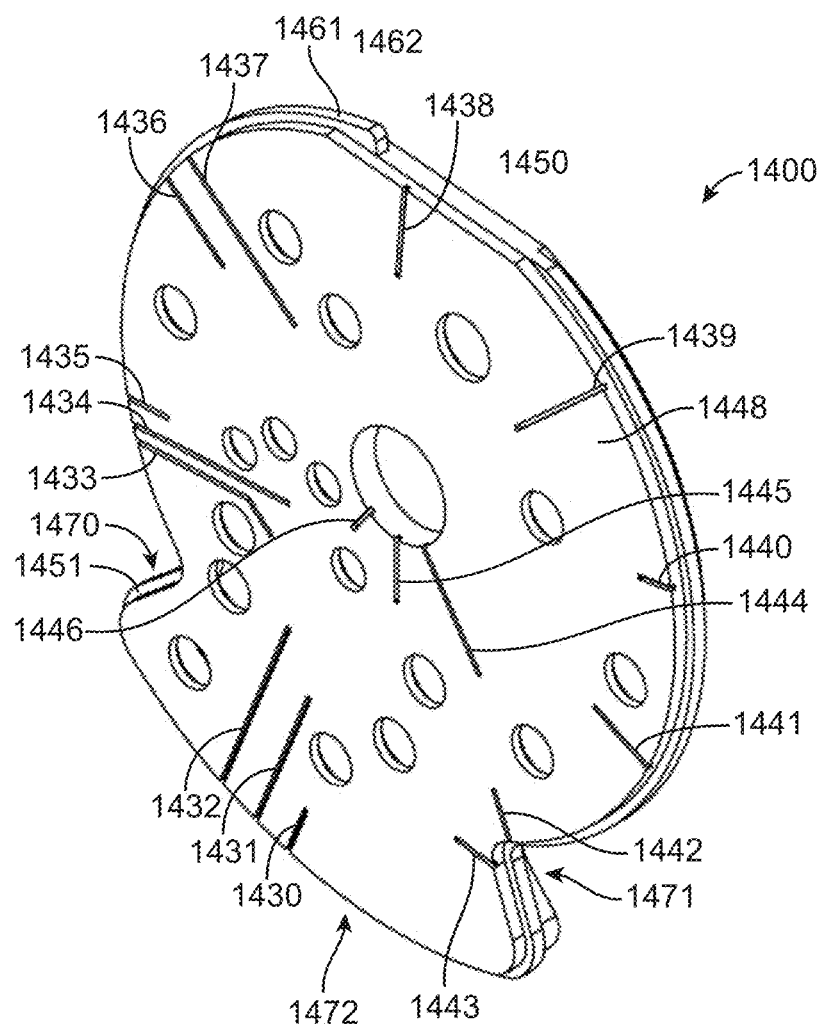
FIG. 7A shows a bottom perspective view of a moving component of a lid for a fluidic cartridge.
Figure 7B:
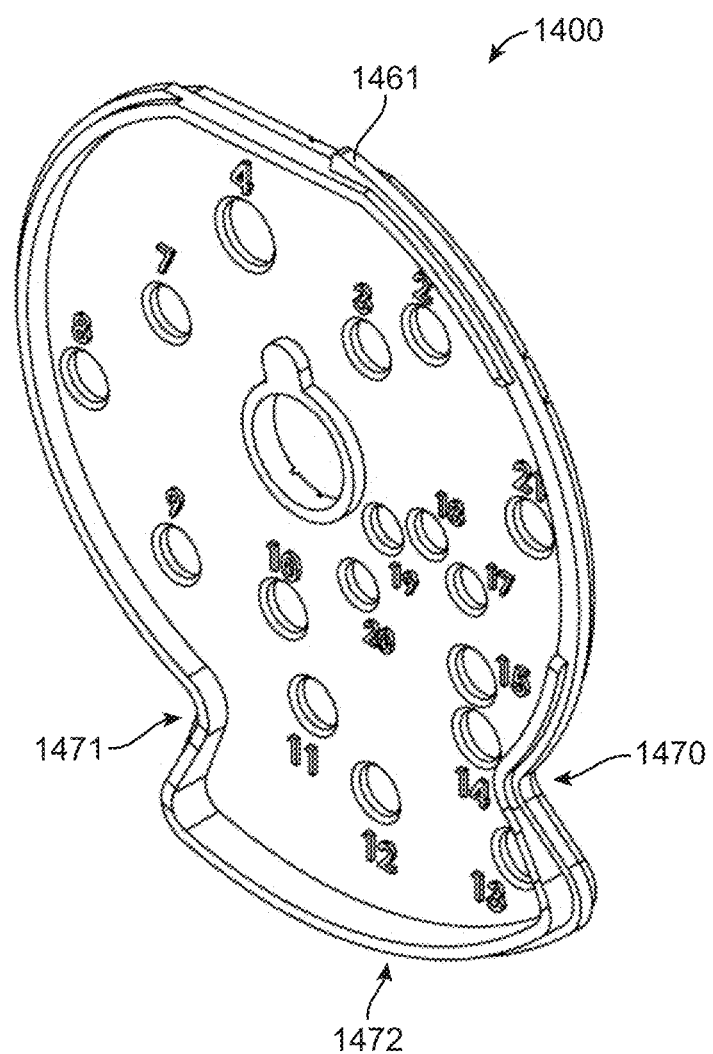
FIG. 7B shows a top perspective view of the moving component of the lid.
Figure 8A:
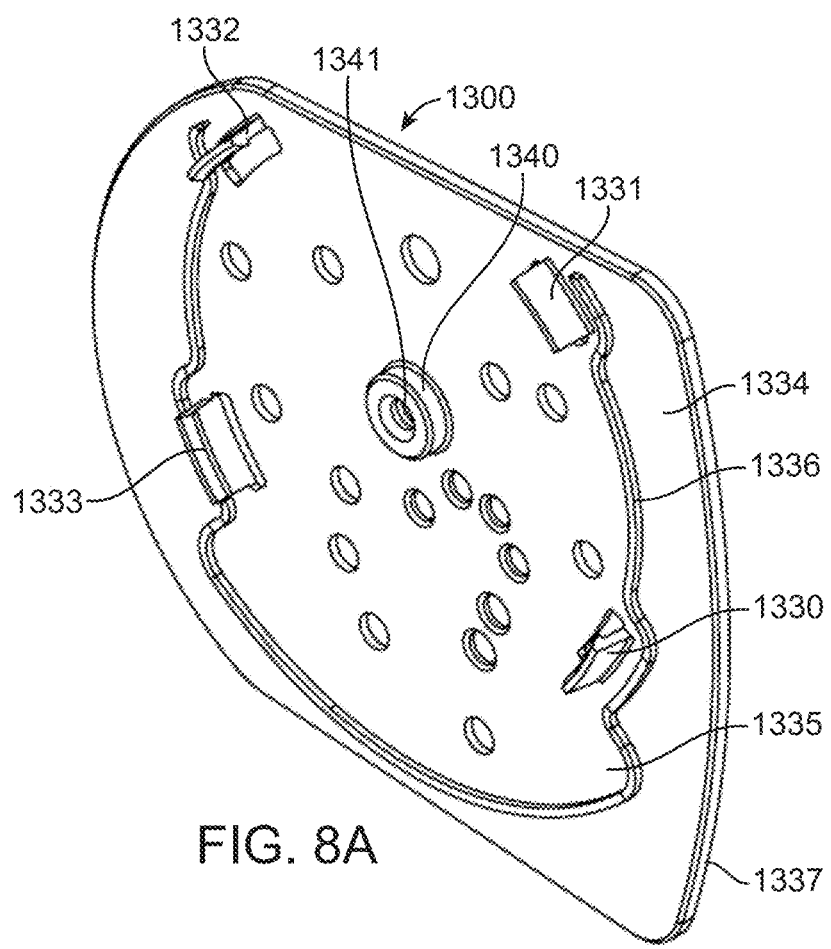
FIG. 8A shows a top perspective view of a fixed component of a lid for a fluidic cartridge.
Figure 8B:
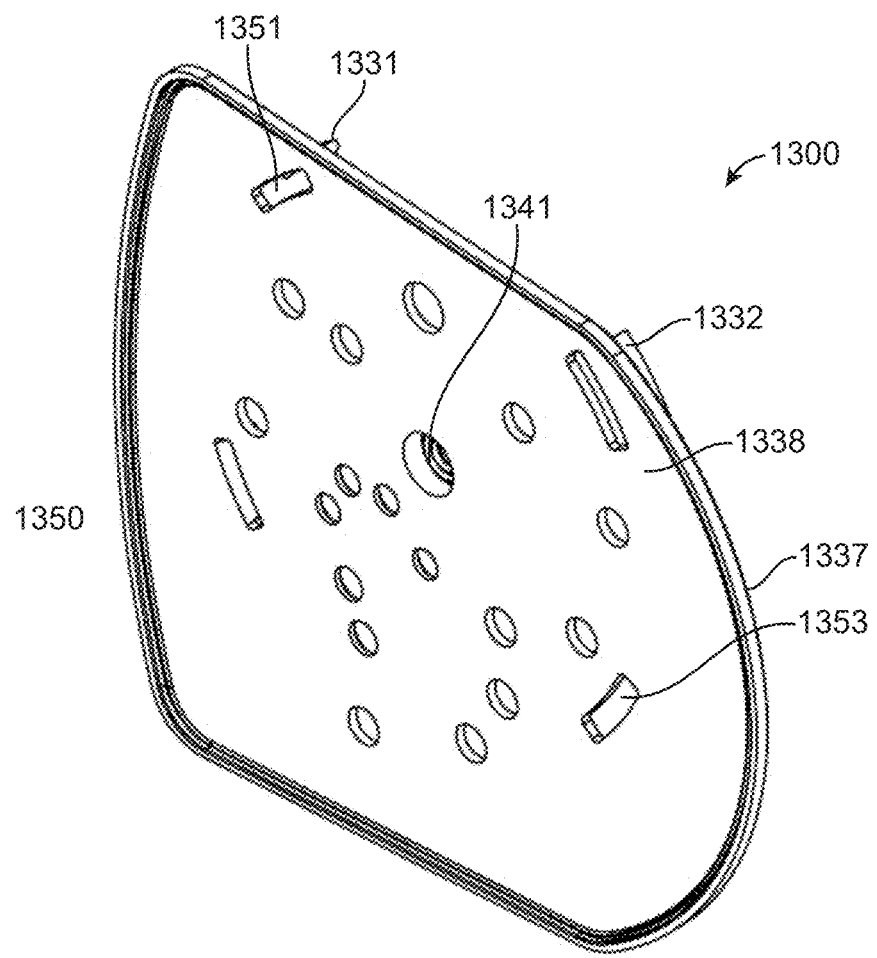
FIG. 8B shows a bottom perspective view of the fixed component of the lid.

FIG. 7A provides an isolated view of closure 1400 from below. The bottom side 1448 contacts surface 1335 of lid 1300 during all points in its rotation. The bottom side 1448 includes vents 1430-1446 which are positioned to open each reservoir to outside atmosphere when closure 1400 is in the closed position. A view of the locations of holes in lid 1300 is shown in FIG. 8 and can be compared to the locations of the vents in closure 1400 shown in FIG. 7. The vents have a small diameter that provides gas venting, but limits or prevents fluid passage, for example, in the event the closed cartridge 1000 tips over. In particular embodiments, that use aqueous reagents, a vent can have a diameter that is on the order of about 0.2 to 0.5 mm. Other diameters can be used as desired to suit a particular use of a cartridge set forth herein.

The lid configuration in FIGS. 6A-6B and 7A-7B allow a user to interact with virtually all of the reservoirs. An alternative configuration can be used whereby a user has access to only a subset of reservoirs or perhaps only the nucleic acid sample reservoir. An example is shown in FIG. 14C where an end user has access to add a sample to cartridge 4000 via a port formed by wedge shaped openings 4443, 4433 and 4413 in lid 4440, fluid holder 4430 and base 4410, respectively. This configuration can be beneficial to avoid contamination of reagent reservoirs and to simplify a user's interaction with the apparatus. Base 4410 forms a barrier for the reservoirs in body component 4100. Base component 4410 includes several openings 4414, 4415, 4416 and 4417 that can be used to deliver fluid from fluid holder 4430 into the desired reservoirs. Fluids can be contained in reservoirs 4435, 4436 and 4437 and delivered to lower reservoirs in body 4100 (reservoirs shown in FIG. 14A but omitted in FIG. 14C for clarity). Delivery can result from piercing reservoirs 4435, 4436, and 4437 when properly positioned over passages 4414 through 4417, which connect to appropriate reagent reservoirs when present in body 4100. This configuration allows liquids to be contained in the upper reservoirs of fluid holder 4430 while dried reagents (e.g. lyophilized proteins, salts, etc.) are maintained in lower reservoirs of body 4100. Separation of dried reagents from liquids can be helpful during shipping or storage of sensitive reagents.

Base 4410 includes a cylindrical guide 4412 that aligns with a cylindrical guide 4120 in body component 4100. The aligned guides create a barrel to accommodate the piston for a pump or pressure source. The piston is retained within the cartridge by base 4410. The plunger rod in the instrument "picks up" the plunger 4150 by driving it all the way down onto 4100 to force a compression fit between the plunger rod and plunger 4150. The base 4410 also strips the plunger off the plunger rod at the end of use when the plunger rod is pulled above the base 4410. Lid 4440 closes the cartridge to prevent spillage while still allowing venting of chambers. This is beneficial for preventing cross contamination of reagent chambers or pressure/vacuum buildup that would cause incorrect volumetric delivery.

Any of a variety of flow cells can be attached to cartridge 1000 via tubes 1501 and 1502. Particularly useful flow cells are those that include at least one channel having a first end that connects to the end of tube 1501 that is distal with respect to the cartridge, and the second end of the channel can connect to the distal end of tube 1502. In some embodiments, the flow cell can include a plurality of channels that connect to tubes 1501 and 1502 via respective manifolds.

Figure 13A:
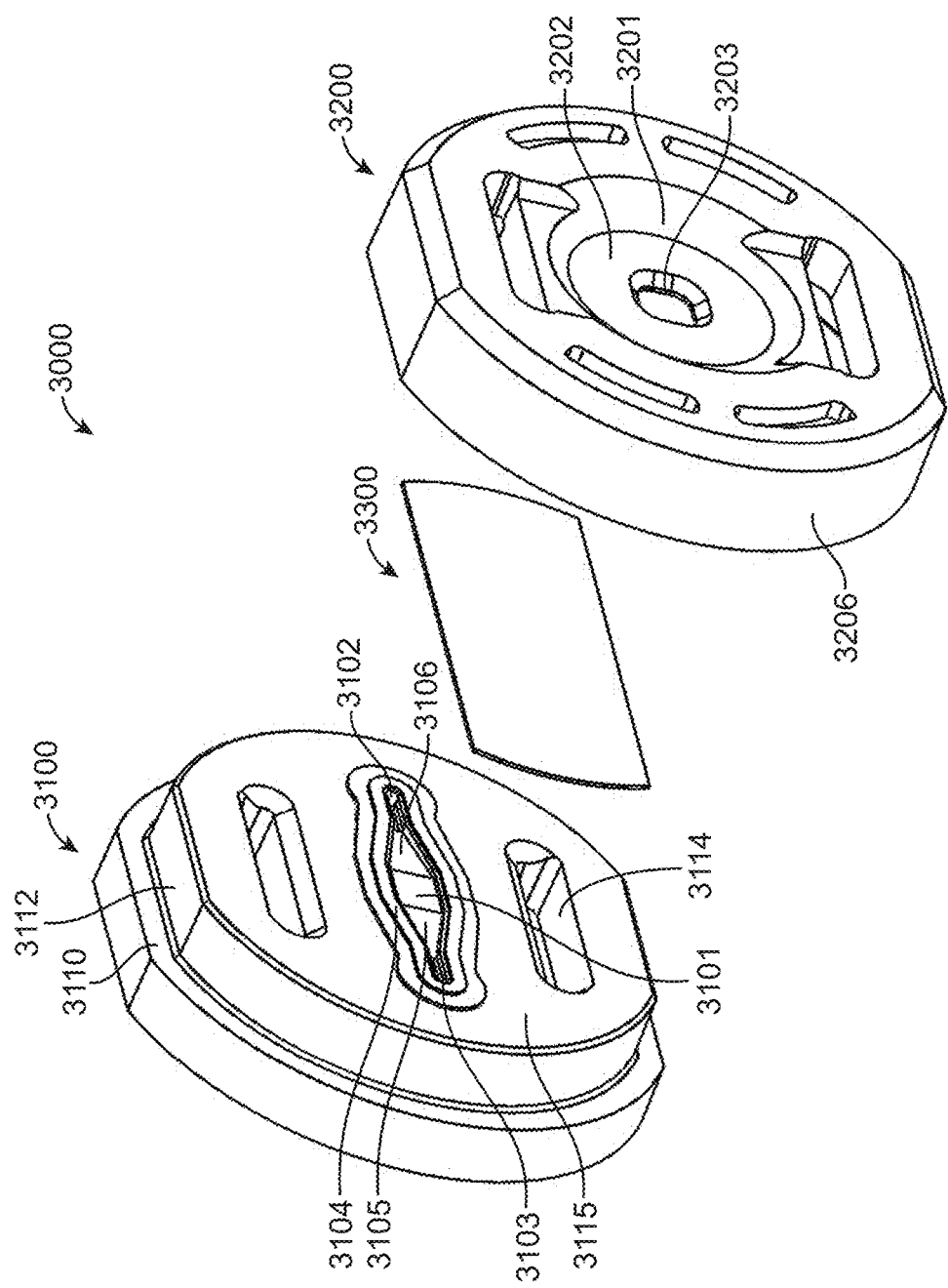
FIG. 13A shows a top perspective, exploded view of a flow cell.
Figure 13B:
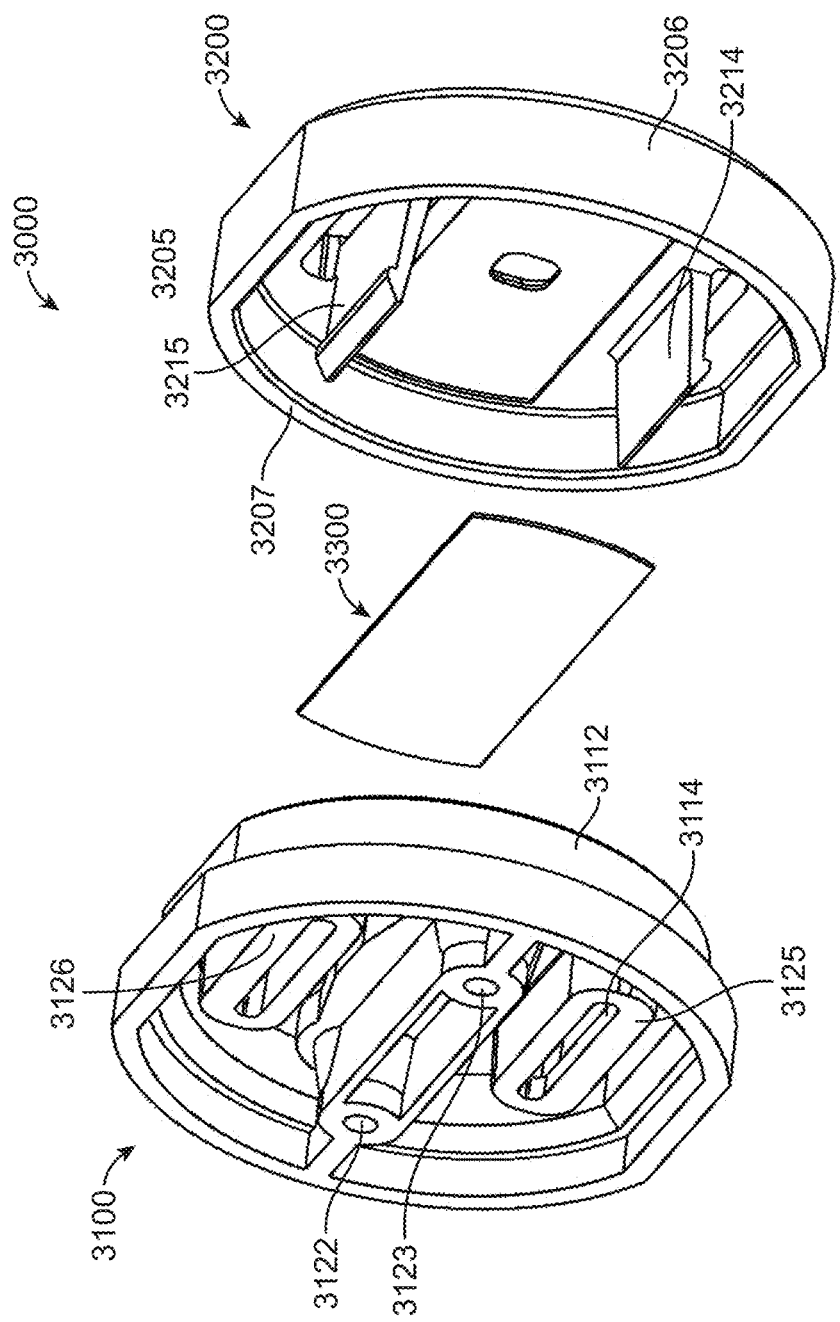
FIG. 13B shows a bottom perspective, exploded view of the flow cell.
Figure 13C:
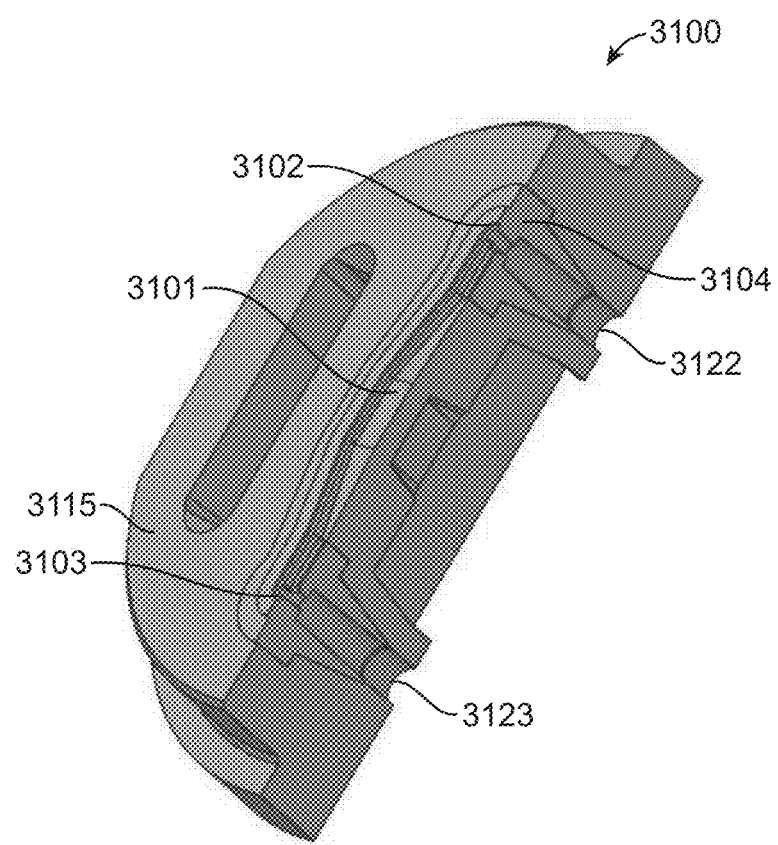
FIG. 13C shows a cross section of the optical guide of the flow cell.

An exemplary single channel flow cell 3000 is shown in FIGS. 13A-13C. The flow cell includes a fluidic guide 3100 and optical guide 3200 that sandwich an optical window 3300. As shown in FIG. 13A, fluidic guide 3100 includes a gasket 3104 that is pressed against window 3300 to create an enclosed channel in the sandwiched configuration. The sandwiched configuration is maintained by snaps 3214 and 3215 in optical guide 3200 (see FIG. 13B) that pass through apertures 3114 and 3115, respectively in fluidic guide 3100, and then click with snap windows 3125 and 3126, respectively, in fluidic guide 3100. When properly engaged in the sandwich configuration, collar 3206 of optical guide 3200 will surround wall 3112 of fluidic guide 3100 and distal surface 3207 of collar 3206 will be urged flush against rim-shaped stop 3110 of fluidic guide 3100.

The enclosed channel has an opening at a first end formed by aperture 3102 which passes through fluidic guide 3100 to connector 3122. A second opening 3103 occurs at the other end of the channel and passes through fluidic guide 3100 to aperture 3123. Connectors 3122 and 3123 are shaped to couple with tubes 1501 and 1502 from fluidic cartridge 1000. The fluid channel has a widened detection region 3101 that is flanked by fluid diffusion regions 3105 and 3106. Accordingly, fluid can pass from the main channel of cartridge 1000 through tube 1501, then through aperture 3102, to then diffuse as it passes over region 3106 to reach the wide detection area 3101 after which the fluid path narrows over diffusion region 3105 to pass through aperture 3103 to tube 1502 and back into the main channel of cartridge 1000. As set forth previously herein, the fluid can also move in the opposite direction through the flow cell. The integration of gasket 3104 to fluidic guide 3100 is evident from FIG. 13C. The gasket 3104 can be made from a supple material that forms a fluid seal when compressed against the optical window 3300, whereas the fluidic guide 3100 is generally made from a relatively non-compressible, hard material.

Optical guide 3200 includes an opening 3203 that is surrounded by a seat 3202, which is in turn surrounded by a beveled inset 3201. The beveled inset 3201 and seat 3202 are generally complementary to an optical objective and, as such, will position the objective to view a portion of window 3300 that is opposite widened detection region 3101.

In particular embodiments, a flow cell will include a solid support to which one or more target analytes of interest are attached. A particularly useful solid support is one having an array of features. Arrays provide the advantage of facilitating multiplex detection. For example, different analytes (e.g. nucleic acids, proteins, candidate small molecule therapeutics etc.) can be attached to an array via linkage of each different analyte to a particular feature of the array. Exemplary array substrates that can be useful include, without limitation, a BeadChip™ Array available from Illumina, Inc. (San Diego, Calif.) or arrays such as those described in U.S. Pat. No. 6,266,459; 6,355,431; 6,770,441; 6,859,570; or 7,622,294; or PCT Publication No. WO 00/63437, each of which is incorporated herein by reference. Further examples of commercially available array substrates that can be used include, for example, an Affymetrix GeneChip™ array. A spotted array substrate can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful array substrates include those that are used in nucleic acid sequencing applications. For example, arrays that are used to attach amplicons of genomic fragments (often referred to as clusters) can be particularly useful. Examples of substrates that can be modified for use herein include those described in Bentley et al., Nature 456:53-59 (2008), PCT Pub. Nos. WO 91/06678; WO 04/018497 or WO 07/123744; U.S. Pat. No. 7,057,026; 7,211,414; 7,315,019; 7,329,492 or 7,405,281; or U.S. Pat. App. Pub. No. 2008/0108082 A1, each of which is incorporated herein by reference.

Several embodiments utilize optical detection of analytes in a flow cell. Accordingly, a flow cell can include one or more channels each having at least one optically transparent window. In some cases, analytes are attached to an inner surface of the window(s). Alternatively or additionally, one or more windows can provide a view to an internal substrate to which analytes are attached.

Although several embodiments have been exemplified herein with respect to detecting analytes that are attached to solid supports in a flow cell, it will be understood that analytes need not be attached to a solid support and can instead be detected in a flow cell while in solution phase. Furthermore, flow cells need not be used or even configured for optical detection. Rather flow cells can be configured for alternative detection modalities using compositions and methods known to those skilled in the art for carrying out those detection modalities.

Exemplary flow cells and physical features of flow cells that can be useful in a method or apparatus set forth herein are described, for example, in US Pat. App. Pub. No. 2010/0111768 A1, WO 05/065814 or US Pat. App. Pub. No. 2012/0270305 A1, each of which is incorporated herein by reference in its entirety.

Figure 11:
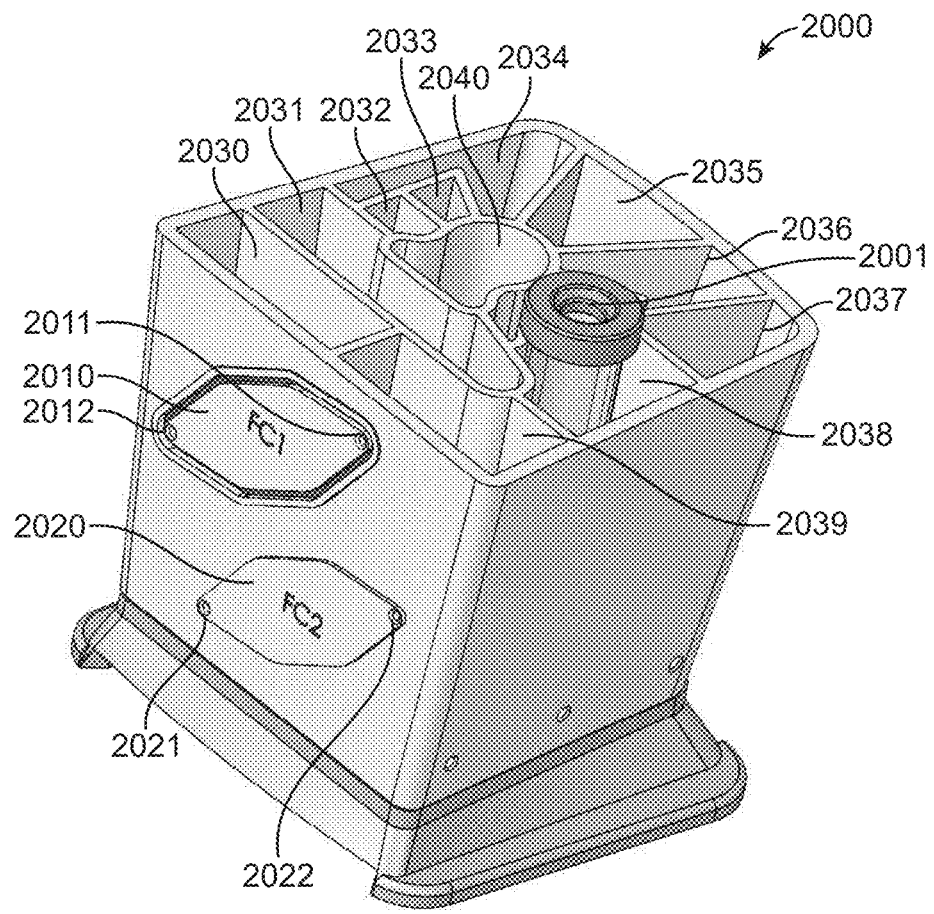
FIG. 11 shows exemplary cartridge attachment points for two integrated flow cells.

In particular embodiments, several of which have been exemplified in FIGS. 1 through 8, a flow cell can be attached to a cartridge via tubes. This modular configuration allows a cartridge and flow cell to be separable. As an alternative configuration, one or more flow cell, for example having features set forth herein, can be integrally connected to a cartridge having one or more of the features set forth herein. FIG. 11 shows exemplary cartridge 2000 having two flow cell attachment points 2010 and 2020. First flow cell attachment point 2010 has a first fluidic connection 2011 to a main channel and a second fluidic connection 2012 to the main channel. Second flow cell attachment point 2020 has a first fluidic connection 2021 to a main channel and a second fluidic connection 2022 to the main channel. The main channel is fluidically connected to reservoirs 2030-2041 and syringe pump barrel 2001. Thus, fluids can be moved between the reservoirs and flow cells as set forth for cartridge 1000.

Figure 14A:
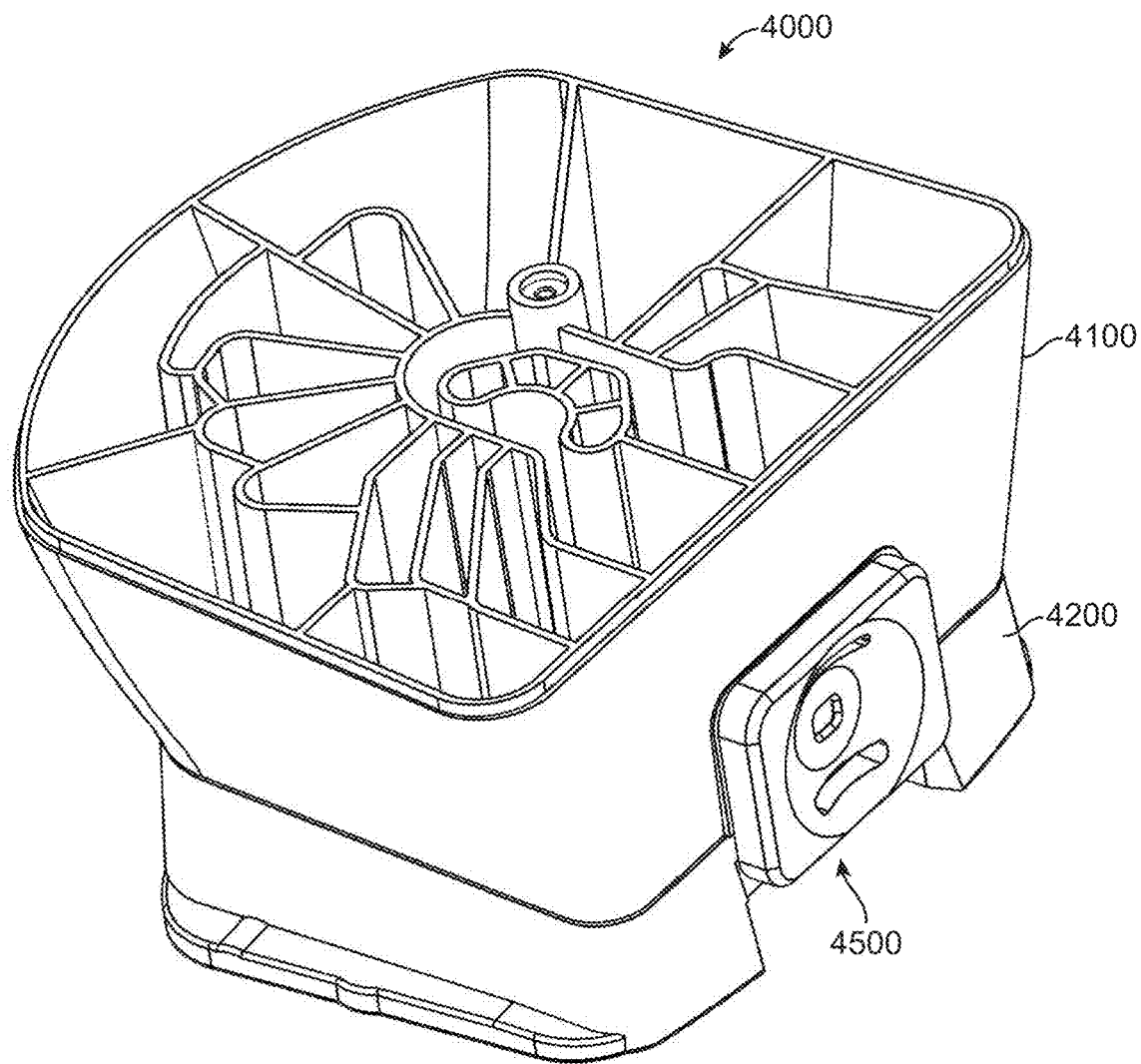
FIG. 14A shows a perspective view of a fluidic cartridge having an attached flow cell.
Figure 14B:
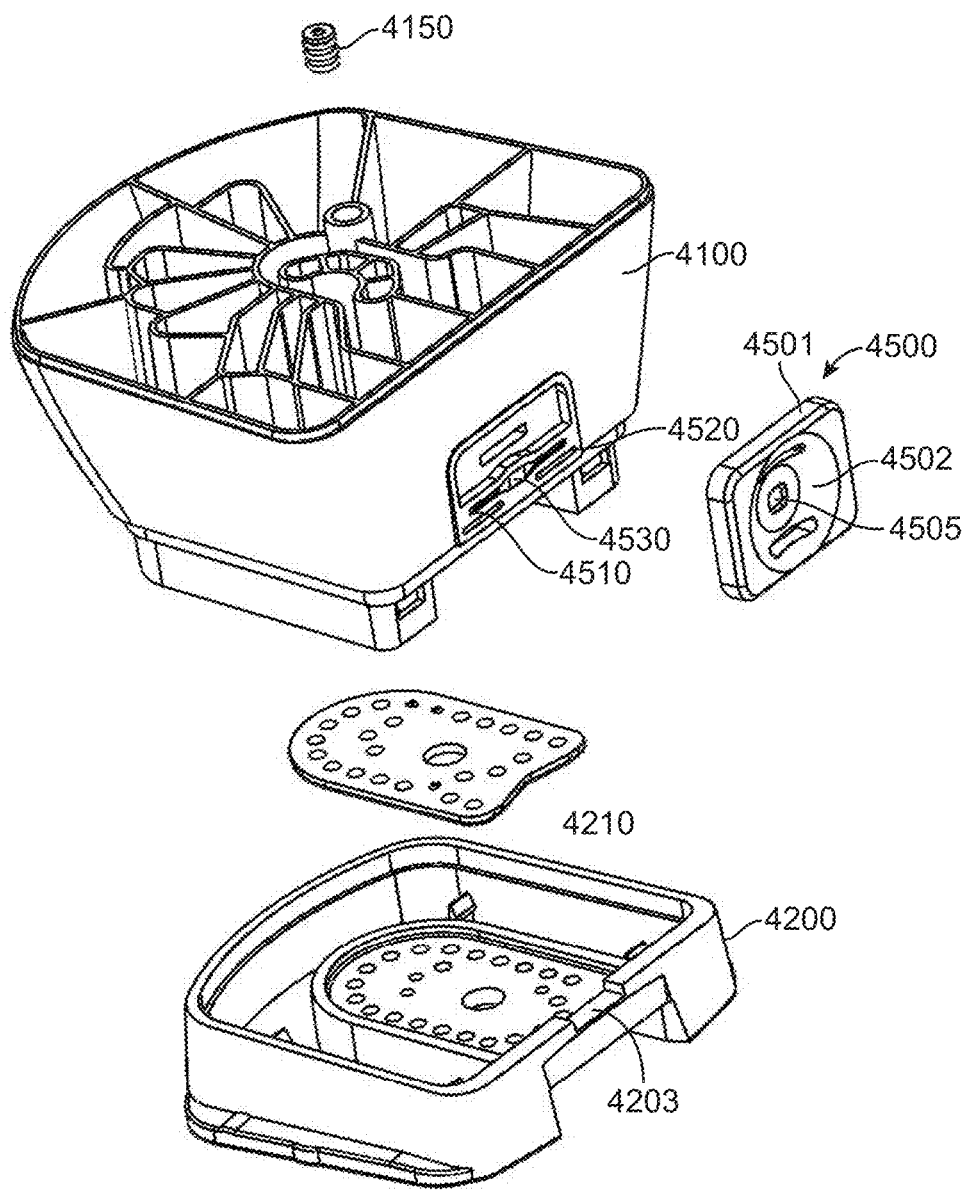
FIG. 14B shows an exploded view of the fluidic cartridge and attached flow cell.
Figure 14C:
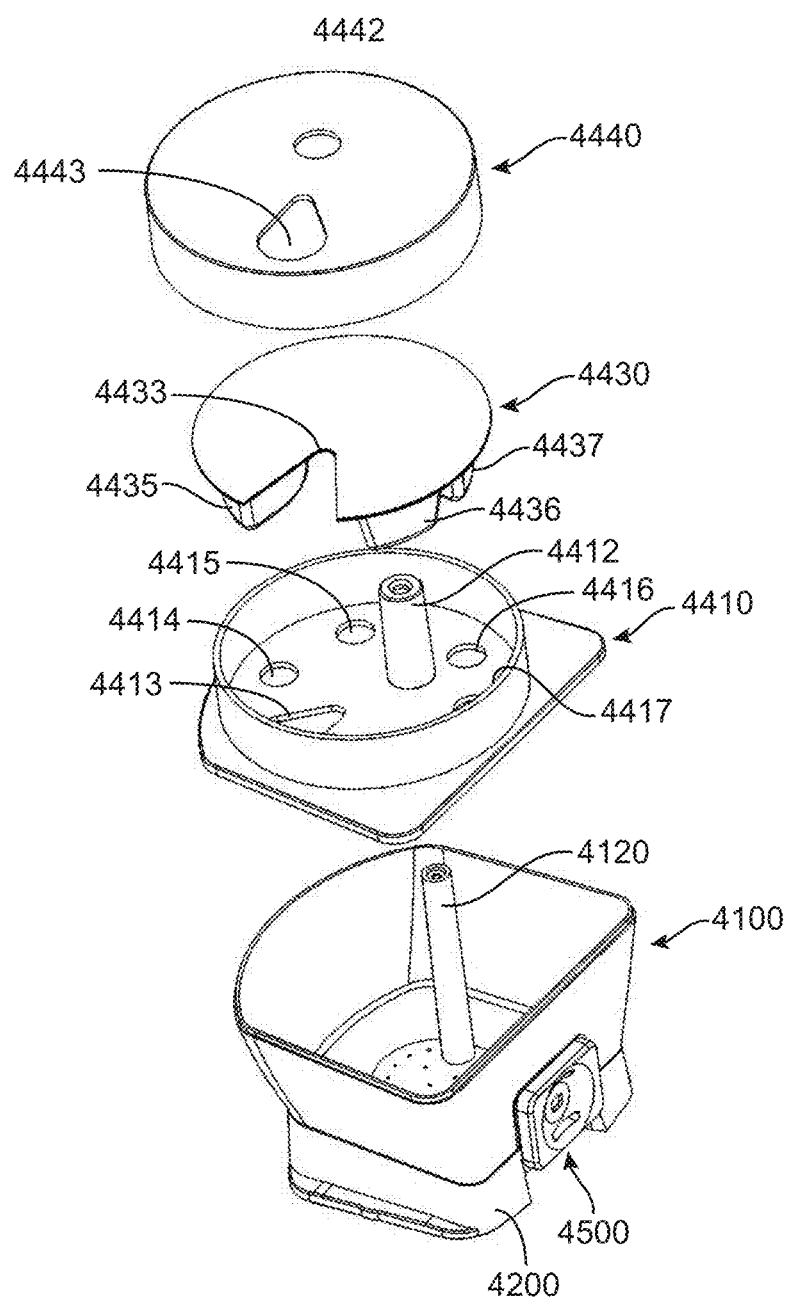
FIG. 14C shows an exploded view of a liquid reagent dispensing lid for the fluidic cartridge.

A further example of a cartridge 4000 having an attached flow cell 4500 is shown in FIGS. 14A, 14B and 14C. The overall structure of cartridge 4000 is similar to cartridge 1000 except that flow cell 4500 is directly attached to body component 4100, whereas tubes 1501 and 1502 were used to connect cartridge 1000 to a flow cell. The flow cell 4500 is formed by compressing cover body 4501 to body component 4100. Compression is formed by clicking snaps on cover body 4501 to snap window 4104 on body component 4100 and snap window 4203 formed at the interface of body component 4100 and foot component 4200. Compression will align window 4505 of cover body 4501 to the analytical portion 4530 of the flow channel. The flow channel connects to the fluidic loop of cartridge 4000 via an inlet channel 4510 and outlet channel 4520. An advantage of integrating a flow cell into a cartridge, for example, as shown by cartridges 2000 and 4000, is a reduction in the number of parts compared to cartridge 1000. For example, cartridges 2000 and 4000 lack tubing and connections used to connect cartridge 1000 to a flow cell. Omission of the tubes also results in a lower dead volume in the path from flow cell detection window to cartridge reservoirs. Furthermore, the cartridge body itself can provide one surface of the flow cell and, as such, a merely enclosing the surface can provide a flow cell. Because the flow cell is integral to cartridges 2000 and 4000, optical and fluidic alignment can be achieved together. Of course, in configurations that utilize scanning of a flow cell it may be desirable to use the modular arrangement of cartridge 1000, whereby the flow cell can be moved relative to a detector and/or relative to a fluidic cartridge.

A flow cell can be functionally interfaced with any of a variety of detection apparatus appropriate for the analytes to be observed. Particularly useful detection apparatus include, but are not limited to, those that have been used for nucleic acid sequencing. Several such detection apparatus are configured for optical detection, for example, detection of fluorescent signals. Examples of detection apparatus and components thereof that can be used to detect a flow cell herein are described, for example, in US Pat. App. Pub. No. 2010/0111768 A1 or U.S. Pat. Nos. 7,329,860; 8,951,781 or 9,193,996, each of which is incorporated herein by reference.

As shown in FIGS. 14A and 14B, the front face of cover body 4501 includes a beveled inset 4502 surrounding window 4505. The beveled inset 4502 is shaped to accommodate an optical objective for observing analytical portion 4530 of the flow channel through window 4505. The configuration allows very close positioning of an objective with respect to the analytical portion 4530 of the flow channel, thereby facilitating high resolution, high numerical aperture detection.

A detection apparatus that is used to observe a flow cell in a method or apparatus set forth herein need not be capable of optical detection. For example, the detector can be an electronic detector used for detection of protons or pyrophosphate (see, for example, US Pats App. Pub. Nos. 2009/0026082 A1; 2009/0127589 A1; 2010/0137143 A1; or 2010/0282617 A1, each of which is incorporated herein by reference in its entirety) or as used in detection of nanopores (U.S. Pat. No. 7,001,792; Soni & Meller, *Clin. Chem.* 53, 1996-2001 (2007); Healy, *Nanomed.* 2, 459-481 (2007); and Cockroft, et al. J. Am. Chem. Soc. 130, 818-820 (2008), each of which is incorporated herein by reference).

In some embodiments, a detection apparatus that interfaces with a flow cell can be one that is used in, or derived from, a known commercial nucleic acid sequencing platform such as those provided by Illumina™, Inc. (e.g. HiSeq™, MiSeg™, NextSeg™, or NovaSeq™ systems), Life Technologies™ (e.g. ABI PRISM™, SOLiD™, or Ion Torrent systems), Pacific Biosciences (e.g. systems using SMRT™ Technology such as the Sequel™ or RS II™ systems), Oxford Nanopore™ (e.g. MinION™ or PromethION™ systems) or Qiagen (e.g. Genereader™ system). Other useful detectors are described in U.S. Pat. Nos. 5,888,737; 6,175,002; 5,695,934; 6,140,489; or 5,863,722; or US Pat. Pub. Nos. 2007/007991 A1, 2009/0247414 A1, or 2010/0111768; or WO2007/123744, each of which is incorporated herein by reference in its entirety. Another useful detection device is a nanohole detector or surface plasmon resonance detector. Exemplary embodiments of SPR detection for sequencing nucleic acids are set forth in US Pat. App. Pub. No. 2017/0191125 A1, which is incorporated herein by reference in its entirety.

A particularly useful optical system uses a slide scanning mechanism as set forth in commonly owned U.S. Pat. App. Ser. No. 62/545,606, which is incorporated herein by reference. The slide scanning mechanism can provide the advantage of rapidly moving a flow cell without the need for expensive and relatively high mass stages. The flow cell can be moved independently of the fluidic cartridge.

Any of a variety of actuators can be used to open and close valves in the apparatus set forth herein. Examples include, but are not limited to, pneumatic actuators, direct solenoid actuators, pivot solenoid actuators, linkage solenoid actuators, or cable pull solenoid actuators. Generally, the valve actuation system will be configured to independently actuate a large number of valves that occupy a relatively small space. Particular embodiments exemplified herein utilize magnetic pistons that are only 5 millimeters apart to minimize the volume of reagents consumed when sequencing nucleic acids. Actuators that are capable of moving the pistons while supporting this dense spacing of valves are particularly useful.

Pneumatic actuators provide several advantages, including, for example, a well-tested actuation system that allows optimal placement of cartridge valves and associated hardware, robust components that are generally long lived, and energy efficiency. Some disadvantages include higher cost compared to the use of solenoid drives and a relatively slow speed (about 1 sec compared to 10 to 100 msec for solenoid drives).

Direct actuation of magnetic pistons by solenoids can greatly reduce the cost of a valve actuation system. Open frame solenoids are particularly useful because of their lower cost compared to tubular solenoids. Moreover, using solenoids reduces the number of parts and size of the fluidic system. It also increases the speed and reliability of the system. Another advantage of solenoid actuation methods over the use of pneumatic actuation is that a separate mechanical system is not needed for retracting the drives during loading and unloading. The printed circuit board (PCB) to which the solenoids are mounted can be used for this purpose. For example, the PCB can be spring loaded up and retracted down by the door. Spring loading the PCB up can help ensure accurate positioning of the magnet drives.

Figure 15:
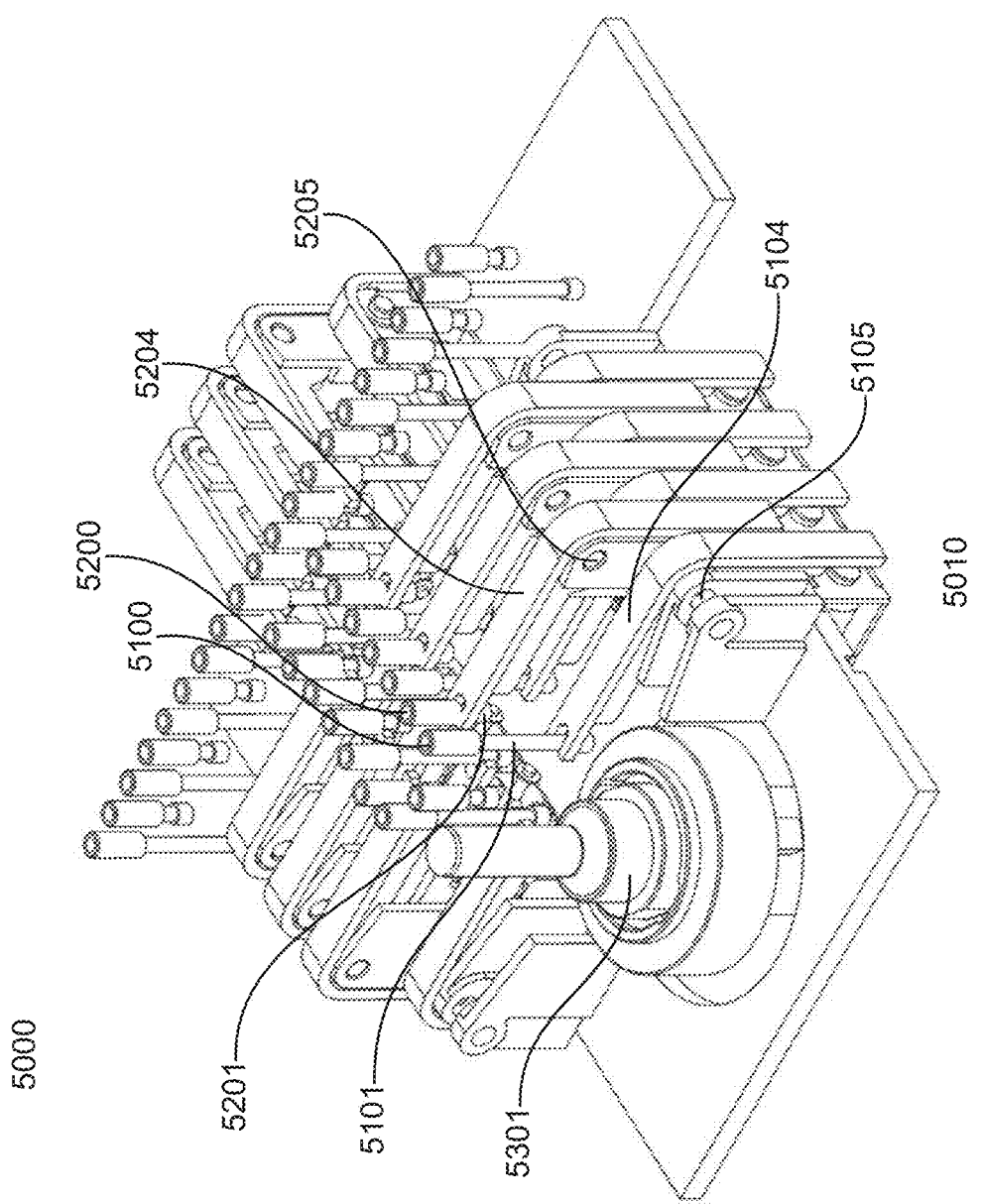
FIG. 15 shows a perspective view of an array of pivot solenoid valve actuators.

The use of pivot solenoid actuators can provide the advantages of solenoid valves set forth above. A challenge with using solenoids is to get the relatively large solenoid (e.g. 10 mm wide) to actuate 5 mm spaced magnetic pistons. Doubling this piston spacing to the width of the solenoid would increase dead volumes and reagent would be unnecessarily wasted. An example of an array of pivot solenoid actuators is shown in FIG. 15. The array includes 35 actuators that are densely packed due to offsetting of adjacent solenoids into different z planes. For example, the actuator that terminates in magnetic piston 5100 has a relatively long drive 5101 that connects to rocker arm 5104. The rocker arm forms a cantilever off pivot 5105 and is driven by solenoid 5106. The adjacent actuator, terminating in magnetic piston 5200 has a shorter drive 5201 that interacts with rocker arm 5204. As such, the pivot 5205 is at a higher z plane than pivot 5105. The solenoid that drives piston 5200 is also at a higher z plane than solenoid 5106, which drives adjacent piston 5100. The z offset allows adjacent actuators to interact with magnetic pistons that are closer in the xy plane. Also shown in FIG. 15 is an ultrasonic transducer 5301 that is positioned to lyse cells in a chamber of a fluidic cartridge that interacts with the actuator array.

Figure 16A:
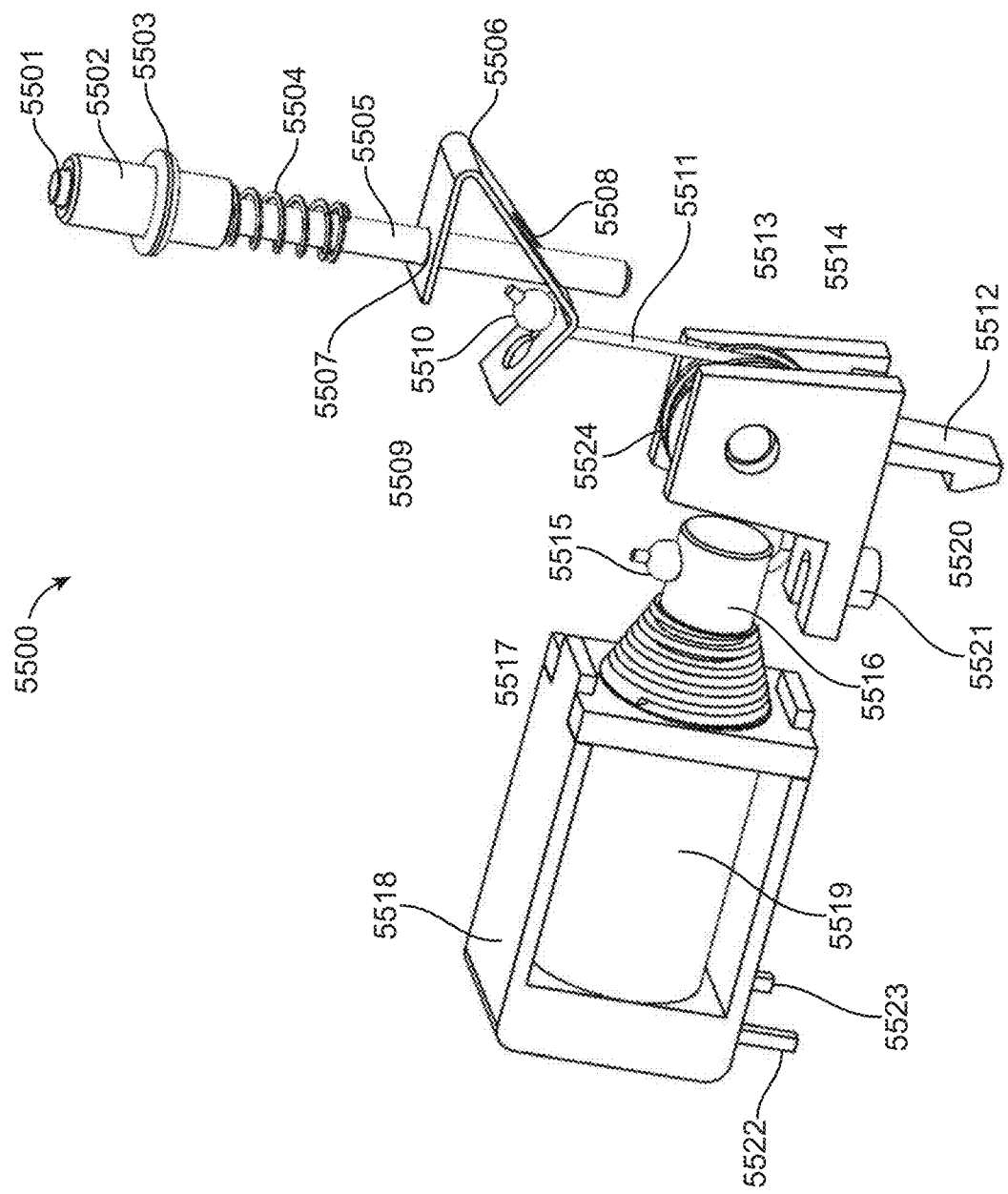
FIG. 16A shows an isometric view of a cable pull solenoid valve actuator.
Figure 16B:
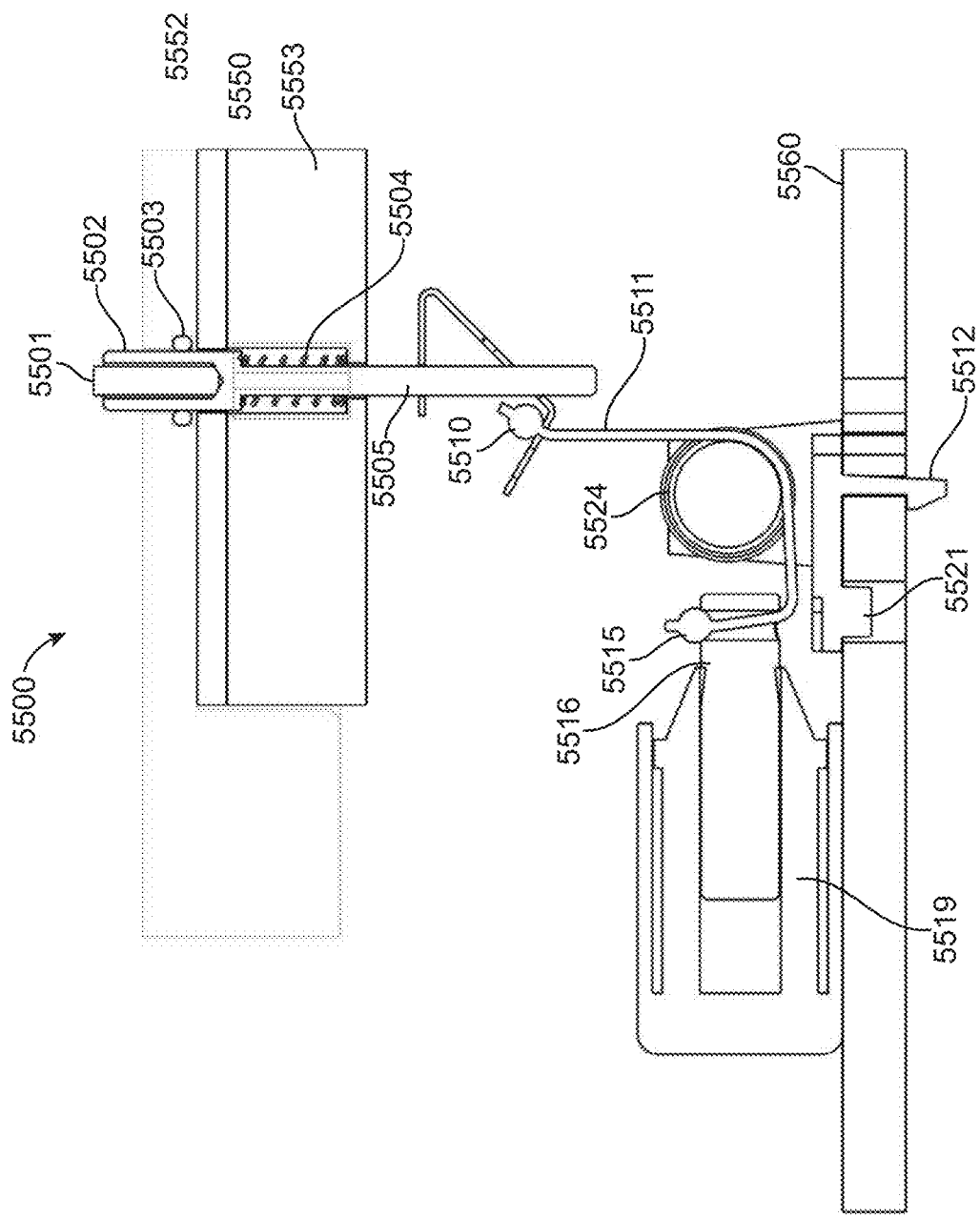
FIG. 16B shows a cut-away side view of a cable pull solenoid valve actuator in the fully extended position.
Figure 16C:
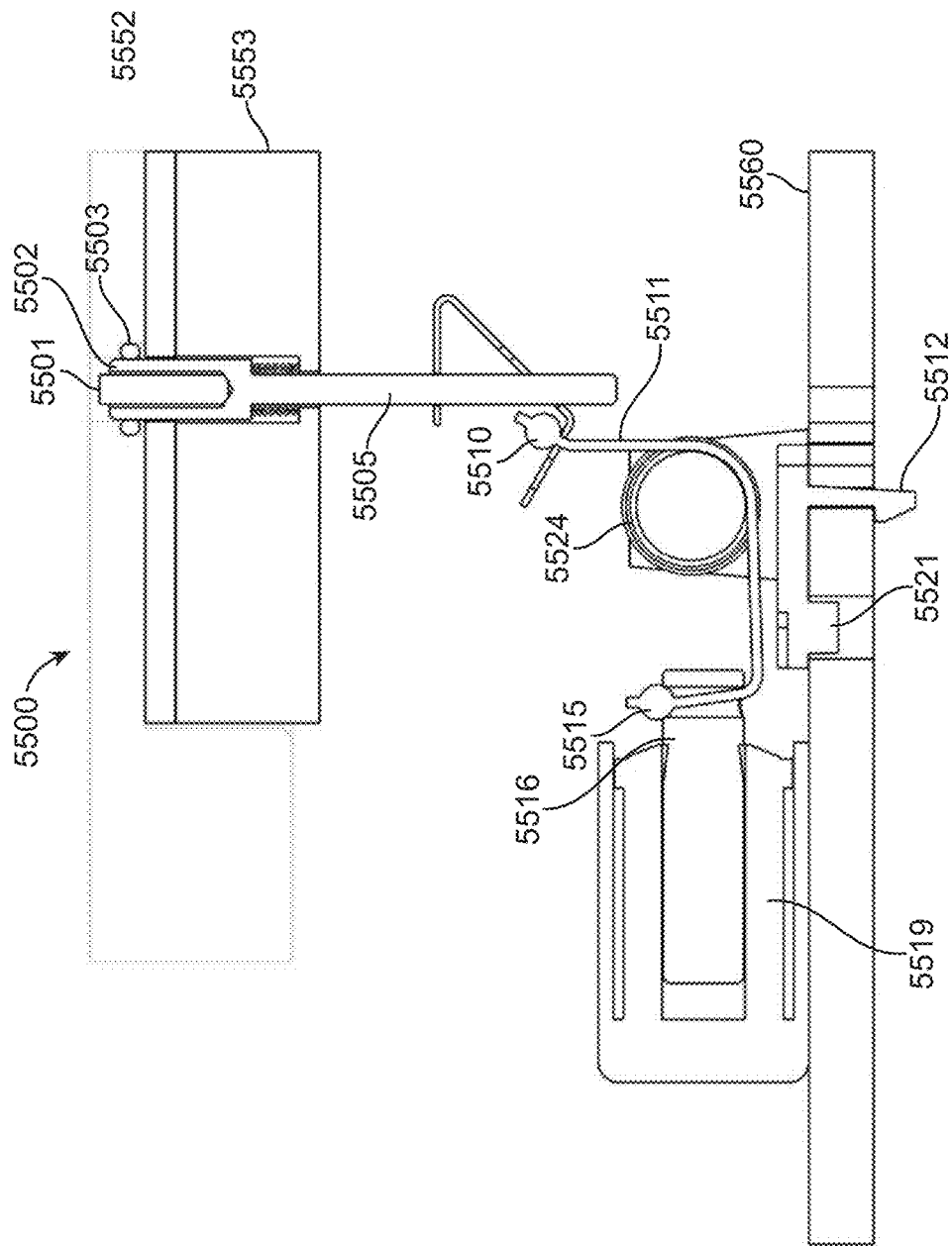
FIG. 16C shows a cut-away side view of a cable pull solenoid valve actuator in the fully contracted position.

Another useful type of solenoid actuator is a cable pull solenoid actuator. Examples are shown in FIGS. 16A through 16F. The cable pull solenoid array includes 36 open frame pull solenoids 5500 mounted on a PCB 5560. Solenoids 5500 are mounted at 10 mm spacing on the top and bottom of the PCB 5560 such that adjacent actuators have solenoids in different z-planes. This allows for independent actuation of the 5 mm spaced magnets 5501 in the reagent cartridge. A perspective view of a cable pull solenoid is shown in FIG. 16A. Magnet 5501 is attached to magnetic coupling 5502 which is, in turn, attached to an elongated shaft 5505 that is physically coupled to a cable 5511 via spring clip 5506. The spring clip includes a round hole 5507 and elongated hole 5508 through which shaft 5505 passes to form a compression fit. Spring clip 5506 also includes a keyhole having a wide opening through which a ball 5510 can pass and a narrow opening that will pull on ball 5510. Ball 5510 is attached to the proximal end of cable 5511 such that pulling on the ball 5510 will pull on spring clip 5506. Cable 5511 passes around pully 5524 and the distal end of cable 5511 is attached to ball 5515. Ball 5515 is attached to barrel 5516 of solenoid 5519. Spring clip 5506 provides a means to adjust tension on the cable pull system for optimum actuation performance. Solenoid 5519 is contained in housing 5518 which includes two pegs 5522 and 5523 for attachment to the PCB 5560. Pully 5524 is attached to PCB 5560 via clip 5512 and peg 5521. The actuator includes spring 5504 which is placed in cylinder 5554 of magnetic plate 5553 to provide a counter tension to the pulling action of the solenoid 5519. FIG. 16B shows the cable pull actuator in the fully extended position and FIG. 16C shows the cable pull actuator in the fully retracted position. O-ring 5503 is placed on magnetic drive 5502 to prevent intrusion of fluids into cylinder 5554.

Figure 16D:
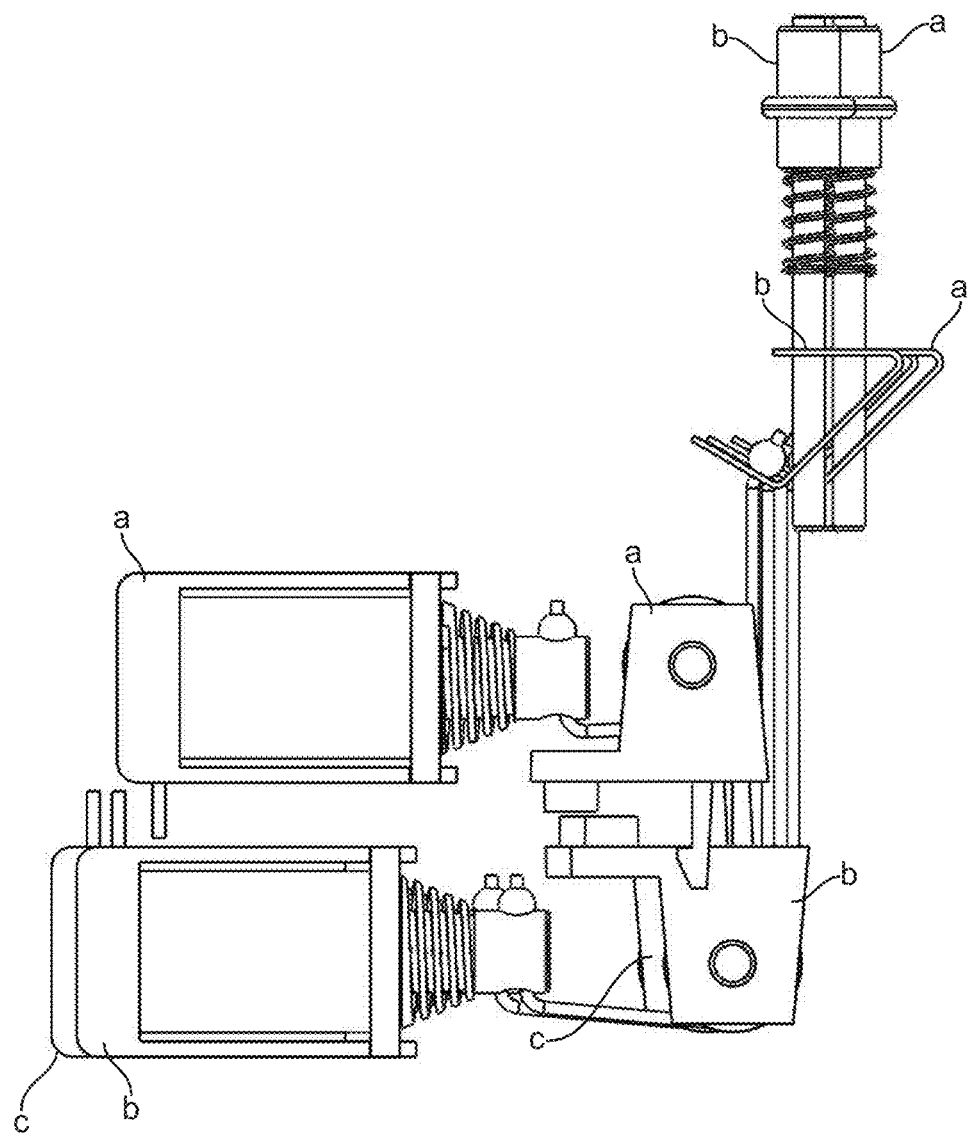
FIG. 16D shows a side view of three closely packed cable pull solenoid valve actuators.
Figure 16E:
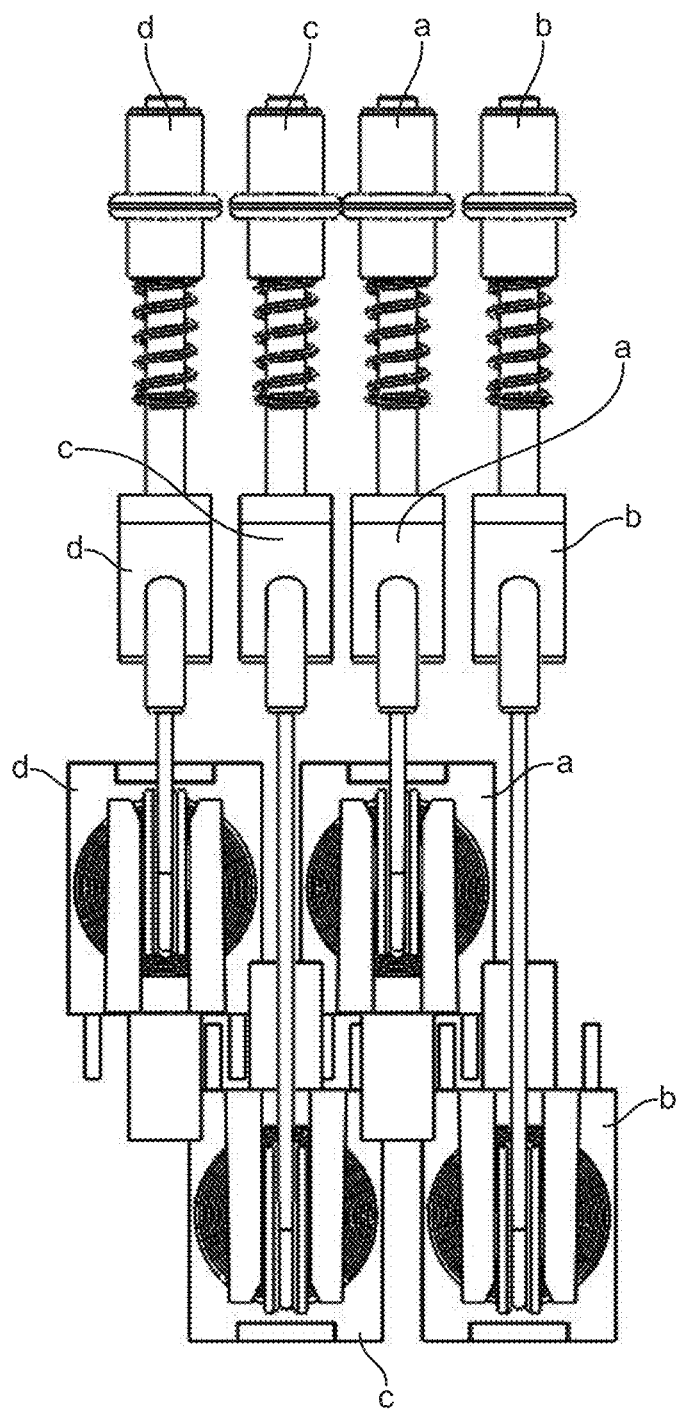
FIG. 16E shows a side view of four closely packed cable pull solenoid valve actuators.
Figure 16F:
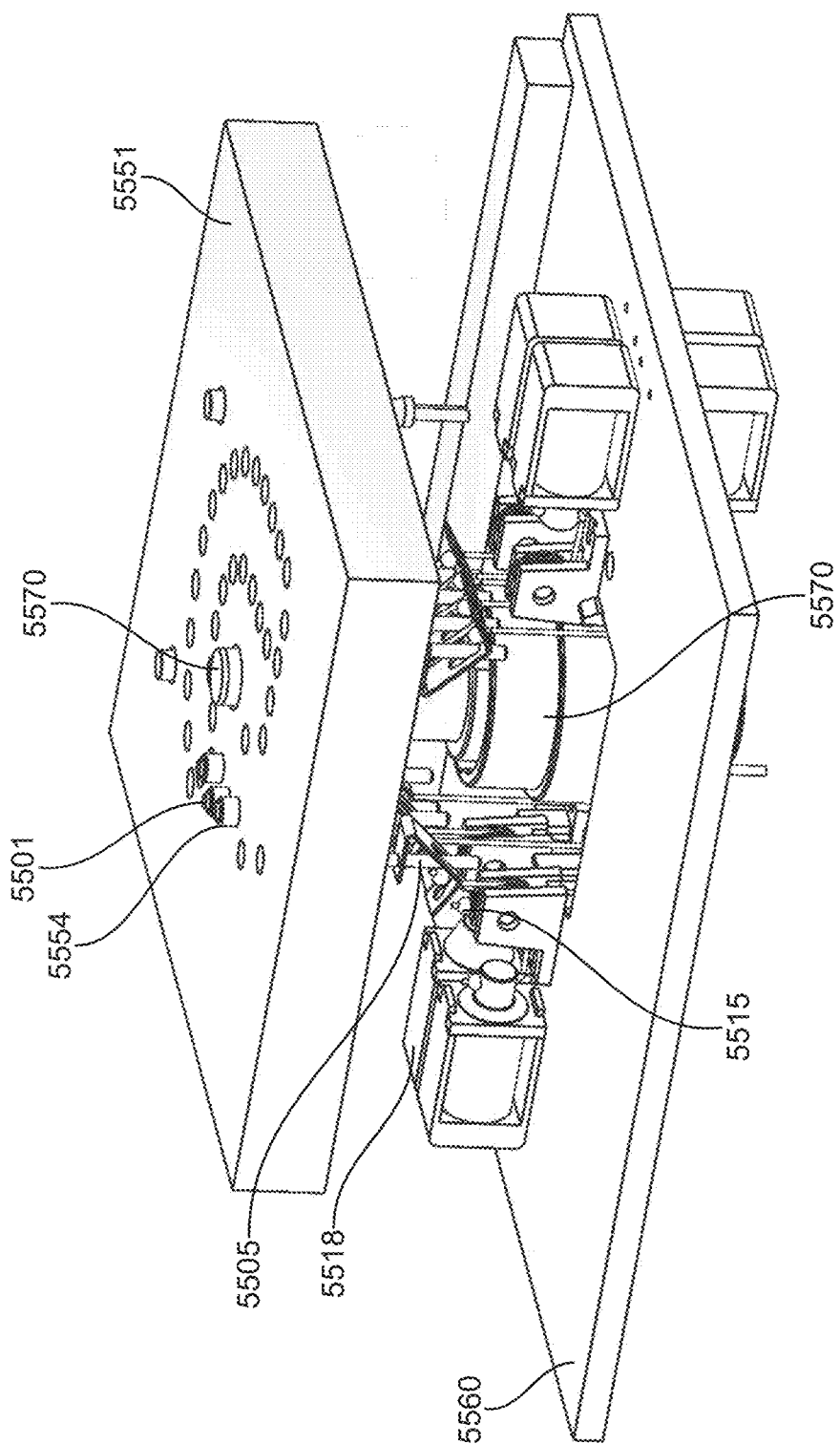
FIG. 16F shows a perspective view of an array of cable pull solenoid valve actuators.

The cable pull solenoid actuators can be efficiently packed by offsetting neighboring units in different z places. An exemplary offset for three neighboring actuators is shown in FIG. 16D (side view). A side view of four neighboring actuators is shown in FIG. 16E. A subset of actuators is shown interacting with PCB 5560 and magnetic plate 5551 in FIG. 16F. Also shown is ultrasonic transducer 5570, which is positioned to lyse cells in a chamber of a fluidic cartridge that interacts with the actuator array.

Figure 17A:
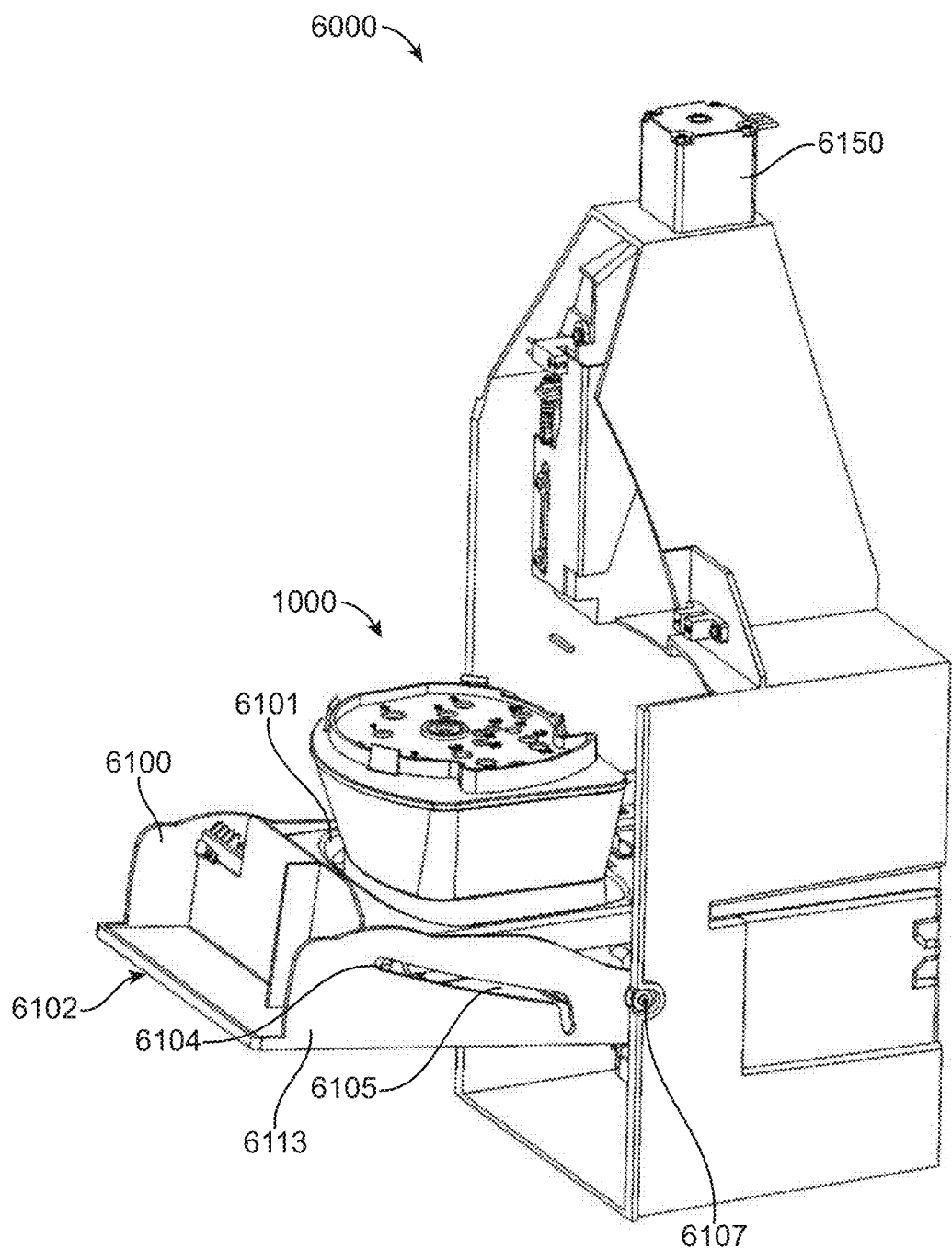
FIG. 17A shows a front perspective view of a cartridge control module with an open door and cartridge loaded therein.
Figure 17B:
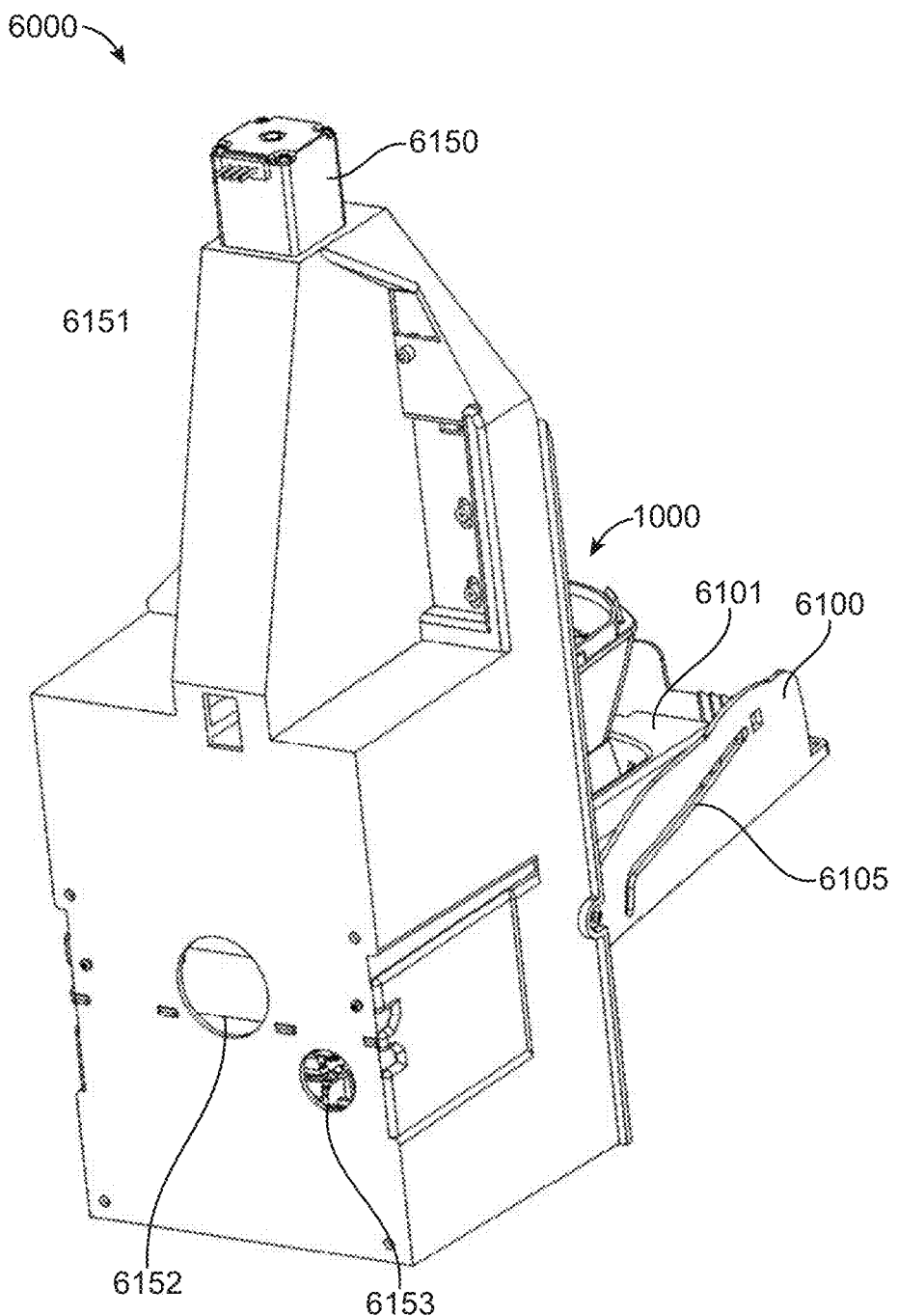
FIG. 17B shows a rear perspective view of a cartridge control module with an open door and cartridge loaded therein.
Figure 17C:
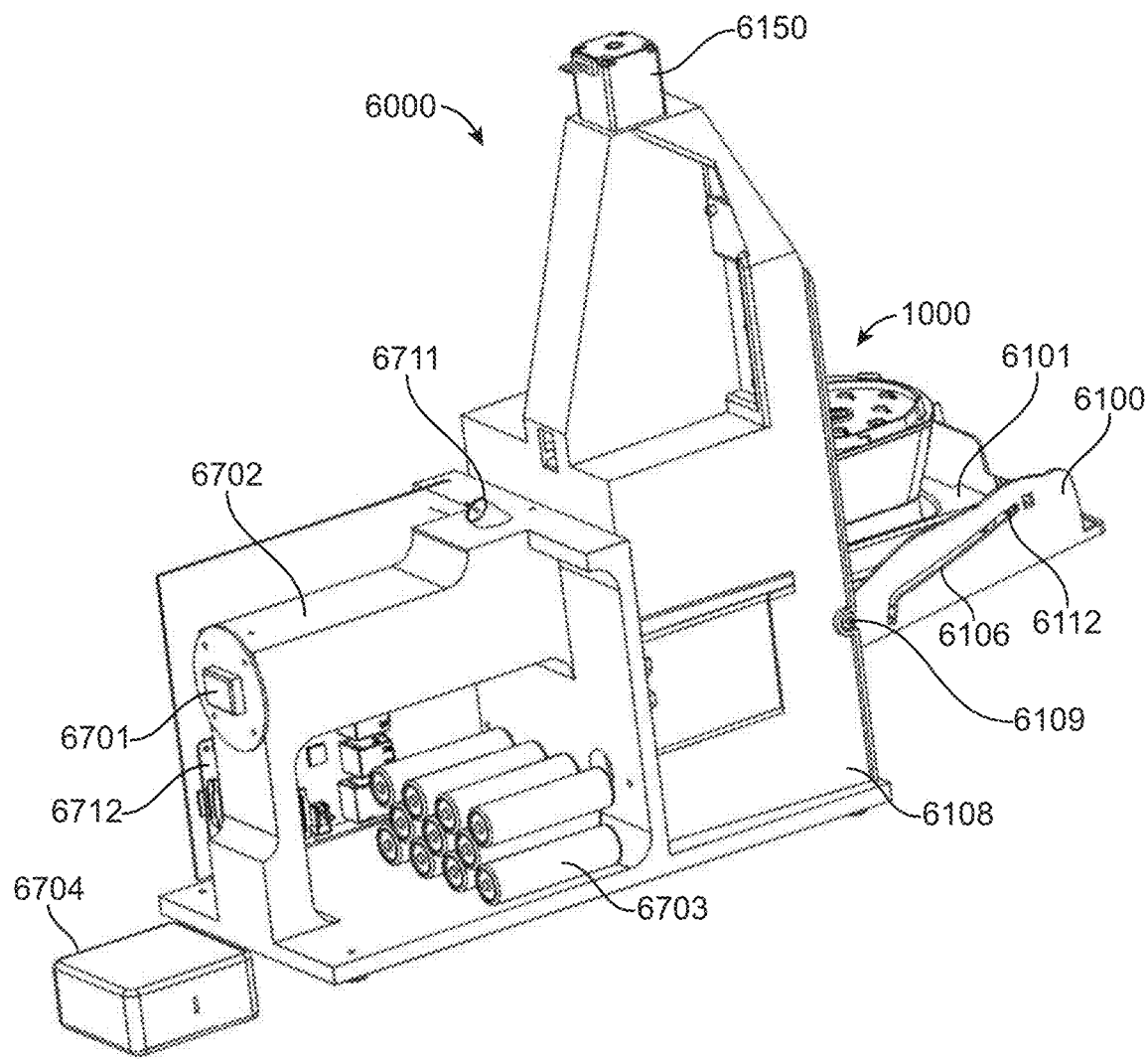
FIG. 17C shows a rear perspective view of a cartridge control module and optical detection module.

A nucleic acid sequencing system is shown in FIGS. 17A, 17B and 17C. The sequencing system consists of a cartridge control module 6000 which interfaces with an optical detection module 6700. The overall dimensions of the system are within 15 inches for the maximum height, 12 inches for the maximum length and 6 inches for the maximum width, thereby providing a relatively compact and portable design. The system is well suited for field work due to the size and the option of using either a lithium ion battery pack 6703 or an external USB-C power supply 6704 to run the instrument. The system can be enclosed within injection molded plastic covers with openings for door 6102, power supplies, air inlets and fan exhausts.

FIG. 17A shows the cartridge module 6000 with door 6102 in the open position and with cartridge 1000 loaded in receptacle 6101. Receptacle 6101 has a shape that is complementary to the foot of cartridge 1000, thus holding cartridge 1000 firmly in place for interacting with components of cartridge module 6000 once the door 6102 is closed. The components are housed within the cartridge module 6000 and include an ultrasonic transducer, array of magnetic valve actuators, heaters, separation magnet and a syringe plunger, all of which are retracted when the door is open. The plunger is actuated by stepper motor driven linear actuator 6150 located on the top of the cartridge module 6000. The door can be closed by lifting to rotate on hinges 6107 and 6109. Closing the doors will cause receptacle 6101 to slide linearly into the cavity of module 6000. The sliding motion is mechanically directed due to movement of pin 6104 along track 6105 in the right wing 6113 of door 6102, and movement of pin 6112 along track 6106 in wing 6100 of door 6102. Tracks 6105 and 6106 have a curved region at the bottom (i.e. resulting in a hockey stick shape) such that, when the door 6102 is fully closed, the receptacle 6101 is firmly seated in working position. The closing motion also causes movement of the ultrasonic transducer, array of magnetic valve actuators, heaters and syringe plunger to actively interface with cartridge 1000.

Figure 18A:
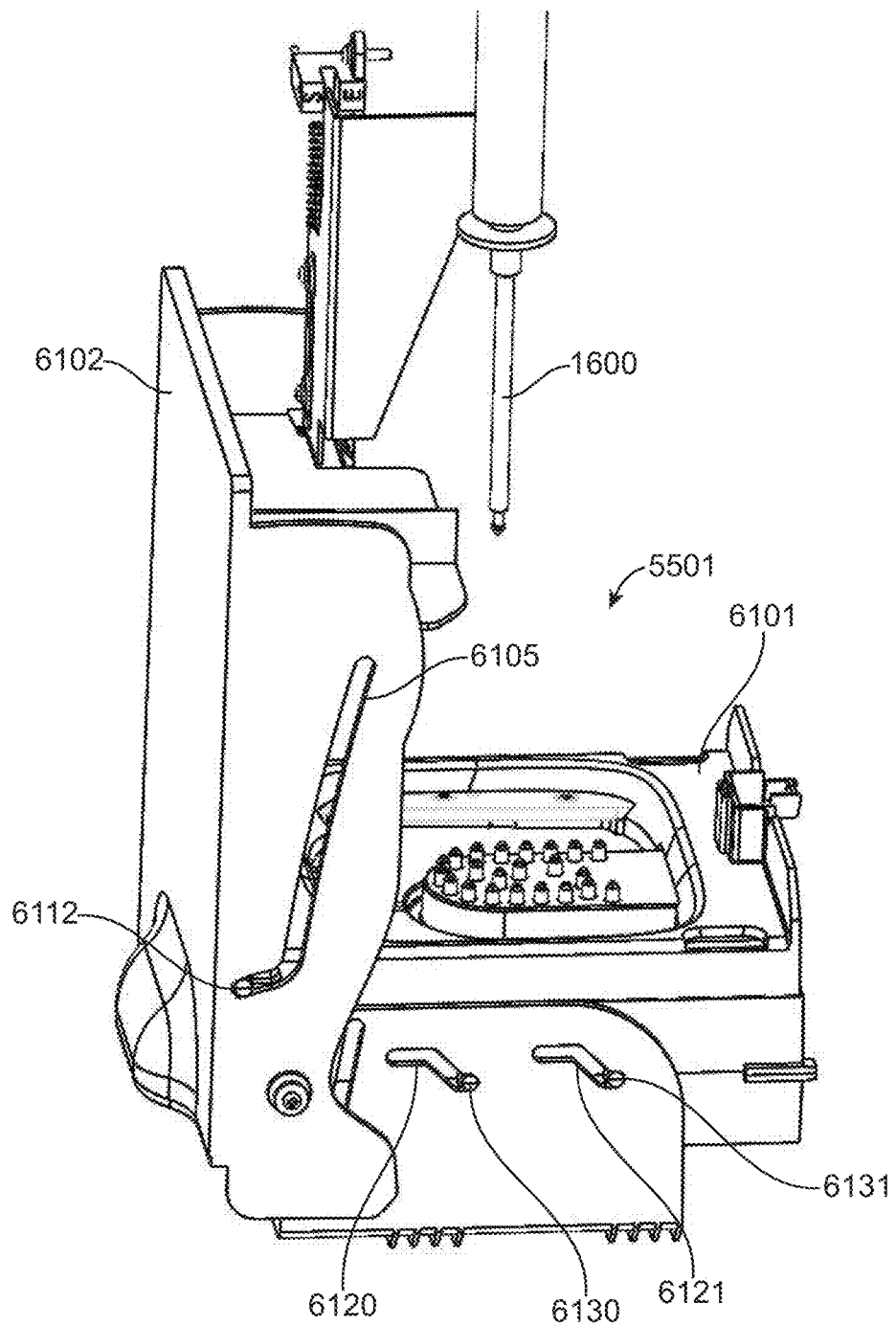
FIG. 18A shows an internal view of a cartridge control module when the door is closed.
Figure 18B:
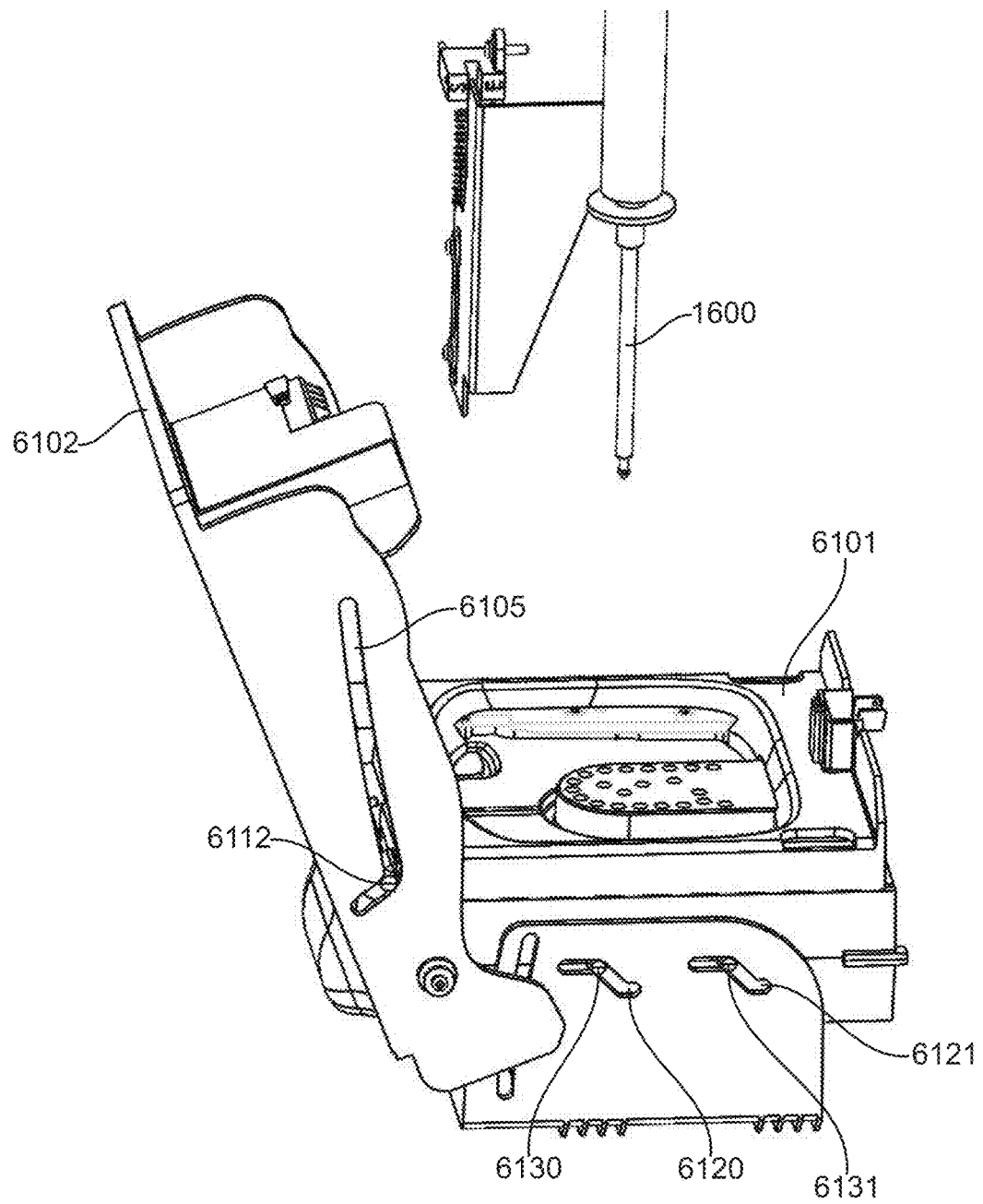
FIG. 18B shows an internal view of a cartridge control module when the door is partially opened and magnets of valve actuators are retracted.
Figure 18C:
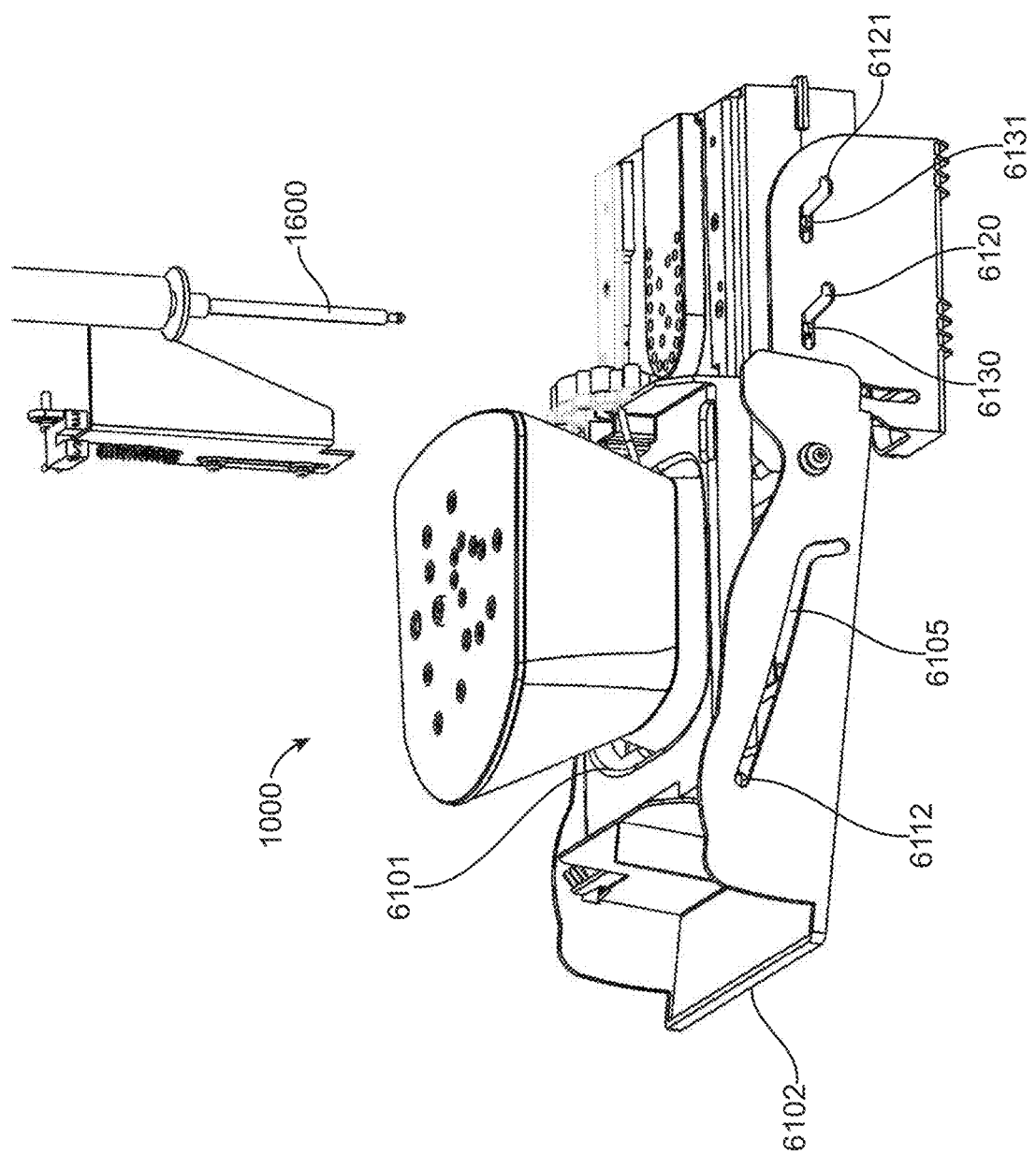
FIG. 18C shows an internal view of a cartridge control module when the door is opened and when a cartridge is positioned for loading.

By way of further demonstration, the door action is shown in FIGS. 18A, 18B and 18C. FIG. 18A shows an internal view of cartridge control module 6000 when door 6102 is closed. In this position magnets 5501 are in the proud position ready to interact with pistons of a reagent cartridge and receptacle 6101 is positioned to hold the cartridge in place for fluidic activity. FIG. 18B provides the internal view of the cartridge control module 6000 when the door 6102 is partially opened and magnets of valve actuators are retracted. The receptacle 6101 is in the same position as when the door was closed since pin 6112 has not passed the bend in the hockey stick shaped track 6105 and pins 6130 and 6131 have not passed the bends in tracks 6120 and 6121, respectively. FIG. 18C shows the internal view of the cartridge control module 6000 when the door 6102 is opened and when cartridge 1000 is positioned for loading. In this position receptacle 6101 has slid out to allow the user to easily handle cartridge 1000 and magnets 5501 are retracted.

The door 6102 and cartridge receptacle 6101 form a mechanical interlock that ensures the proper loading and unloading of the cartridge. The combination of the hockey stick shape of track 6105 and position of the slots 6120 and 6121 in the cartridge tray ensure that (1) the magnets 5501 are retracted until the cartridge 1000 is moved into place during loading (closing of the door); (2) the magnets 5501 are retracted before the cartridge 1000 is moved into or out of the control module; and (3) the magnets 5501 are efficiently moved into place once the cartridge 1000 is loaded. This provides an advantage of preventing the normally closed valves from opening during loading, thereby preventing unwanted drainage of liquids in the chambers into the fluid channel.

Cartridge module 6000 has an opening 6152 that is positioned to allow optical components of the optical detection module 6700 to interface with a flow cell that is attached to the cartridge 1000. A second opening 6153 allows wiring to pass between the two components. The optical detection module 6700 includes a laser diode 6711 and 10× objective (internal to optical train 6702) that directs emitted signals to 16 megapixel camera 6701. Also included is a single board computer 6712 for controlling instrument functions.

The present disclosure provides methods for performing cyclical reactions. The methods will be exemplified herein in the context of a nucleic acid sequencing reaction. However, those skilled in the art will understand from the teaching herein how to modify the methods, and the apparatus, for other cyclical reactions such as nucleic acid synthesis reactions, peptide sequencing reactions, peptide synthesis reactions, combinatorial small molecule synthesis reactions or the like.

Particularly useful sequencing reactions are Sequencing By Binding™ reactions as described in commonly owned U.S. patent application Ser. No. 14/805,381 (published as US 2017/0022553 A1); Ser. No. 15/677,870 (published as US 2018/0044715 A1); Ser. No. 15/851,383; 15/873,343; 15/712,632; 62/447,319; 62/440,624; or 62/450,397, each of which is incorporated herein by reference. Generally, methods for determining the sequence of a template nucleic acid molecule can be based on formation of a ternary complex (between polymerase, primed nucleic acid and cognate nucleotide) under specified conditions. The method can include an examination phase followed by a nucleotide incorporation phase.

The examination phase can be carried out in a flow cell having at least one template nucleic acid molecule primed with a primer; contacting the primed template nucleic acid molecule(s) with a first reaction mixture that includes a polymerase and at least one nucleotide type; observing the interaction of polymerase and a nucleotide with the primed template nucleic acid molecule(s), under conditions where the nucleotide is not covalently added to the primer(s); and identifying a next base in each template nucleic acid using the observed interaction of the polymerase and nucleotide with the primed template nucleic acid molecule(s). The interaction between the primed template, polymerase and nucleotide can be detected in a variety of schemes. For example, the nucleotides can contain a detectable label. Each nucleotide can have a distinguishable label with respect to other nucleotides. Alternatively, some or all of the different nucleotide types can have the same label and the nucleotide types can be distinguished based on separate deliveries of different nucleotide types to the flow cell. In some embodiments, the polymerase can be labeled. Polymerases that are associated with different nucleotide types can have unique labels that distinguish the type of nucleotide to which they are associated. Alternatively, polymerases can have similar labels and the different nucleotide types can be distinguished based on separate deliveries of different nucleotide types to the flow cell.

During the examination phase, discrimination between correct and incorrect nucleotides can be facilitated by ternary complex stabilization. A variety of conditions and reagents can be useful. For example, the primer can contain a reversible blocking moiety that prevents covalent attachment of nucleotide, and/or cofactors that are required for extension, such as divalent metal ions can be absent, and/or inhibitory divalent cations that inhibit polymerase-based primer extension can be present, and/or the polymerase that is present in the examination phase can have a chemical modification and/or mutation that inhibits primer extension, and/or the nucleotides can have chemical modifications that inhibit incorporation, such as 5' modifications that remove or alter the native triphosphate moiety.

The extension phase can then be carried out by creating conditions in the flow cell where a nucleotide can be added to the primer on each template nucleic acid molecule. In some embodiments, this involves removal of reagents used in the examination phase and replacing them with reagents that facilitate extension. For example, examination reagents can be replaced with a polymerase and nucleotide(s) that are capable of extension. Alternatively, one or more reagents can be added to the examination phase reaction to create extension conditions. For example, catalytic divalent cations can be added to an examination mixture that was deficient in the cations, and/or polymerase inhibitors can be removed or disabled, and/or extension competent nucleotides can be added, and/or a deblocking reagent can be added to render primer(s) extension competent, and/or extension competent polymerase can be added.

The above examination and extension phases can be carried out cyclically such that in each cycle a single next correct nucleotide is examined (i.e. the next correct nucleotide being a nucleotide that correctly binds to the nucleotide in a template nucleic acid that is located immediately 5' of the base in the template that is hybridized to the 3'-end of the hybridized primer) and, subsequently, a single next correct nucleotide is added to the primer. Any number of cycles can be carried out including, for example, at least 1, 2, 5, 10, 20, 25, 30, 40, 50, 75, 100, 150 or more cycles. Alternatively or additionally, the number of cycles can be capped at no more than 150, 100, 75, 50, 40, 30, 25, 20, 10, 5, 2 or 1 cycles.

Nucleic acid template(s), to be sequenced, can be added to a flow cell using any of a variety of known methods. In some embodiments, a single nucleic acid molecule is to be sequenced. The nucleic acid molecule can be delivered to a flow cell and can optionally be attached to a surface in the flow cell. In some embodiments, the molecule is subjected to single molecule sequencing. Alternatively, multiple copies of the nucleic acid can be made and the resulting ensemble can be sequenced. For example, the nucleic acid can be amplified on the surface using techniques set forth in further detail below.

In multiplex embodiments, a variety of different nucleic acid molecules (i.e. a population having a variety of different sequences) are sequenced. The molecules can optionally be attached to a surface in a flow cell. The nucleic acids can be attached at unique features on the surface and spatially distinguishable nucleic acids can be sequenced in parallel. Alternatively, the nucleic acids can be amplified on the surface to produce a plurality of surface attached ensembles. The ensembles can be spatially distinguishable and sequenced in parallel.

A method set forth herein can use any of a variety of amplification techniques in a flow cell. Exemplary techniques that can be used include, but are not limited to, polymerase chain reaction (PCR), rolling circle amplification (RCA), multiple displacement amplification (MDA), bridge amplification, or random prime amplification (RPA). In particular embodiments, one or more primers used for amplification can be attached to a surface in a flow cell. Methods that result in one or more features on a solid support, where each feature is attached to multiple copies of a particular nucleic acid template, can be referred to as "clustering" methods.

In PCR embodiments, one or both primers used for amplification can be attached to the surface. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658 or 7,115,400; U.S. Patent Pub. Nos. 2002/0055100, 2004/0096853, 2004/0002090, 2007/0128624 or 2008/0009420, each of which is incorporated herein by reference. PCR amplification can also be carried out with one of the amplification primers attached to the surface and the second primer in solution. An exemplary format that uses a combination of one solid phase-attached primer and a solution phase primer is known as primer walking and can be carried out as described in U.S. Pat. No. 9,476,080, which is incorporated herein by reference. Another example is emulsion PCR which can be carried out as described, for example, in Dressman et al., *Proc. Natl. Acad. Sci. USA* 100:8817-8822 (2003), WO 05/010145, or U.S. Patent Pub. Nos. 2005/0130173 or 2005/0064460, each of which is incorporated herein by reference.

RCA techniques can be used in a method set forth herein. Exemplary reagents that can be used in an RCA reaction and principles by which RCA produces amplicons are described, for example, in Lizardi et al., *Nat. Genet.* 19:225-232 (1998) or US Pat. App. Pub. No. 2007/0099208 A1, each of which is incorporated herein by reference. Primers used for RCA can be in solution or attached to a surface in a flow cell.

MDA techniques can also be used in a method of the present disclosure. Some reagents and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection, Academic Press, Inc.,* 1995; Walker et al., *Nucl. Acids Res.* 20:1691-96 (1992); or U.S. Pat. Nos. 5,455,166; 5,130,238; or 6,214,587, each of which is incorporated herein by reference. Primers used for MDA can be in solution or attached to a surface in a flow cell.

In particular embodiments a combination of the above-exemplified amplification techniques can be used. For example, RCA and MDA can be used in a combination wherein RCA is used to generate a concatemeric amplicon in solution (e.g. using solution-phase primers). The amplicon can then be used as a template for MDA using primers that are attached to a surface in a flow cell. In this example, amplicons produced after the combined RCA and MDA steps will be attached in the flow cell. The amplicons will generally contain concatemeric repeats of a target nucleotide sequence.

Nucleic acid templates that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Thus, a mixture of nucleic acids used herein can be derived from a biological source, synthetic source or amplification product. Primers used herein can be DNA, RNA or analogs thereof.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Nucleic acids can also be derived from a prokaryote such as a bacterium, *Escherichia coli*, staphylococci or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual, 3rd edition*, Cold Spring Harbor Laboratory, New York (2001) or in Ausubel et al., *Current Protocols in Molecular Biology*, John Wiley and Sons, Baltimore, Md. (1998), each of which is incorporated herein by reference.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. No. 6,355,431 or 9,045,796, each of which is incorporated herein by reference. Amplification can also be carried out using a method set forth in Sambrook et al., *Molecular Cloning: A Laboratory Manual, 3rd edition*, Cold Spring Harbor Laboratory, New York (2001) or in Ausubel et al., *Current Protocols in Molecular Biology*, John Wiley and Sons, Baltimore, Md. (1998), each of which is incorporated herein by reference.

Figure 9:
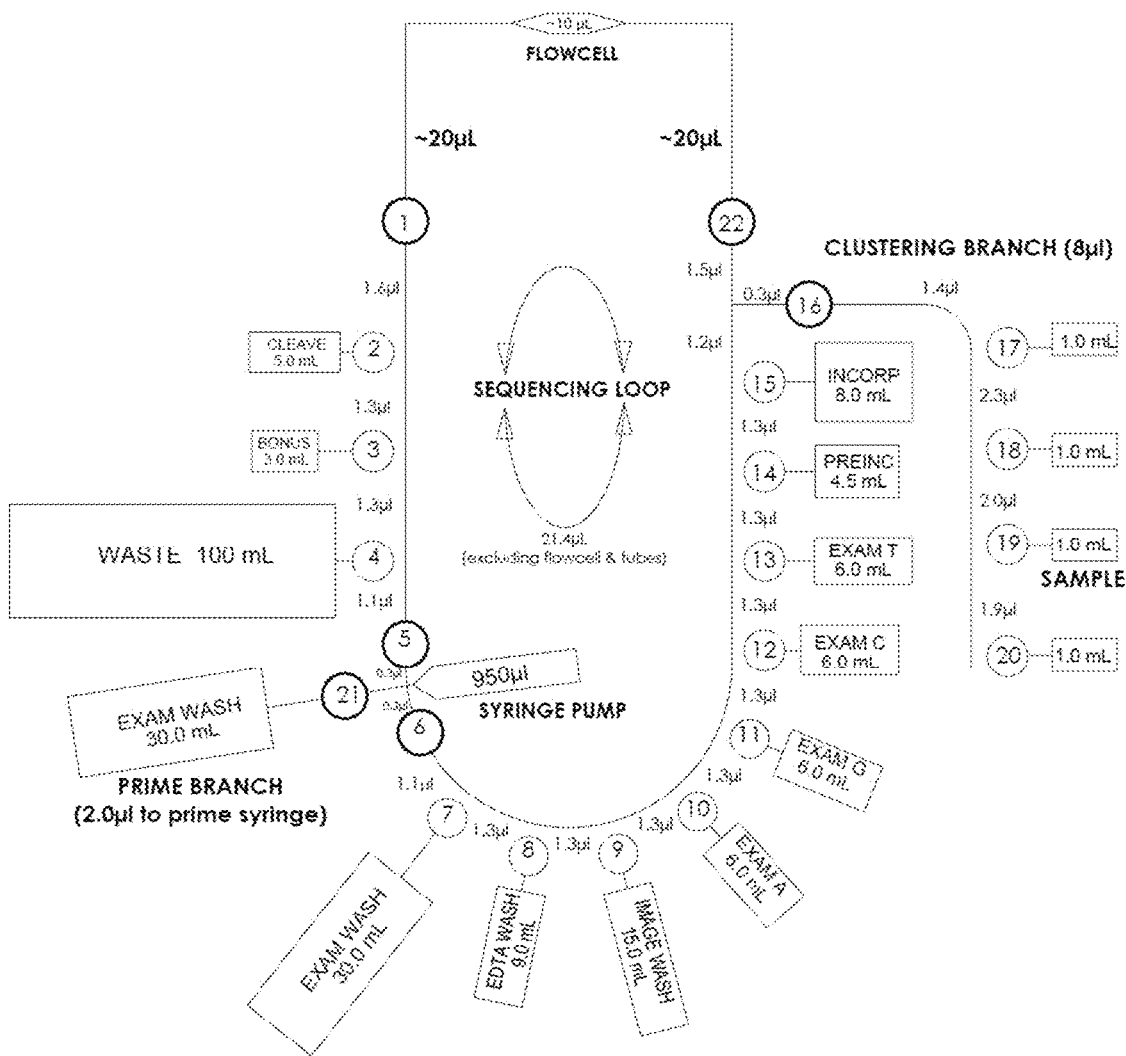
FIG. 9 shows a diagrammatic map of a fluidic loop between a valve manifold and flow cell.

An exemplary nucleic acid sequencing method is demonstrated by the fluid path diagram in FIG. 9 and the valve actuation schedules in FIGS. 10A-10B. The fluid path includes a flow cell having a 10 µl volume (indicated by the hexagonal symbol) that is attached at either end to a fluidic loop. The fluidic loop includes valves numbered 1-15 and 22, which correspond to valve components 1131-1145 and 1152, respectively, in FIGS. 2A-2F. The fluidic loop is attached to a clustering branch that includes valves 16-20, which correspond to valve components 1146-1150, respectively, in FIGS. 2A-2F. A priming branch is also attached to the fluidic loop and includes valve 21, which corresponds to valve feature 1151 in FIGS. 2A-2F. Valves 2-4, 7-15, 17-20 and 21 mediate flow of reagents from individual reservoirs shown as rectangles in FIG. 9. The volume of the fluid line between each of the valves is indicated in microliters in FIG. 9. The reservoirs correspond to reservoirs 1102-1104, 1107-1115, 1117-1120 and 1121, respectively, in FIGS. 2A-2F.

The reservoirs in the clustering branch accommodate 1 ml each of four different reagents for creating clusters in the flow cell. Specifically, the reservoir that is actuated by valve 20 contains a surface preparation reagent which is used to prepare the flow cell surface for nucleic acid amplification. The reservoir that is actuated by valve 19 contains a sample of DNA that is to be amplified and sequenced on the surface of the flow cell. Reservoirs that are actuated by valves 18 and 17 contain reagents for rolling circle amplification of the DNA sample on the flow cell surface.

Steps for priming the fluid lines and preparing nucleic acid clusters can be carried out in order down the table shown in FIG. 10A. The table shows the direction of pressure applied to the system from the syringe pump which interfaces with the loop between valves 5 and 6, and indicates which valves are actuated from the normally closed configuration to open (open valves indicated by "0"). The table also shows the resulting direction of flow through the system as diagramed in FIG. 9. In the schedule shown, the syringe is primed by pulling wash fluid from the reservoir actuated by valve 21. Then the main channel is primed by pushing wash fluid from the syringe into various valve actuated sections of the main channel, and the cluster branch is primed by pulling fluid from the reservoir activated by valve 20 into the main channel via valve 16.

Clustering is then carried out using a series of four reagents that are pulled from reservoirs actuated by valves 20, 19, 18 and 17, respectively. A flow rate is selected that moves a volume that is at least equivalent to the sum of the volume of the flow cell and the dead volume between the reservoir and the flow cell. In some situations, excess volume can be moved. In a first super wash, the pump applies negative pressure, but the direction of flow is changed by closing valve 5 and opening valve 6. Valve 3 is also opened such that wash fluid is pulled from the reservoir at valve 3 through the flow cell and into the syringe barrel. The flow cell is then washed a second time by pushing the contents of the syringe barrel through valve 5, through the flow cell, through valve 16 and into the reservoir controlled by valve 20.

The reservoirs in the main loop contain reagents for the sequencing steps. The extension phase of the sequencing reaction utilizes reservoirs actuated by valves 2, 14, 15 and 21. Specifically, the reservoir that is actuated by valve 14 contains pre-incorporation reagent, which is used to prepare a primed nucleic acid template for nucleotide incorporation. The reservoir that is actuated by valve 2 contains cleave reagent, which is used to deblock the primer by removing reversible terminator moiety from the 3' end of the primer. The reservoir that is actuated by valve 15 contains incorporation reagent, which contains polymerase and a mixture of four different reversibly terminated nucleotide types for extending the deblocked primer by a single nucleotide. The reservoir that is actuated by valve 21 contains a wash solution. The examination phase of the sequencing reaction utilizes reservoirs actuated by valves 8, 10, 11, 12, 13 and 21. Specifically, the reservoir that is actuated by valve 8 contains EDTA wash, which is used during detection of the flow cell. The reservoirs that are actuated by valves 10-13 contain labeled polymerase and one of nucleotides A, G, C and T, respectively, which are used to detect the next correct nucleotide in the primed template.

The steps for each cycle of the sequencing reaction are carried out in order down the table shown in FIG. 10A. As demonstrated by comparison of the schedule to the flow diagram in FIG. 9, the cleave reagent is located at a reservoir that is adjacent to the left side of the flow cell. The cleave reagent enters the left side of the flow cell in a clockwise direction and in the subsequent wash step the direction of flow changes such that the cleave reagent exits the left side, moving counterclockwise to a waste reservoir that is between the cleave reservoir and the pump. All other reagents and washes flow counterclockwise through the loop to enter the right side of the flow cell and then continue counterclockwise to the waste reservoir. This configuration minimizes contact of the other reagents with cleave reagent prior to entry into the flow cell. As such unwanted side reactions that would cause artifacts such as phasing problems are minimized.

As also evident from FIG. 9 and FIG. 10B, the sequencing cycle includes several reaction and detection steps separated by wash steps. Specifically, in the first step of the cycle, cleave reagent is delivered to remove blocking groups from the nascent primer in the flow cell. Then a mixture of polymerase and four blocked nucleotides is delivered to cause incorporation of a blocked nucleotide into the deblocked primer. Then four examinations are carried out each for a different nucleotide (in order adenosine (A), guanine (G), cytosine (C), and thymine (T)). Each examination includes delivery of the respective nucleotide with a polymerase, under ternary complex stabilization conditions (i.e. the primer is not extended by the nucleotide) and the ternary complex is detected during (or immediately after) delivery of EDTA reagent. The cycle, which lasts 147 seconds in the example shown, can be repeated any number of times.

It will be understood that any of a variety of sequencing reactions can be carried out using an apparatus and method of the present disclosure. The placement, volume and number of reservoirs can be modified to accommodate such sequencing reactions and/or different clustering methods set forth herein. Exemplary sequencing methods are set forth below.

Sequencing-by-synthesis (SBS) techniques can also be used. SBS generally involves the enzymatic extension of a nascent primer through the iterative addition of nucleotides against a template strand to which the primer is hybridized. Briefly, SBS can be initiated by contacting target nucleic acids, attached to features in a flow cell, with one or more labeled nucleotides, DNA polymerase, etc. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, reagents and detection instruments that can be readily adapted for use with an array produced by the methods of the present disclosure are described, for example, in Bentley et al., Nature 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference. Also useful are SBS methods that are commercially available from Illumina, Inc., San Diego Calif.

Some SBS embodiments include detection of a proton released upon incorporation of a nucleotide into an extension product. For example, sequencing based on detection of released protons can use reagents and an electrical detector that are commercially available from Thermo Fisher (Waltham, Mass.) or described in US Pat. App. Pub. Nos. 2009/0026082 A1; 2009/0127589 A1; 2010/0137143 A1; or 2010/0282617 A1, each of which is incorporated herein by reference.

Other sequencing procedures can be used, such as pyrosequencing. Pyrosequencing detects the release of inorganic pyrophosphate (PPi) as particular nucleotides are incorporated into a nascent primer hybridized to a template nucleic acid strand (Ronaghi, et al., *Analytical Biochemistry* 242 (1), 84-9 (1996); Ronaghi, *Genome Res.* 11 (1), 3-11 (2001); Ronaghi et al. *Science* 281 (5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system.

Sequencing-by-ligation reactions are also useful including, for example, those described in Shendure et al. *Science* 309:1728-1732 (2005); U.S. Pat. No. 5,599,675; or U.S. Pat. No. 5,750,341, each of which is incorporated herein by reference. Some embodiments can include sequencing-by-hybridization procedures as described, for example, in Bains et al., *Journal of Theoretical Biology* 135 (3), 303-7 (1988); Drmanac et al., *Nature Biotechnology* 16, 54-58 (1998); Fodor et al., *Science* 251 (4995), 767-773 (1995); or WO 1989/10977, each of which is incorporated herein by reference. In both sequencing-by-ligation and sequencing-by-hybridization procedures, primers that are hybridized to nucleic acid templates are subjected to repeated cycles of extension by oligonucleotide ligation. Typically, the oligonucleotides are fluorescently labeled and can be detected to determine the sequence of the template.

Some embodiments can utilize methods involving real-time monitoring of DNA polymerase activity. For example, nucleotide incorporations can be detected through fluorescence resonance energy transfer (FRET) interactions between a fluorophore-bearing polymerase and gamma-phosphate-labeled nucleotides, or with zeromode waveguides (ZMW). Techniques and reagents for sequencing via FRET and or ZMW detection are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Throughout this application various publications, patents and/or patent applications have been referenced. The disclosures of these documents in their entireties are hereby incorporated by reference in this application.

The term "comprising" is intended herein to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

A number of embodiments have been described. Nevertheless, it will be understood that various modifications may be made. Accordingly, other embodiments are within the scope of the following claims.

What is claimed is:

1. A reagent cartridge, comprising
   (a) a support comprising a plurality of reservoirs;
   (b) a main channel within the support, the channel comprising a first end exiting the support and a second end exiting the support;
   (c) a pump channel that connects the exterior of the support to a portion of the main channel that is between the first and second ends;
   (d) a valve manifold in the support, comprising
      (i) a first passage at the first end of the main channel,
      (ii) a second passage at the second end of the main channel,
      (iii) a first master valve that is placed in the main channel between the pump channel and the first end of the main channel,
      (iv) a second master valve that is placed in the main channel between the pump channel and the second end of the main channel,
      (v) a plurality of reservoir valves for regulating flow from individual reservoirs to the main channel, wherein the reservoir valves are diaphragm valves positioned to communicate with the main channel at a position between the first and second ends, and
      (vi) an elastomer sheet attached to a plurality of magnetic pistons,
   wherein the plurality of reservoirs contains reagents for completing at least 10 cycles of a nucleic acid sequencing technique, and wherein each of the cycles comprises sequential delivery of reagents from multiple reservoirs of the plurality of reservoirs.

2. The reagent cartridge of claim 1, further comprising a first flow cell valve for regulating flow through the first passage.

3. The reagent cartridge of claim 1, further comprising a second flow cell valve for regulating flow through the second passage.

4. The reagent cartridge of claim 1, wherein the plurality of reservoirs includes a waste reservoir for accepting the reagents for completing the cycles.

5. The reagent cartridge of claim 4, wherein the volume of the waste reservoir has a volume that is at least 80% of the total volume of the reagents for completing the cycles.

6. The reagent cartridge of claim 1, wherein the plurality of reservoirs further comprises an amplification reservoir containing reagents for solid phase amplification of nucleic acids.

7. The reagent cartridge of claim 1, further comprising a flow cell having a detection channel, the detection channel having a first end fluidically connected to the first passage and the detection channel having a second end fluidically connected to the second passage, whereby the main channel and detection channel form a fluidic loop.

8. The reagent cartridge of claim 7, wherein the detection channel comprises a detection surface, the detection surface having nucleic acids attached thereto.

9. The reagent cartridge of claim 8, wherein the detection surface is transparent to visible light.

10. The reagent cartridge of claim 7, wherein the detection channel comprises a window that is transparent to visible light.

11. The reagent cartridge of claim 7, wherein the fluidic loop comprises, in relative order, the connection to the pump channel, the second master valve, a reservoir valve for a wash reservoir that contains a wash reagent, reservoir valves for nucleotide reservoirs that contain nucleotide analogs, the second passage, the flow cell, the first passage and the first master valve.

12. The reagent cartridge of claim 11, wherein the plurality of reservoirs further comprises a waste reservoir for accepting the reagents for completing the cycles, a reagent valve for the waste reservoir located in the fluidic loop between the first passage and the first master valve.

13. The reagent cartridge of claim 12, wherein the plurality of reservoirs further comprises an amplification reservoir containing a reagent for solid phase amplification of nucleic acids, a reagent valve for the amplification reservoir located in the fluidic loop between the reservoir valves for nucleotide reservoirs and the second passage.

14. The reagent cartridge of claim 13, wherein the plurality of reservoirs further comprises a deblocking reservoir containing a reagent for removing a reversible terminator from the 3' end of a nucleic acid, a reagent valve for the deblocking reservoir located in the fluidic loop between the second passage and the reagent valve for the waste reservoir.

15. The reagent cartridge of claim 1, wherein the plurality of reservoir valves are normally closed and are opened by magnetic force applied to the magnetic pistons.

16. The reagent cartridge of claim 1, wherein the support comprises a body component and a foot component, wherein the elastomer sheet is compressed between the body component and the foot component.

17. The reagent cartridge of claim 16, wherein the plurality of reservoirs, the main channel and the pump channel are present in the body component, and wherein the foot component comprises housings for the magnetic pistons.

18. A nucleic acid sequencing apparatus comprising the reagent cartridge of claim 1.

19. The nucleic acid sequencing apparatus of claim 18, further comprising a syringe pump connected to the pump channel.

20. The nucleic acid sequencing apparatus of claim 18, further comprising a flow cell having a detection channel, the detection channel having a first end fluidically connected to the first passage and the detection channel having a second end fluidically connected to the second passage.

21. The nucleic acid sequencing apparatus of claim 20, further comprising a detector configured to detect nucleic acids in the flow cell.

22. The reagent cartridge of claim 1, further comprising a first flexible tube having a first end attached to the first end of the main channel and having a second end protruding from the support.

23. The reagent cartridge of claim 22, further comprising a second flexible tube having a first end attached to the second end of the main channel and having a second end protruding from the support.

24. The reagent cartridge of claim 23, further comprising a metal sheet contained within a chamber of the support, wherein the first flexible tube and the second flexible tube are attached to the cartridge by compression of exterior surfaces of the first flexible tube and the second flexible tube against an edge of the metal sheet.

25. The reagent cartridge of claim 24, wherein the edge of the metal sheet contacts the first flexible tube and the second flexible tube at an acute or obtuse angle with respect to the length of each of the first flexible tube and the second flexible tube.

26. The reagent cartridge of claim 1, further comprising a lid that is configured to rotate between an open position and a closed position, the open position providing fluidic access from outside the support to the insides of the reservoirs.

27. The reagent cartridge of claim 26, wherein the lid further comprises gas vents that connect each of the reservoirs to the outside of the support when the lid is in the closed position.

* * * * *